(12) United States Patent
Kellum

(10) Patent No.: US 10,381,118 B2
(45) Date of Patent: Aug. 13, 2019

(54) CARDIAC ARREST EVENT (CODE) SUPPORT SYSTEM, EQUIPMENT AND METHODOLOGIES PROVIDING RECORDATION, DOCUMENTATION, ANALYSIS, FEEDBACK AND POST EVENT PROCESSING

(71) Applicant: Scientific Pathways International, LLC, Lake Geneva, WI (US)

(72) Inventor: Michael Kellum, Whitewater, WI (US)

(73) Assignee: Scientific Pathways International, LLC, Lake Geneva, WI (US)

( * ) Notice: Subject to any disclaimer, the term of this patent is extended or adjusted under 35 U.S.C. 154(b) by 4 days.

(21) Appl. No.: 15/828,369

(22) Filed: Nov. 30, 2017

(65) Prior Publication Data

US 2018/0158553 A1  Jun. 7, 2018

Related U.S. Application Data

(63) Continuation of application No. 14/281,138, filed on May 19, 2014, now abandoned, which is a continuation-in-part of application No. 14/199,331, filed on Mar. 6, 2014, now abandoned, which is a continuation-in-part of application No. 12/375,091, filed as application No. PCT/US2007/074473 on Jul. 26, 2007, now abandoned.

(Continued)

(51) Int. Cl.
| | |
|---|---|
| G06F 19/00 | (2018.01) |
| G16H 50/30 | (2018.01) |
| G16H 15/00 | (2018.01) |
| G16H 40/20 | (2018.01) |
| G16H 10/60 | (2018.01) |

(52) U.S. Cl.
CPC .......... *G16H 50/30* (2018.01); *G06F 19/325* (2013.01); *G06F 19/326* (2013.01); *G16H 15/00* (2018.01); *G16H 40/20* (2018.01); *G06F 19/328* (2013.01); *G16H 10/60* (2018.01)

(58) Field of Classification Search
CPC ...... G06F 19/325; G06F 19/326; G06F 19/00; G06F 19/328; G16H 15/00; G16H 40/20; G16H 50/30; G16H 10/60
See application file for complete search history.

(56) References Cited

U.S. PATENT DOCUMENTS

| | | | |
|---|---|---|---|
| 4,915,635 A | 4/1990 | Ingenito et al. | |
| 5,899,866 A | 5/1999 | Cyrus et al. | |

(Continued)

FOREIGN PATENT DOCUMENTS

WO   2012/047504 A1   4/2012

OTHER PUBLICATIONS

International Search Report for International Patent Application No. PCT/US2014/038599, dated Sep. 8, 2014.

(Continued)

*Primary Examiner* — Rinna Yi

(74) *Attorney, Agent, or Firm* — Jansson Munger McKinley & Kirby, Ltd.

(57) ABSTRACT

Disclosed embodiments are directed at providing a cardiac arrest event support system, equipment and methodologies that enable recordation, documentation, real time analysis, feedback to personnel treating a victim of the event and post event processing to support objective documentation and post event processing (e.g., inventory, billing, etc.).

5 Claims, 57 Drawing Sheets

Related U.S. Application Data

(60) Provisional application No. 61/824,423, filed on May 17, 2013, provisional application No. 60/820,466, filed on Jul. 26, 2006.

(56) References Cited

U.S. PATENT DOCUMENTS

| | | |
|---|---|---|
| 6,321,113 B1 | 11/2001 | Parker et al. |
| 6,351,671 B1 | 2/2002 | Myklebust et al. |
| 6,489,974 B1 | 12/2002 | Johnson et al. |
| 6,697,671 B1 | 2/2004 | Nova et al. |
| 7,849,440 B1 | 12/2010 | Englehart |
| 8,308,544 B2 | 11/2012 | Friedman et al. |
| 8,424,904 B2 | 4/2013 | Cech |
| 2003/0060723 A1 | 3/2003 | Joo |
| 2003/0233129 A1 | 12/2003 | Matos |
| 2004/0124979 A1 | 7/2004 | Medema et al. |
| 2004/0267325 A1 | 12/2004 | Geheb et al. |
| 2006/0173501 A1 | 8/2006 | Stickney et al. |
| 2007/0060785 A1 | 3/2007 | Freeman et al. |
| 2010/0304842 A1 | 12/2010 | Friedman et al. |
| 2011/0101654 A1 | 5/2011 | Cech |
| 2011/0160544 A1 | 6/2011 | Hayter |
| 2011/0288889 A1 | 11/2011 | Jones et al. |
| 2013/0054271 A1 | 2/2013 | Langford et al. |
| 2014/0032230 A1 | 1/2014 | Gelber |

OTHER PUBLICATIONS

International Search Report for International Patent Application No. PCT/US2007/074473, dated May 29, 2008.

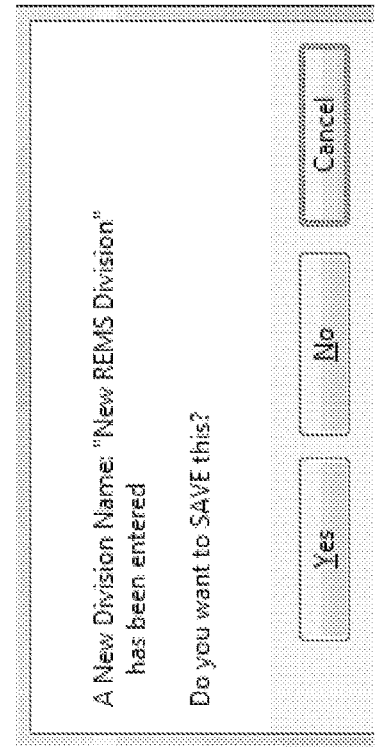
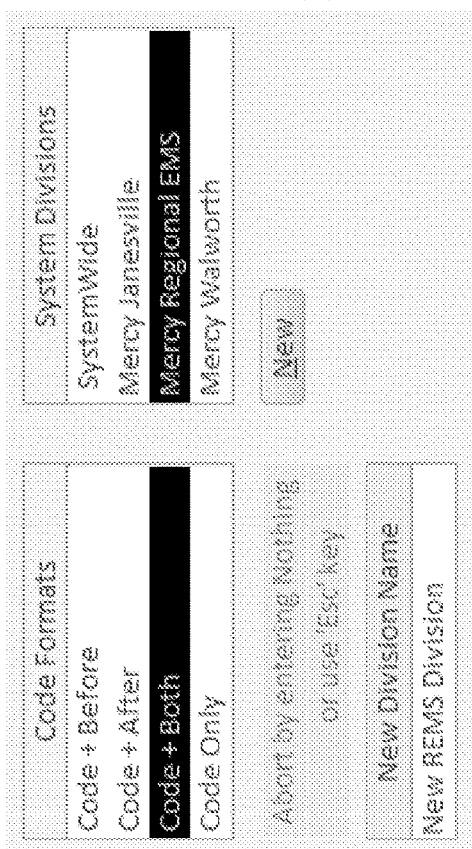
FIGURE 4B
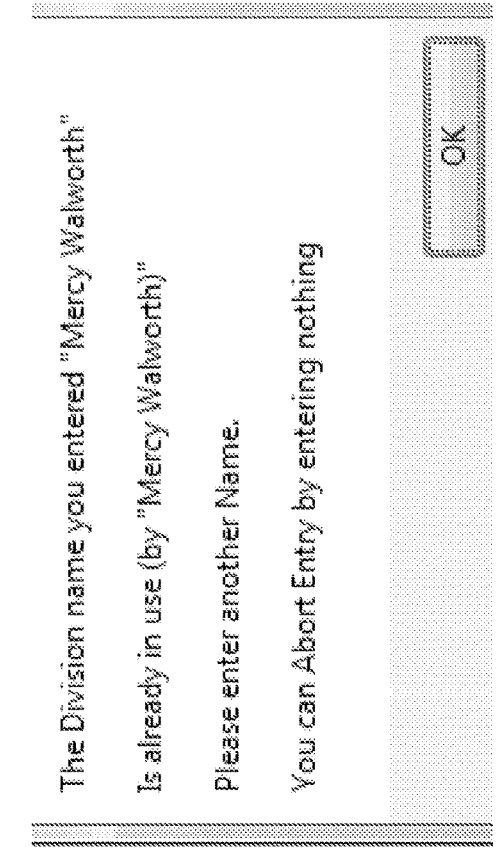
FIGURE 4C

FIGURE 5

| Type of Word | Words |
|---|---|
| Code Events | All Clear |
| Topics Discussed | Apply O2 |
| Recognized Something | Assigns Roles |
| Actions Taken | Call for Help |
| | EKG Done |
| | Heard Page |
| | Is Captain |
| | Lab Tests Done |
| | Leads On Okay |

| Type of Word | Words |
|---|---|
| Code Events | A Fib |
| Topics Discussed | Asystole |
| Recognized Something | Know Is PNB |
| Actions Taken | Knows ROSC |
| | Mobitz 2 |
| | PEA |
| | Pulseless VT |
| | Sinus Brady |
| | SVT |
| | V Fib |

FIGURE 21
FIGURE 22
FIGURE 23

| Actions Entered: | |
|---|---|
| 0:00 | Start of Code |
| 0:00 | etCO2 in Protocol |
| 0:00 | LUCAS in Protocol |
| 0:00 | Do ET after 1st NonShockable |
| 0:00 | Doing CCR |
| 0:00 | Using Manual Defibrillator |
| 0:12 | Metronome |
| 0:13 | Monitor |
| 0:14 | Start CC |

FIGURE 35

○ Metronome ● CC ○ Monitor ○ Airway ○ IV/IO ○ Drugs ○ Pauses ○ CC Summary

Passed

Metronome - Started before Compressions
Metronome - WAS Used

FIGURE 42

○ Metronome ● CC ○ Monitor ○ Airway ○ IV/IO ○ Drugs ○ Pauses ○ CC Summary

Failed

CC Set @15:08:59 was Too BRIEF, lasting 29" (BM is 100")
CC Set @15:09:28 was Too BRIEF, lasting 66" (BM is 100")
CC Set starting @14:54:31 went 237" without a Switch of Compressors (BM is 75")
CC Set starting @14:58:28 went 126" without a Switch of Compressors (BM is 75")
CC Set starting @15:00:34 went 149" without a Switch of Compressors (BM is 75")
CC Set starting @15:03:24 went 80" without a Switch of Compressors (BM is 75")
CC Set starting @15:04:44 went 113" without a Switch of Compressors (BM is 75")
CC Set starting @15:06:49 went 92" without a Switch of Compressors (BM is 75")
LUCAS was available but never applied Passed 60.1% of CC were performed with "Fresh" Compressors
90.1% of CC were in Sets with acceptable durations (BM of 100-150")

FIGURE 43

○ Metronome   ○ CC   ● Monitor   ○ Airway   ○ IV/IO   ○ Drugs   ○ Pauses   ○ CC Summary

Failed
No Analysis before rhythm @14:58:24
No Analysis before rhythm @15:06:32
No subsequent Rhythm or Shock/No-Shock

Passed
Crash Cart - Present before start of recording
Decision to @15:10:39 was On Time (-10′59″) after a Non-Shockable Rhythm (BM is 3″)
Decision to Shock @14:56:15 was On Time (2″) after a Shockable Rhythm (BM is 3″)
Decision to Shock @14:58:24 was On Time (2″) after a Shockable Rhythm (BM is 3″)
Decision to Shock @15:00:28 was On Time (3″) after a Shockable Rhythm (BM is 3″)
Decision to Shock @15:02:33 was On Time (2″) after a Shockable Rhythm (BM is 3″)
Decision to Shock @15:04:35 was On Time (1″) after a Shockable Rhythm (BM is 3″)
Decision to Shock @15:06:32 was On Time (2″) after a Shockable Rhythm (BM is 3″)
Decision to Shock @15:08:35 was On Time (3″) after a Shockable Rhythm (BM is 3″)
Monitor - On 0″ after available (BM is 30″)
Pad application - Occurred BEFORE 1st Rhythm Analysis

FIGURE 44

○ Metronome ○ CC ○ Monitor ● Airway ○ IV/IO ○ Drugs ○ Pauses ○ CC Summary

Failed

Airway Patency Check was not performed
O2 Application was not performed
OPA/NPA insertion was not performed Passed etCO2 not needed - No invasive airway inserted
Failure of Invasive Airway - Did NOT occur
Invasive Airway not needed - ROSC or End of Code occurred

FIGURE 45

○ Metronome ○ CC ○ Monitor ○ Airway ● IV/IO ○ Drugs ○ Pauses ○ CC Summary

Failed

IV Retry @15:01:00 was BEFORE IO attempt @15:07:00
IV/IO - Neither IV or IO attempted

FIGURE 46

○ Metronome　○ CC　○ Monitor　○ Airway　○ IV/IO　● Drugs　○ Pauses　○ CC Summary

Failed 1 dose of Epi was given after IO Completed - too MANY (BM is 0-0 doses)
Amiodarone - 1st dose @15:07:00 was 615" LATE (after 1st Shockable rhythm) (BM is 30")
Amiodarone - 2nd dose @15:12:00 was 786" LATE (after 2nd Shockable rhythm) (BM is 30")
There were 112" between ROSC and last Epi @15:02:08 where a repeat dose was indicated Passed Amiodarone - 1st Dose was 300 mg
Amiodarone - 2nd Dose was 150 mg

FIGURE 47

○ Metronome  ○ CC  ○ Monitor  ○ Airway  ○ IV/IO  ○ Drugs  ● Pauses  ○ CC Summary

Failed

5% of 8 Analyze Rhythm pauses (1 of 21") were NOT necessary
71% of 7 Resume CC after Shock/NoShock pauses (50 of 70") were NOT necessary
78% of 1 Start of Recording pause (71 of 91") was NOT necessary
for Other Reason Pauses - All (8") were NOT necessary
Peek at Rhythm Pauses - All (17") were NOT necessary
Pulse Check Pause - All (2") were NOT necessary

Passed

All of Resume after Shock pauses were necessary
All of ROSC pauses were necessary
No pauses for Apply LUCAS occurred
No pauses for Applying Pads occurred
No pauses for Charging occurred
No pauses for ET Insertion occurred
No pauses for Resume after NoShock occurred
No pauses for Switching CC occurred
No pauses for Ventilations occurred

FIGURE 48

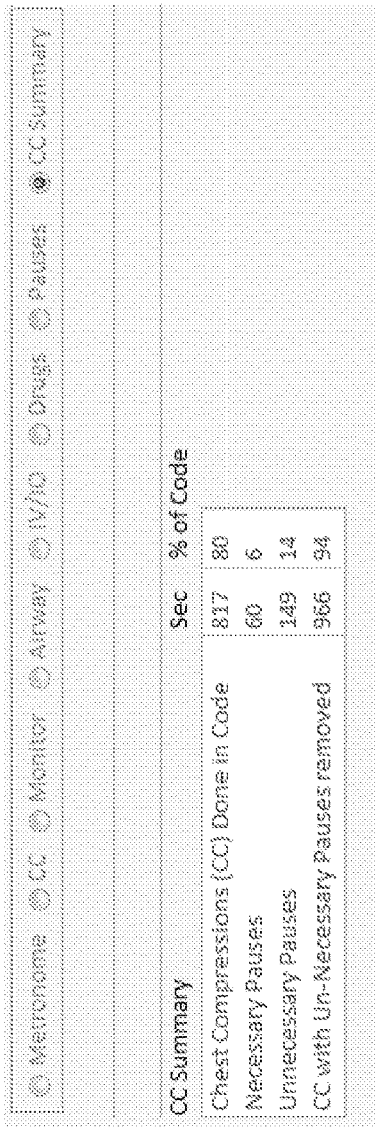
FIGURE 49
FIGURE 50
FIGURE 51
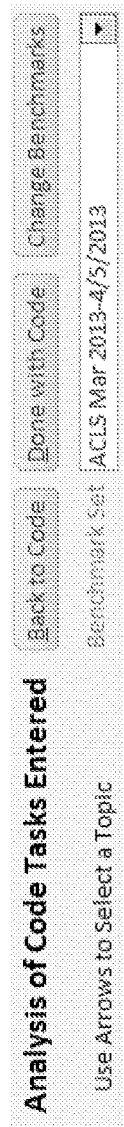
FIGURE 52

| Time | Code Tasks |
|---|---|
| 00:00 | Start of Code |
| 00:00 | etCO2 in Protocol |
| 00:00 | LUCAS in Protocol |
| 00:00 | Do ET after 1st NonShockable |
| 00:00 | Doing CCR |
| 00:00 | Using Manual Defibrillator |
| 00:02 | Metronome |
| 00:05 | Patency Ck |

FIGURE 54

Analysis of Code Tasks Entered | Back to Code | Done with Code | Change Benchmarks | Show Code Details

FIGURE 55

Archive Cardiac Arrest Code Data

Save

Arrest Type: Real
Arrest Date: 4/15/2013
Arrest Time:
Site:
Recorder: Kellum, Mike J.

Team Leaders

Physician:
Nurse:
RT:

Use TAB to exit from here

Comments:

| Sec | Name - Dbl-Click to Modify Sec | Benchmark seconds 20 |
|---|---|---|
| 15 | Metronome - To Start after Starting CC | |

FIGURE 62A

| Sec | Name - Dbl-Click to Modify Sec |
|---|---|
| 20 | Metronome - To Start after Starting CC |

FIGURE 62B

| | |
|---|---|
| 150 | CC - Duration - Max |
| 100 | CC - Duration - Min |
| 75 | CC - Time between Switching Compressors |
| 20 | Start CC - after Prior Rhythm Analysis - AED |
| 8 | Start CC - after Prior Rhythm Analysis - Manual |
| 8 | Start CC - after Prior Rhythm detected |
| 3 | Start CC - after Prior Shock/NoShock |
| 20 | Start CC - after Start of Recording |

○ Metronome
● CC
○ Monitor
○ Airway
○ IV/IO
○ Drugs
○ Pauses

FIGURE 63A

| Select Topic | Sec | Name - Dbl-Click to Modify Sec |
|---|---|---|
| ○ Metronome | 30 | Monitor - To Turn on after it's available |
| ○ CC | 5 | Pads - To apply - doing CCR |
| ● Monitor | 10 | Pads - To apply - doing CPR |
| ○ Airway | 10 | To Analyze Rhythm - AED |
| ○ IV/IO | 5 | To Analyze Rhythm - Manual defibrillator |
| ○ Drugs | 15 | To Charge - using AED |
| ○ Pauses | 0 | To Charge - using CCR & Manual defibrillator |
| | 10 | To Charge - using Manual defibrillator |
| | 5 | To Shock - after Rhythm Analysis |
| | 3 | To Shock - after Shockable Rhythm |

FIGURE 63B

Select Topic

○ Metronome
○ CC
○ Monitor
● Airway
○ IV/IO
○ Drugs
○ Pauses

| Sec | Name - Dbl-Click to Modify Sec |
|---|---|
| 120 | Initial Airway - after Start of Recording |
| 120 | Initial Airway - after Start CC |
| 360 | Invasive airway - Earliest time after Initial Rhythm - Shockable |
| 390 | Invasive airway - Latest time after Initial Rhythm - Shockable |
| 30 | Invasive airway - Max time after Initial Rhythm - Non-Shockable |
| 30 | Max Time after Initially NonShockable to Start ET |
| 15 | Start Mainstream etCO2 - after invasive airway ready |
| 60 | Start Sidestream etCO2 - after Start of Recording |
| 0 | To Ventilate if doing CCR |
| 5 | To Ventilate if doing CPR |

| Sec | Name - Dbl-Click to Modify Sec |
|---|---|
| 20 | Max time to Insert IO |
| 20 | Max time to Insert IV |

Select Topic
○ Metronome
○ CC
○ Monitor
○ Airway
● IV/IO
○ Drugs
○ Pauses

FIGURE 63E

| Sec | Name - Dbl-Click to Modify Sec |
|---|---|
| 3 | Max # of Epi doses allowed |
| 30 | Max time 1st Amiodarone after Shockable Rhythm |
| 15 | Max time 1st dose Epi after IV or IO ready |
| 30 | Max time between 1st Epi and 1st Vasopressin |
| 660 | Max time between 2nd and 1st Vasopressin doses |
| 300 | Max time between Epi doses |
| 540 | Min time between 2nd and 1st Vasopressin doses |
| 180 | Min time between Epi doses |

Select Topic
○ Metronome
○ CC
○ Monitor
○ Airway
○ IV/IO
● Drugs
○ Pauses

| Sec | Name - Dbl-Click to Modify Sec |
|---|---|
| 0 | Max pause - other reasons |
| 10 | Max pause to apply LUCAS |
| 0 | Max pause to do Pulse check - CCR |
| 10 | Max pause to do Pulse check - CPR |
| 0 | Max pause to insert ET - CCR |
| 10 | Max pause to insert ET - CPR |
| 0 | Max Sec Allowed for Peek@Rhythm Pause |
| 60 | Max time Crash Cart arrival - after Start of Recording |

Select Topic
- Metronome
- CC
- Monitor
- Airway
- IV/IO
- Drugs
- ● Pauses

Setup Show_Hides for each Action

Action: [        ]

| | | | | | | Action |
|---|---|---|---|---|---|---|
| Equipment Arrives | Metroname | Monitor | Crash Cart | etCO2 Main | etCO2 Side | Initial Shows |
| Event Happens | CodeTeam | Monitor On | Pads No Pause | LUCAS Failed | Lost ROSC | Test |
| CC | Switch | SAME person | Start CC | | | Test Over |
| Shocks | Shock | No Shock | | | | Exit |
| Rhythms | Shockable | NonShockable | | | ROSC | |
| Initial Airway | Patency Ck | OPA/NPA | O2 Applied | | | |
| Pauses | Analyz Rhythm | to Ventilate | to Insert ET | Apply LUCAS | to Apply Pads | |
| Pauses | to Check Pulse | to Charge | to Switch CC | Peek@Rhythm | Other Reason | |
| Drugs | Epi | Vasopressin | Amio 300 | | Amio 150 | |
| Drugs | Atropine | Calcium | Bicarb | Mg++ | Other Drug | |
| Interventions | ET Started | IV Started | IO Started | etCO2 Started | Other Airway | |
| Status | | | | | | |

FIGURE 71

CARDIAC ARREST EVENT (CODE) SUPPORT SYSTEM, EQUIPMENT AND METHODOLOGIES PROVIDING RECORDATION, DOCUMENTATION, ANALYSIS, FEEDBACK AND POST EVENT PROCESSING

CROSS-REFERENCE TO RELATED APPLICATION(S)

This application is a continuation of patent application Ser. No. 14/281,138, filed May 19, 2014, which claims the benefit of priority to Provisional Patent Application No. 61/824,423, filed May 17, 2013. The contents of application Ser. No. 14/281,138 and 61/824,423 are incorporated herein by reference in their entirety.

COMPUTER PROGRAM LISTING APPENDIX

The present application incorporates a text file, entitled "Exemplary_Software_Implementation.txt," (programmed in Microsoft® Access and provided in ASCII format). Such file is in the record of the parent patent application Ser. No. 14/281,138.

FIELD OF THE INVENTION

Disclosed embodiments are directed, generally, to a system, equipment and methodologies for documenting, analyzing, and processing data associated with a cardiac arrest's events.

DESCRIPTION OF THE RELATED ART

Sudden Cardiac Arrest (SCA) is second only to all cancer deaths combined as a cause of death in the United States. Each year between 300,000 and 450,000 persons die because their hearts abruptly stop pumping. Their death is sudden and without warning—they are alive one moment and a second later they've lost consciousness and collapse. They cannot call for help, and they die within minutes at the very same location where, moments before, they were standing or sitting or lying. Their lives are literally in the hands of whoever is present when and where they collapse. In the vast majority of cases this is a spouse, a neighbor or a stranger—individuals with the least amount of expertise in how to manage victims of SCA—and time is critical. In almost all such arrests, trained rescuers are summoned to complete the resuscitation process.

SUMMARY

To address this significant risk, disclosed embodiments have been developed and designed to provide an objective appraisal of the overall management of a cardiac arrest event. The following explanation presents a simplified summary in order to provide a basic understanding of some aspects of various embodiments. The summary is not an extensive overview and is neither intended to identify key or critical elements nor to delineate the scope of the disclosed invention. The following summary merely presents some concepts of the invention in a simplified form as a prelude to the more detailed description below.

Disclosed embodiments are directed at providing a cardiac arrest event support system, equipment and methodologies that enable recordation, documentation, real time objective analysis, immediately available feedback to trained personnel treating a victim of the event and post event processing to support objective documentation and post event processing (e.g., billing).

Disclosed embodiments are directed to enabling the ability to record and analyze the activities performed when treating an individual (real or simulated) with a cardiac arrest; and to present the results of that analysis for immediate feedback to the involved practitioners.

In accordance with at least one embodiment, a system and equipment are provided that enable real-time feedback for personnel responding to cardiac arrest while an arrest is ongoing.

BRIEF DESCRIPTION OF THE DRAWINGS

A more complete understanding of the present invention and the utility thereof may be acquired by referring to the following description in consideration of the accompanying drawings, in which like reference numbers indicate like features, and wherein:

FIGS. 4A-4F are exemplary illustrations of the functionality available to Administrators for developing Codes using the system provided in accordance with at least one disclosed embodiment.

FIG. 5 illustrates another example of the Code Development screen(s) provided in accordance with the disclosed embodiments.

FIGS. 6 and 7 are exemplary illustrations of the various options for how a screen may be organized around categories.

FIG. 8 is an exemplary illustration of how a word is selected, and its characteristics can be modified including, the name displayed on the grid, for example, how it fits into the task grid's icon, the description that appears in reports, a phrase used to describe the word to voice recognition logic utilized in the system, the McMAID category, a drop-down list displayed, and/or whether it has billable events associated with it.

FIGS. 17 and 19-29 are exemplary illustrations of a screen (or portions thereof) that provide functionality associated with Code Recordation.

FIG. 30 shows a screen section that is only visible for Run Report Codes.

FIGS. 31-39 are exemplary illustrations of a screen (or portions thereof) that provide functionality associated with Code Recordation.

FIGS. 41-55 are exemplary illustrations of a screen (or portions thereof) that provide functionality associated with Code Analysis.

FIGS. 57-58 are exemplary illustrations of a screen (or portions thereof) that provide functionality associated with archiving a Code.

FIGS. 60-63F are exemplary illustrations of a screen (or portions thereof) that provide functionality associated with Benchmarking.

FIGS. 66-69 are exemplary illustrations of a screen (or portions thereof) that provide functionality associated with system functionality development.

FIGS. 71-73 are exemplary illustrations of a screen (or portions thereof) that provide functionality associated with task grid organization.

DETAILED DESCRIPTION

Figure 1:
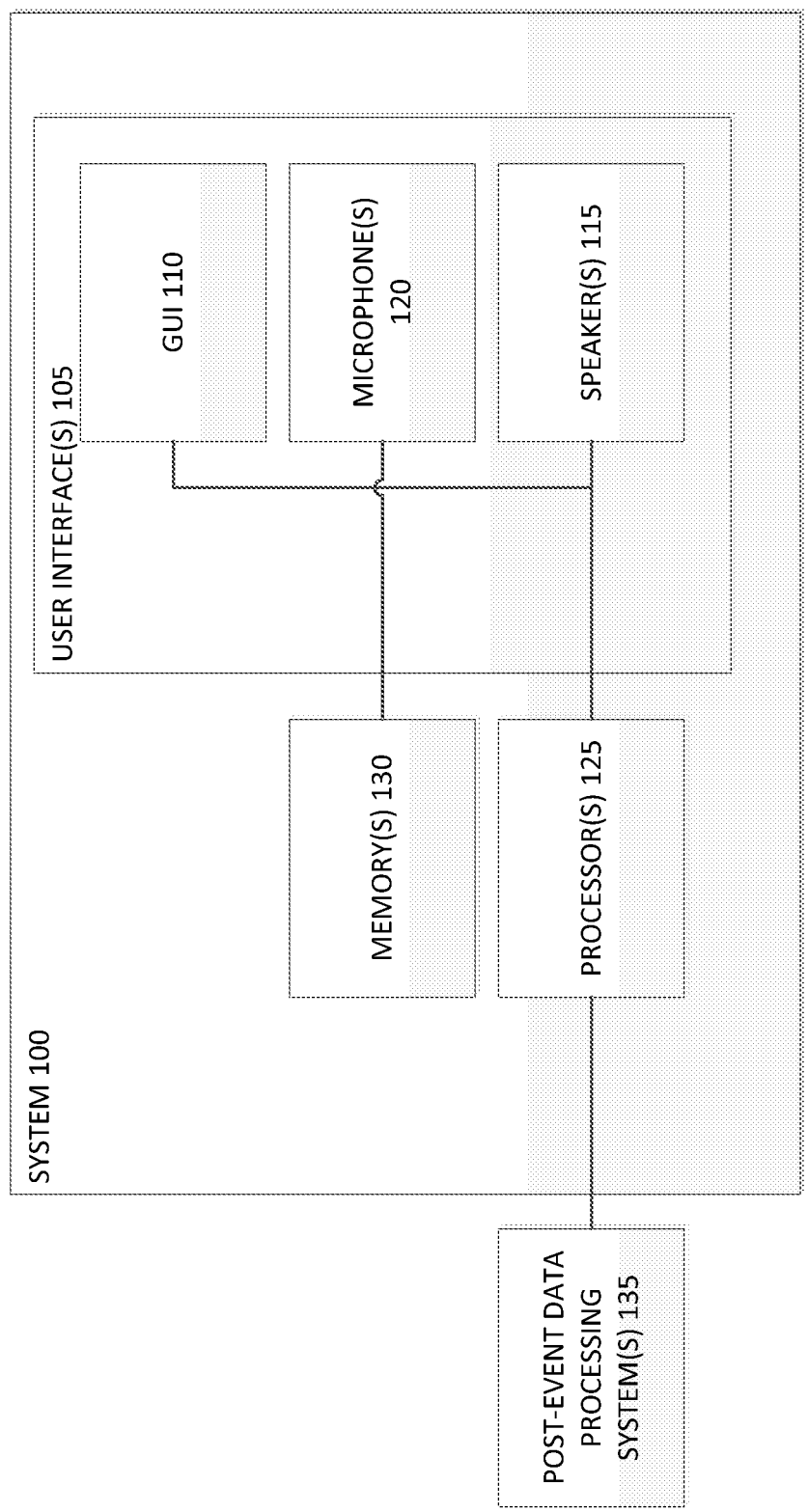
FIG. 1 illustrates an example of one hardware configuration that may be utilized to provide the disclosed embodiment functionality disclosed herein.

The description of disclosed embodiments is not intended to be limiting of the presently disclosed invention. To the contrary, those skilled in the art should appreciate that there are numerous variations and equivalents that may be employed without departing from the scope of the present invention. Those equivalents and variations are intended to be encompassed by the present invention.

In the following description of various invention embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

Moreover, it should be understood that various connections are set forth between elements in the following description; however, these connections in general, and, unless otherwise specified, may be either direct or indirect, either permanent or transitory, and either dedicated or shared, and that this specification is not intended to be limiting in this respect.

As explained above, in the precious moments available to save a person's life, documentation is often the least important task on anyone's mind; and in many instances documentation is done retrospectively. Even when done concurrently, documentation is seldom if ever utilized to discuss and assess the quality of the resuscitation effort; rather it is performed simply because documentation is a requirement. Thus, providing an accurate picture of the interventions and procedures employed and the timing of those procedures during treatment is very often problematic.

The American Heart Association (AHA), beginning in the mid 1960's, developed programs to improve the care of SCA victims. The education of laypersons, law officers and other first responders, Emergency Medical Service (EMS) providers and other medical personnel is performed using their programs. Management guidelines are revised by internationally recognized experts on a regular basis, and these are then translated into programs and treatment protocols that are used in educational efforts. Many millions have been trained and billions of dollars have been spent doing so. Resuscitation experts continue to teach the medical community what to do and why. Likewise, educational programs are responsible for training the medical community how to implement these directives. The understanding of the physiologic derangements operant during a cardiac arrest has improved tremendously over the years; and the advice given to the medical community is scientifically based.

However, despite these extensive advancements, the survival rates for victims of SCA have remained essentially unchanged over the last half century. What we have done to date to improve survival does not seem to be working: Improving scientifically-based treatment guidelines on a regular basis and requiring providers to attend educational sessions on a regular required periodic basis has not accomplished what we expected.

Therefore, if improvement is possible, the medical community must examine the way we educate individuals who treat SCA victims. A reasonable starting point is to query what is it that thwarts the ability to train competent responders. Indeed, education is crucial in the process of developing competence; however, what occurs after training is often more determinative of the degree and duration of a responder's competence.

Considering the conventional education of potential responders, an objective evaluation of performance for the resuscitation effort they participated in is seldom performed. Whether the patient lives or dies, there is no impetus to challenge the assumption that the interventions performed were sufficient, appropriate and that treatment was optimal. In the absence of such feedback and education, providers are at risk of continuing to deliver what may well be suboptimal care.

Likewise, the conventional training educational situation is similarly handicapped—subjective assessments of performance are fickle and often unreliable; individuals may pass a resuscitation training course and yet be sub optimally prepared for a real-life event.

To address this shortcoming, and others, disclosed embodiments have been developed and designed to provide an objective appraisal of the overall management of a cardiac arrest. The following explanation presents a simplified summary in order to provide a basic understanding of some aspects of various disclosed embodiments.

Disclosed embodiments are directed to enabling the ability to record and analyze the activities performed when treating an individual (real or simulated) with a cardiac arrest; and to present the results of that analysis for immediate feedback to the involved practitioners. In accordance with at least one embodiment, a system and equipment are provided that enable real-time feedback for personnel responding to cardiac arrest while an arrest is ongoing.

To provide an explanation of context and the deficiencies of conventional approaches to cardiac arrest event training and documentation, it should be understood that, conventionally, the recording of actions performed during a cardiac arrest is most often done solely for the purpose of documentation. Moreover, the accuracy of such documentation varies considerably—especially regarding the timing of events during a cardiac event. Most real-life cardiac events are documented using paper and pen; and the resulting documentation record is either saved as written or it is simply used to create a more structured report at a later time.

Conventionally, some computer devices are available that provide documentation information (almost exclusively used in retrospective reviews); and some even provide real time prompts regarding the quality of resuscitation interventions. However, the scope of their information and advice is limited to a small select subset of interventions performed.

To the contrary, the presently disclosed embodiments not only provide the ability to document an extensive set of events, in particular, with improved timing accuracy, but also to provide immediate and objective feedback to those participating in treatment of the cardiac arrest event, something that is not possible with conventional documentation technology or methodologies.

In accordance with disclosed embodiments, a system, equipment and methodologies are provided that record event data and other relevant data that enable objective analysis of a cardiac event and the care administered to a victim of that cardiac event. Thus, to best understand the functionality required to analyze cardiac arrest management, a brief explanation of the various types of cardiac arrests is necessary.

Preliminarily, however, it should be understood that disclosed embodiments are explained with reference to cardiac arrest events, which include events pertaining to the diagnosing, treatment and monitoring of a patient having a cardiac arrest event. In the medical community, such cardiac arrest events are also referred to colloquially as "codes." In the presently disclosed description of the disclosed embodiments, the term "Code" refers to a sequence of screens containing task and event data displayed on a Grid for selection by a user to record the occurrence of such tasks and events. Thus, all types of cardiac arrest events have a "Code" screen that displays events that may occur during the resuscitation process for a patient. As explained herein, the inventive system, equipment and methodologies may be used to record, analyze and generate reports regarding the tasks events that occur during a Code.

Cardiac arrests, as defined within the disclosed embodiments, can be categorized into four code-types: Real, Mock, Testing or Run Report.

The first category, Real, pertains to Codes involving a real person in a variety of settings (e.g., a hospital ward, an emergency department, an ambulance, etc.) where real time recording of relevant task performance and events is possible and valuable. Events that preceded initial recording can be memorialized; the retrospective timing of events (e.g., in reports) can be adjusted to the actual time of the start of a Code. Most often the protocols that guide responders, which are used to analyze performance, are known prior to a cardiac arrest event.

Therefore, in accordance with at least one disclosed embodiment, the system, equipment and methodologies may optionally enable the ability to pre-program protocols by an Administrator. However, it should be understood that the disclosed embodiments may be functional to perform, recordation, analysis, feedback, training, and post event processing without reference to, or use of, protocol data.

An Administrator is a personnel member who may be tasked with and/or trained to set up this cardiac event support system, equipment and methodologies to address particular local needs. Thus, the Administrator may make modifications to treatment protocols, event descriptions (e.g., words used in selecting and reporting events that have been recorded), and benchmarks (used to judge adequacy of performance), as explained herein. Multiple sets of treatment pre-code events, protocols and benchmarks may be developed by Administrators and may be specific to codes developed for facilities and departments. Additionally, specific sets of pre-code events and treatment protocols may be designated for use when a Code is being recorded. The second code category, Mock code, pertains to scenarios that mimic a real Code but wherein recording of all events is possible, including delays in arrival of equipment used to treat a cardiac arrest event. Protocols and equipment availability may be known beforehand. Likewise, the onset of a Mock Code may be known and, therefore, times (e.g., time stamps) recorded using the disclosed system, equipment and methodologies may not need to be adjusted (e.g., appended, as discussed herein). In Mock Codes, recording of details regarding tasks and event in a cardiac arrest event may be performed in real time.

The third code category, Testing, is similar to a Mock Code in that it is a structured training scenario, but all equipment is available; thus, arrival times for necessary equipment to treat the cardiac arrest event may not be tested. Likewise, onset of the cardiac arrest is known and recording is real time.

The fourth code category, Run Report, pertains to the entry of data in retrospect from various sources that are record in a "Report". Protocols may be assumed to exist.

As mentioned above, the disclosed embodiments, the system, equipment and methodologies provided in accordance with the disclosed embodiments may be utilized by an Administrator who is tasked with setting up the system, equipment and methodologies for use by other personnel, for example, Recorders and Developers.

A Recorder is a personnel member who is tasked with both selecting a code-type at the time of a Code and performing the actual recording of data for the cardiac arrest event. A Recorder may only be required to decide the code-type that is to be processed prior to using the equipment to begin recording documentation. As explained herein, recording may be accomplished using a Graphical User Interface (GUI) that may include a plurality of touch screens that enable the Recorder to document task and event data during the cardiac arrest event.

Utilizing the computer interface that displays such a GUI, tasks may be presented on a grid, as explained in detail herein, and can be recorded by the Recorder interacting with the displayed information to select options, input information, etc., by interacting with the computer interface physically, e.g., through mouse clicks, taps on a screen etc., or through voice recognition technology.

Thus, it should be understood that, although the system may be provided in a number of different hardware contexts, the disclosed embodiments may be implemented (FIG. 1) using a generalized or special purpose computer system 100 that may run software which provides the functionality disclosed herein. Thus, that system 100 may include one or more computer user interfaces 105, with which personnel (e.g., Administrators, Recorders, and Developers) may interact via a Graphical User Interface (GUI) 110 and/or voice recognition technology (the technology also being incorporated in software running on processor(s)) via at least one speaker 115 (for receiving output from the system) and at least one microphone 120 (for providing input to the system). The system functionality may be provided via software running on one or more processors 125 that may be proximately incorporated into the one or more computers (e.g., via a computer Tablet or other computing device) or may be running on processors 125 that may be remote from the user interface(s) 105 but connected thereto for communication and control. Additionally, the software may be similarly stored in memory 130 proximate or remote from the user interface(s) 105 but accessible from the user interface(s) 105; similarly, the data generated by the system may be archived or stored in memory 130 or another memory. That memory 130 may be accessible by other post-event data processing systems 135, e.g., training software and systems, feedback systems, accreditation systems, accounting systems, inventory systems, billing systems, etc., to provided data to those systems for post cardiac event processing.

Using the equipment, event occurrence may be recorded in connection with their respective times (e.g., as indicated by a time stamp) to provide effective recordation and documentation of a cardiac arrest event. As explained herein, time stamps generated by the system may be corrected if necessary; both during and after a preliminary analysis.

A program developer is a personnel member who may be called upon to make custom adjustments to the displayed content in the GUI. It should be understood that the content displayed on the GUI, e.g., the display of tasks, is dynamic; thus, only those tasks reflecting the current state of care for the cardiac event may be displayed using the GUI. Two examples of the content are shown in FIGS. 2-3.

Figure 2:
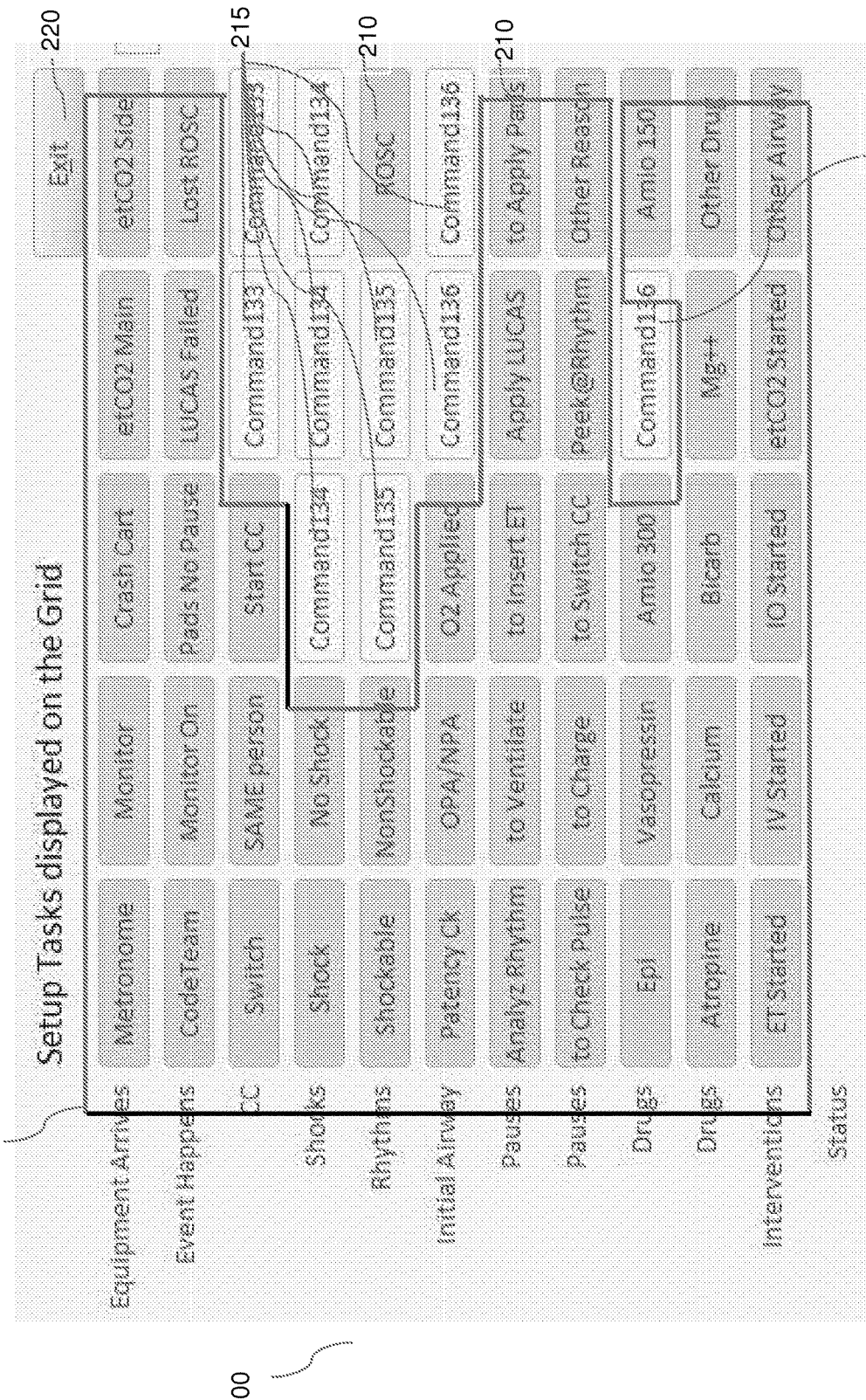
FIG. 2 illustrates one example of a form used to arrange the tasks on a grid in the GUI provided in accordance with at least one disclosed embodiment.
Figure 3:
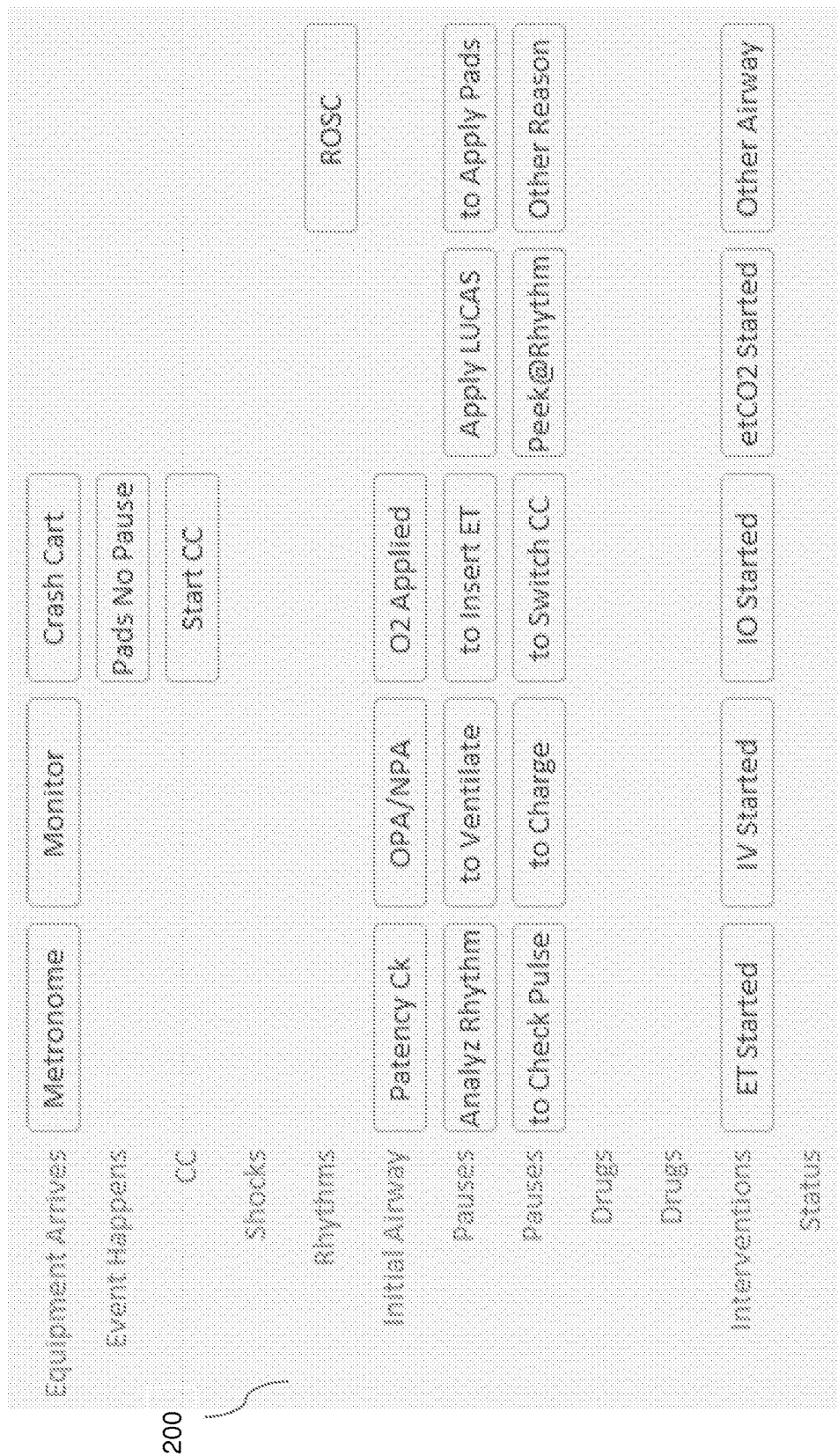
FIG. 3 includes a depiction of a screen shot which is exemplary of the GUI displayed on the equipment during a cardiac arrest event and what a Recorder might see when documenting Code tasks during that event.

As shown in FIG. 2, the content may include a task grid 200 that includes an array of icons that represent actions and events that occur during a Code, i.e., tasks. The length of a task phrase displayed in the icons (i.e., a word) is limited by the space available on the icons themselves. Longer, more descriptive, phrases may be associated with each word; such phrases may be used in lists of tasks performed in various screens output on the GUI. As explained above, words and the phrases used to describe them may be customized by the program Administrators.

As shown in FIG. 2, all of the tasks in 210 may be available for selection by a Recorder. There are no tasks assigned to the 215 icons. The grid 200 may also include an exit icon, which may be
selected to trigger display of a higher order menu screen discussed herein. FIG. 2 is a screen illustrating a form used to arrange the tasks on a grid in the GUI provided on the system.

However, program logic limits the tasks displayed on the grid in a context-sensitive manner. For example, in FIG. 3 no drugs are displayed because an intravenous access has not been established. This screen shot is exemplary of the GUI displayed on the equipment during a cardiac arrest event and what a Recorder might see when documenting Code tasks during that event.

Table 1 below provides an illustrative example of the Words that may be listed in the icons that may be included in the GUI and the associated cardiac arrest event task.

TABLE 1

| ButtonName | ReportName |
| --- | --- |
| A Fib | Rhythm: Atrial Fibrillation |
| All Clear | Cleared before Shocking |
| Amio 150 | Amiodarone 150 mg |
| Amio 300 | Amiodarone 3OOmg |
| Analyz Rhythm | Pause - Analyze Rhythm |
| Apply LUCAS | Start LUCAS application |
| Apply O2 | O2 Applied |
| Apply Pads | Apply Pads |
| Assigns Roles | Team Leader: Assigns Roles |
| Asystole | Rhythm: Asystole |
| Atropine | Atropine |
| Bicarb | Sodium Bicarbonate |
| Calcium | Calcium |
| Call for Help | Called for Help |
| Charge | Pause - Charging |
| Charge Done | Charge Completed |
| Check Pulse | Pause - Pulse Check |
| Code Finished | Code Phase Completed |
| CodeTeam | CodeTeam Arrives |
| Crash Cart | Crash Cart Arrived |
| D50 | D50 |
| Dopamine | Dopamine |
| Dose Atropine | Discussed Atropine Dosage |
| EKG Done | 12 Lead Performed |
| Epi | Epinephrine |
| etC02 Main | etC02 Mainstream Used |
| etC02 Side | etC02 Sidestream Used |
| Glucagon | Glucagon |
| Heard Page | The Overhead Page was heard |
| HypoThermia | Discussed Hypothermia |
| Is Captain | Team Leader: Takes Charge |
| IV Done | IV Running |
| IV Failed | IV Failed |
| IV Started | IV Started |
| Ketamine | Ketamine |
| Know Is PNB | PNB Recognized |
| Knows ROSC | ROSC Recognized |
| Lab Tests Done | Ordered Lab tests |
| Leads On Okay | Monitor Leads: Appropriately Positioned |
| Lidocaine | Lidocane |
| Lost ROSC | Lost ROSC |
| LUCAS Failed | LUCAS Failed |
| Manual Unit | Using Manual Defibrillator |
| Mark | *** Mark*** |
| Metronome | Metronome Started |
| Mg++ | Magnesium Sulfate |
| Mobitz 2 | Rhythm: Mobitz Type 2 |
| Monitor Here | Monitor Arrived |
| No Shock | Pause - No Shock delivered |
| NonShockable | Non-Shockable Rhythm |
| 02 Sat Done | 02 Sat Determined |
| OPA | OPA/NPA Inserted |
| Other Airway | Start Other Airway insertion |
| Other Drugs | Other Drug |
| Other Reason | Pause - Other Reason |
| PaceMaker | Pacemaker Applied |
| Pacer mA | PaceMaker: mA Set |
| Pacer Rate | PaceMaker: Rate Set |
| Pads Failed | Pads Failed |
| Patency | Patency Checked |
| Pause 4 ET | Pause for ET Insertion Ended |
| Pause 4 ET | Pause - ET Insertion |
| PEA | Rhythm: PEA |
| Peek@Rhythm | Pause - Peek at Rhythm |
| Pulseless VT | Rhythm: Pulseless Ventricular Tachycardia |
| Put On Leads | Monitor Leads: Applied |
| Read Rhythm | Analyzes Rhythm |
| ROSC | Pause - ROSC |

TABLE 1-continued

| ButtonName | ReportName |
| --- | --- |
| SAME person | SAME person |
| Shock | Pause - Shock delivered |
| Shockable | Shockable Rhythm |
| Sinus Brady | Rhythm: Sinus Bradycardia |
| Start CC | Start CC |
| Start ET | Start ET insertion |
| Start etC02 | Start etC02 |
| Start IO | Start IO insertion |
| Start IV | Start IV insertion |
| Start IV | Started IV | when the code is initiated and automatically record their associated task(s), even though they do not appear on the GUI. These pre-code tasks may be used by the recordation and analytics software incorporated in the disclosed embodiments to provide the GUI to control what is displayed on the GUI for the Recorder to interact with. They are listed in Table 2.

Protocols define what responders should adhere to during their management of the cardiac arrest event. The developer can customize them during the process of creating a code. They can then be included as a benchmark when analysis is performed. Protocols available are also listed in Table 2.

TABLE 2

| Pre-Code Tasks | Protocols |
| --- | --- |
| AED used@ start of recording | Limit the #of Epi Doses allowed |
| CC Ongoing@ start of recording | Limit the #of Vasopressin Doses allowed |
| Combitube in place @ start of recording | Metronome in Defibrillator |
| Crash Cart present before Start of Recording | Using AHA time for 1st Dose of Amiodarone |
| etC02 in place @ start of recording | Using AED |
| Initial Airway done @ start of recording | Using Amiodarone |
| IO in place @ start of recording | Using CCR |
| IV in place @ start of recording | Using CPR |
| LUCAS ON @ start of recording | Using Crash Cart |
| Manual defibrillator@ start of recording | Using Early Invasive Airway if Initially non-Shockable |
| Metronome started @ start of recording | Using Epinephrine |
| Monitor ON @start of recording | Using etC02 |
| | Using IO |
| | Using LUCAS |
| | Using Manual Defibrillator |
| | Using Max Joules for Shocks |
| | Using Metronome |
| | Using See-Through Rhythm Analysis |
| | Using Supraglottic Airway |
| | Using Vasopressin |

TABLE 1-continued

| ButtonName | ReportName |
| --- | --- |
| Start Monitor | Monitor Turned On |
| Start 02 | 02 Applied |
| Start Transport | Start Transporting |
| Stop Transport | Transport Stopped |
| SuccX | Succinylcholine |
| SVT | Rhythm: SVT |
| Switch CC | Switch CC |
| Talk Airway | Discussed Airway Options |
| Talk Card-Vert | Discussed use of Cardioversion |
| Talk Epi | Discussed use of IV Epi |
| Talk etC02 | Discussed use of etC02 |
| Use Atropine | Discussed Use of Atropine |
| Using AED | Using AED |
| V Fib | Rhythm: V Fib |
| Vasopressin | Vasopressin |
| Ventilate | Pause - Ventilations |
| Versed | Versed |
| VS Taken | VS Taken |
| Watches Team | Team Leader: Assess performance |

Figure 36:
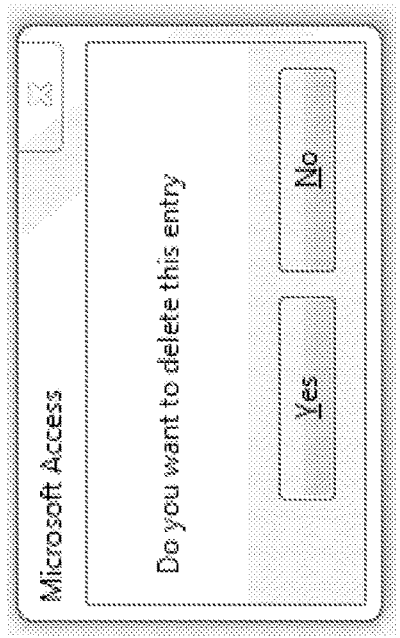

The use of show-hide logic enables the system, equipment and methodologies to be configured to operate in a once-done-it-disappears mode of operation. For example, monitor arrival may be a one-time event during a Code; thus, once the Recorder selects the associated icon on the task grid, it is no longer displayed (discussed below with regard to FIG. 36).

Likewise, there may be tasks that occurred before the code started and are not observed by the Recorder. These are termed pre-code tasks and are listed in Table 2. The developer can customize these for each code. They are triggered These pre-code tasks may be used by the recordation and analytics software incorporated in the disclosed embodiments to provide the GUI to control what is displayed on the GUI for the Recorder to interact with. Additionally, these pre-code tasks may also define many aspects of the logic used in analyzing the details and actions that occur during a Code.

However, it should also be understood that, in accordance with at least one disclosed embodiment, the system, equipment and methodologies may optionally be configured to not use pre-code or protocol data. Thus, it should be understood that the disclosed embodiments may be functional to perform, recordation, analysis, feedback, training, and post event processing without reference to, or use of, pre-code or protocol data.

Analysis of details and actions during a Code may be available immediately. Analysis data and results may be displayed on the GUI and/or one or more monitors. For example, analysis data and results may be projected for immediate review with personnel working on the corresponding cardiac arrest event.

Additionally, reports including a list of events recorded during the code and the results of the performance analysis may be printed to one or more local or remote printers for immediate or subsequent use, e.g., for analysis of materials and medicine used on the patient during the cardiac arrest event. Generation and organization of reports is explained herein.

A customizable set of benchmarks may be set up and used to analyze the event details. This set of benchmarks may be set and stored when the Code is archived. They can be modified during analyses, if deemed appropriate, but cannot be changed after the code is archived. Thus, re-analysis, either immediately or subsequently at a later date, is enabled. Moreover, during re-analysis, the system enables the use and application of a different set of benchmarks to be used to analyze the cardiac arrest event data.

All data generated during cardiac arrest events may also be archived so as to be stored in a meaningful and accessible way for subsequent review at a later date. The information relevant to the type of Code (e.g. physician and registered nurse in charge, etc.) may be collected and stored and that information may be used to sort the archived data. In this way, the data is generated in real time during a cardiac arrest event and is accessible and comparable with data from other events that share common characteristics.

The pre-code, protocol and benchmark used during a Code may be saved along with the tasks performed during the Code. As a result, the presentation of information using the equipment, system and methodologies may be further improved on an ongoing basis to ensure that the Recorder can effectively utilize the GUI to record data and memorialize details and actions that occur during Codes.

In accordance with at least one disclosed embodiment, patient identifying information is NOT collected; therefore the data from archived Codes for that disclosed embodiment may also be made available for research purposes.

The archived data may be stored on the user equipment initially and/or stored on memory at a centralized location within a particular department or facility to ensure that the data is maintained in an uncorrupted and secure manner and is accessible for re-analysis, compilation with other data and use by other computer systems provided within a facility, e.g., for inventory control in order to automatically order depleted supplies, for billing purposes in order to accurately charge for used materials and medicine, for liability management in order to track what batches of supplies such as medicine are used on what patients to track and minimize the risk of tainted supplies. Data (with patient-specific information removed) may also be archived in a centralized database that collects data from many users. In doing so a research database is created and becomes useful as long as the terminology used to define events recorded can be standardized.

Disclosed embodiments may be utilized in conjunction or be compatible with the McMAID concept. See Kellum M J. Improving performance of emergency medical services personnel during resuscitation of cardiac arrest patients: the McMAID approach. Curr Opin Crit Care 2009; 15(3):216-220, incorporated by reference in its entirety herein. The McMAID concept was originally developed to aid in defining sets of tasks that can be delegated to and readily performed by single responders. It also prioritized the order in which these tasks should be performed. The acronym stands for the following: Metronome, Chest compressions (CC), Monitor (defibrillator), Airway, IV-IO, Drugs. In the display of analysis results, two additions to this sequence have been made for pauses and CC Summary. The nature of these results and how they may be analyzed relative to benchmarking and real-time prompting during a code is explained herein.

Presently disclosed embodiments can extend that usage to provide guidelines for the order in which tasks are to be performed during a Code. Thus, McMAID and similar protocols may be used to dictate the order in which tasks and/or results may be presented to a Recorder on the GUI. They may also be used to prompt the Recorder regarding when tasks should be performed. Here, again the use of show-hide logic enables the system and equipment to be configured to operate in a once-done-it-disappears/new-icons-are-shown mode of operation, thereby minimizing the number of options available for data recording to reduce potential data entry errors.

Use of protocols such as McMAID may also provide benchmarking logic that may be used during objective analysis of the details and/or results of tasks performed during a Code. In this way, the disclosed embodiments enable objective analysis of the details and results of tasks and events occurring during a Code, which may be performed with reference to and comparison with various benchmarks discussed herein. Accordingly, such data may be analyzed by looking at the occurrence(s) of each task and determining whether it was performed within an acceptable time frame and appropriately sequenced. Thus, benchmarks may define the limits of acceptability.

As alluded to above, benchmarks utilized by the system may be modified by the Administrator; but unlike pre-code sets, which may be specific to each code-type, a set of benchmarks may be used for all code-types. Multiple sets of benchmarks may be developed; however, one set of benchmarks may be designated as a default set prior to the system and equipment being using to process any Code.

Benchmarks may be grouped using McMAID logic, both during the design of a benchmark set and during display of results of an analysis. One set of available benchmarks is illustrated in Table 3. "Sec" refers to the maximum acceptable number of seconds between the two events in the benchmark.

TABLE 3

| Sec | McMAID - Category | Benchmark Name |
| --- | --- | --- |
| 15 | Metronome | Metronome - To Start after Starting CC |
| 150 | Chest Compressions | CC - Duration - Max |
| 100 | Chest Compressions | CC - Duration - Min |
| 75 | Chest Compressions | CC - Time between Switching Compressors |
| 20 | Chest Compressions | Start CC - after Prior Rhythm Analysis - AED |
| 8 | Chest Compressions | Start CC - after Prior Rhythm Analysis - Manual |
| 8 | Chest Compressions | Start CC - after Prior Rhythm detected |
| 3 | Chest Compressions | Start CC - after Prior Shock/NoShock |
| 20 | Chest Compressions | Start CC - after Start of Recording |
| 30 | Monitor - Defibrillator | Monitor - To Turn on after it's available |
| 5 | Monitor - Defibrillator | Pads - To apply - doing CCR |
| 10 | Monitor - Defibrillator | Pads - To apply - doing CPR |
| 10 | Monitor - Defibrillator | To Analyze Rhythm - AED |
| 5 | Monitor - Defibrillator | To Analyze Rhythm - Manual defibrillator |
| 15 | Monitor - Defibrillator | To Charge - using AED |
| 0 | Monitor - Defibrillator | To Charge - using CCR & Manual defibrillator |

TABLE 3-continued

| Sec | McMAID - Category | Benchmark Name |
|---|---|---|
| 10 | Monitor - Defibrillator | To Charge - using Manual defibrillator |
| 5 | Monitor - Defibrillator | To Shock - after Rhythm Analysis |
| 3 | Monitor - Defibrillator | To Shock - after Shockable Rhythm |
| 120 | Airway | Initial Airway - after Start of Recording |
| 120 | Airway | Initial Airway - after Start cc |
| 360 | Airway | Invasive airway - Earliest time after Initial Rhythm - Shockable |
| 390 | Airway | Invasive airway - Latest time after Initial Rhythm - Shockable |
| 30 | Airway | Invasive airway - Max time after Initial Rhythm - Non-Shockable |
| 30 | Airway | Max Time after Initially NonSockable to Start ET |
| 15 | Airway | Start Mainstream etC02 - after Invasive airway ready |
| 60 | Airway | Start Sidestream etc02 - after Start of Recording |
| 0 | Airway | To Ventilate if doing CCR |
| 5 | Airway | To Ventilate if doing CPR |
| 20 | IV-IO | Max time to Insert IO |
| 20 | IV-IO | Max time to Insert IV |
| 3 | Drugs | Max # of Epi doses allowed |
| 30 | Drugs | Max time 1st Amiodarone after Shockable Rhythm |
| 15 | Drugs | Max time 1st dose Epi after IV or IO ready |
| 30 | Drugs | Max time between 1st Epi and 1st Vasopressin |
| 660 | Drugs | Max time between 2nd and 1st Vasopressin doses |
| 300 | Drugs | Max time between Epidoses |
| 540 | Drugs | Min time between 2nd and 1st Vasopressin doses |
| 180 | Drugs | Min time between Epi doses |
| 0 | Pauses | Max pause - other reasons |
| 10 | Pauses | Max pause to apply LUCAS |
| 0 | Pauses | Max pause to do Pulse check - CCR |
| 10 | Pauses | Max pause to do Pulse check - CPR |
| 0 | Pauses | Max pause to insert ET - CCR |
| 10 | Pauses | Max pause to Insert ET - CPR |
| 0 | Pauses | Max Sec Allowed for Peek@Rhythm Pause |
| 60 | Pauses | Max time Crash cart arrval - after Start of Recording |

Figure 4:
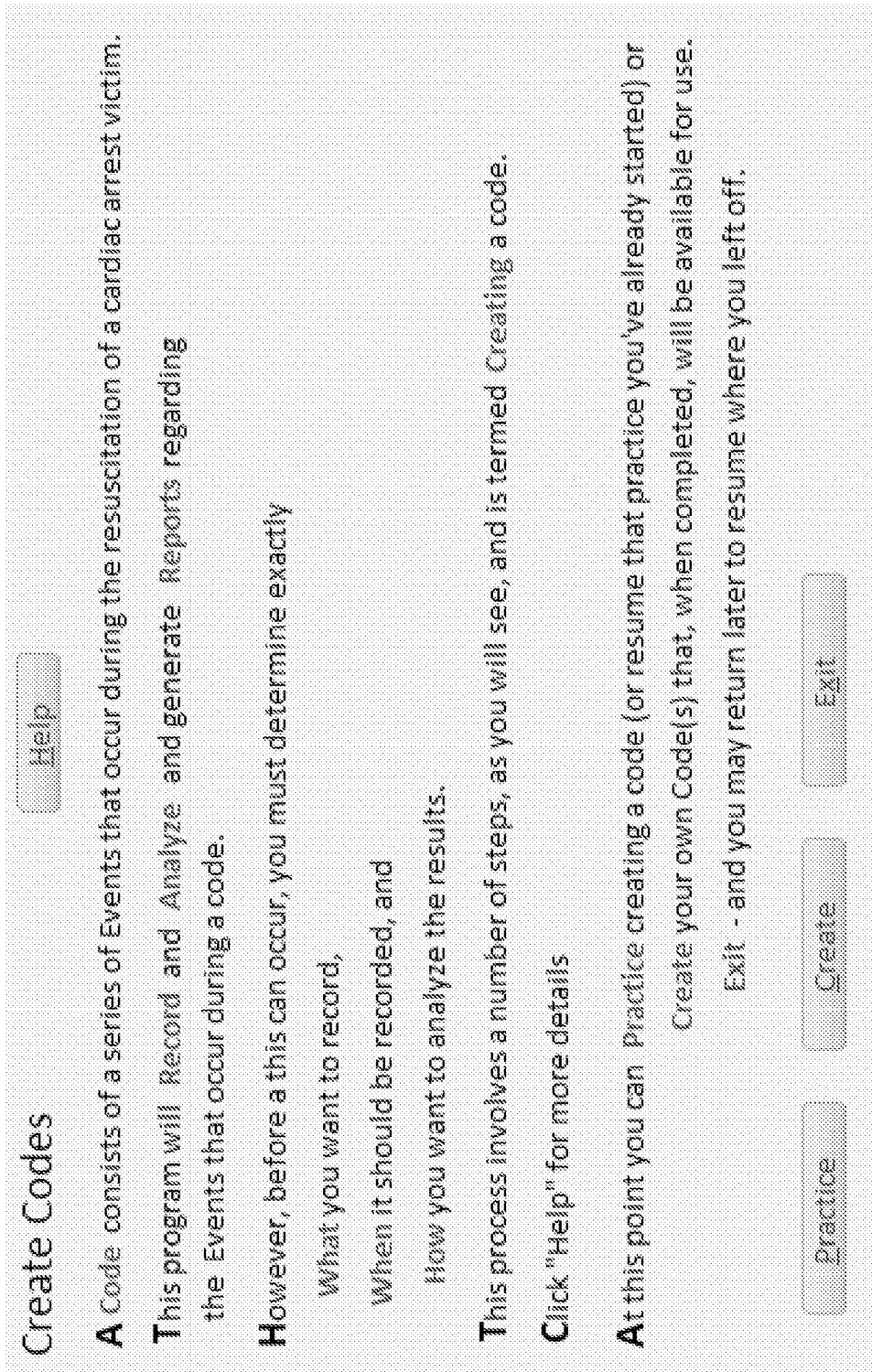
FIG. 4 illustrates one example of an introduction screen for creating new Codes in accordance with at least one disclosed embodiment.

In accordance with at least one embodiment, the system may provide flashing functionality, wherein an Administrator can define what events they want the Recorder to be reminded of during the various phrases of a Code. The logic may be linked to benchmarks explained below. Flashing, which may be optionally disabled by the recorder, involves remembering when a trigger event occurs and then warning the recorder (by blinking the target event) a specified interval before the target event is due according to its associated benchmark interval. When that interval has been reached, the target event is colored red and blinks As shown in FIG. 4, prior to use of the system by a Recorder, an Administrator must set up the Codes that will be used by the system. To this end, an Administrator may be presented with a screen that provides instructions for creating a new Code to be used by the system and equipment. As explained on the introduction screen for creating new Codes in FIG. 4, the system and equipment may record, analyze and generate reports regarding the tasks and events that occur during a Code. However, prior to recordation, the Administrator must exactly determine what needs to be recorded, when it should be recorded and how the results of that recordation should be analyzed. This process involves a number of operations and may include actual creation of a Code that may be used in the system, i.e., creation, or practicing creation of a Code (e.g., to enable the user to train on how to use the system and set up a system configuration that is effective).

Figure 4A:
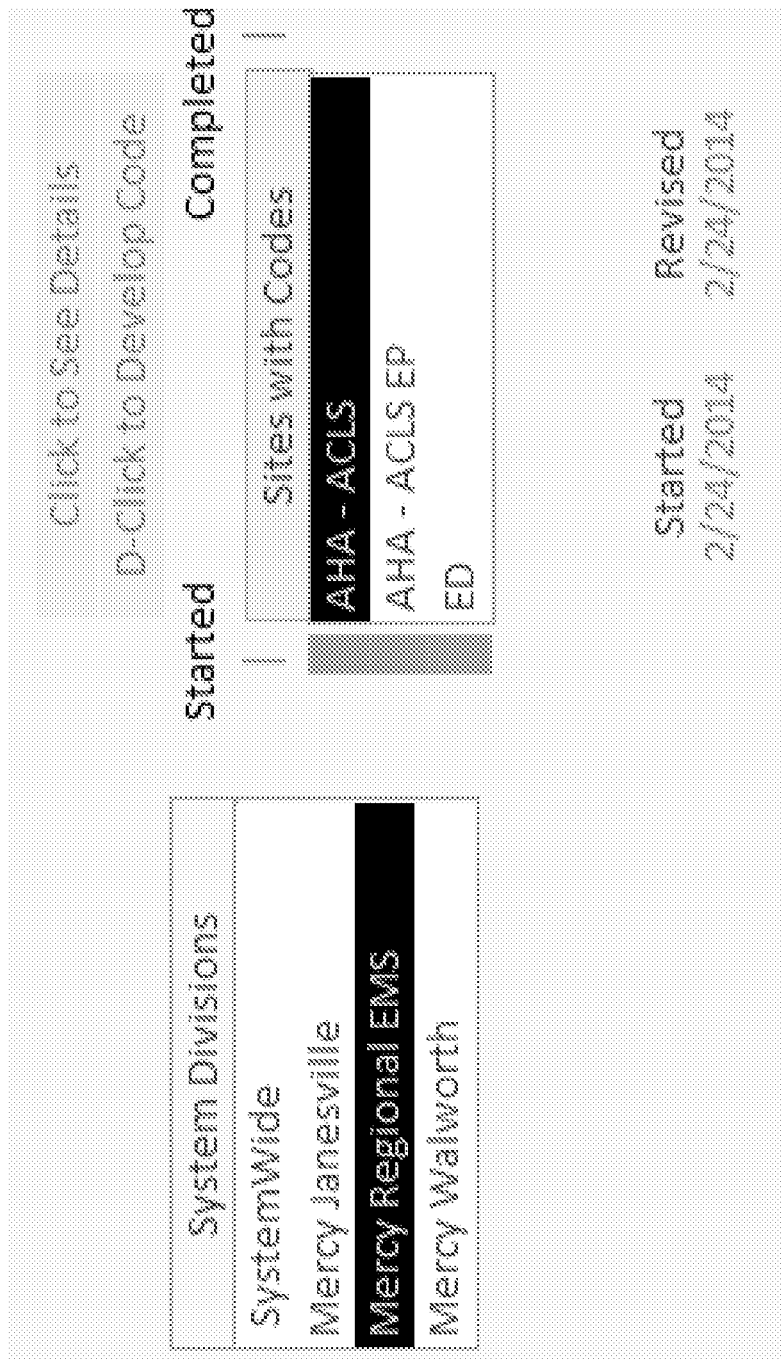
Figure 4D:
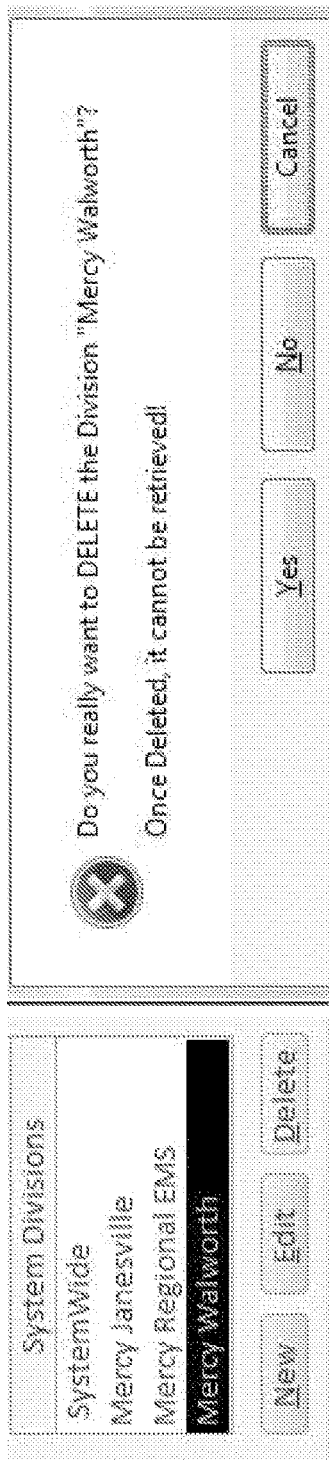

Customization may be enabled using a hierarchy of format—division—site, which may allow allows Administrators to develop system-wide Codes and then modify them accordingly to meet local (division/site) needs. For example, all system-wide Codes for the format may be displayed. When a specific code is selected, the dates when it was started and last revised may be displayed—as shown in FIG. 4A. Likewise, new divisions can be added but duplicate names may not be allowed as shown in FIGS. 4B-4C. Additionally, existing divisions can be renamed or deleted as shown in FIG. 4D.

Figure 4E:
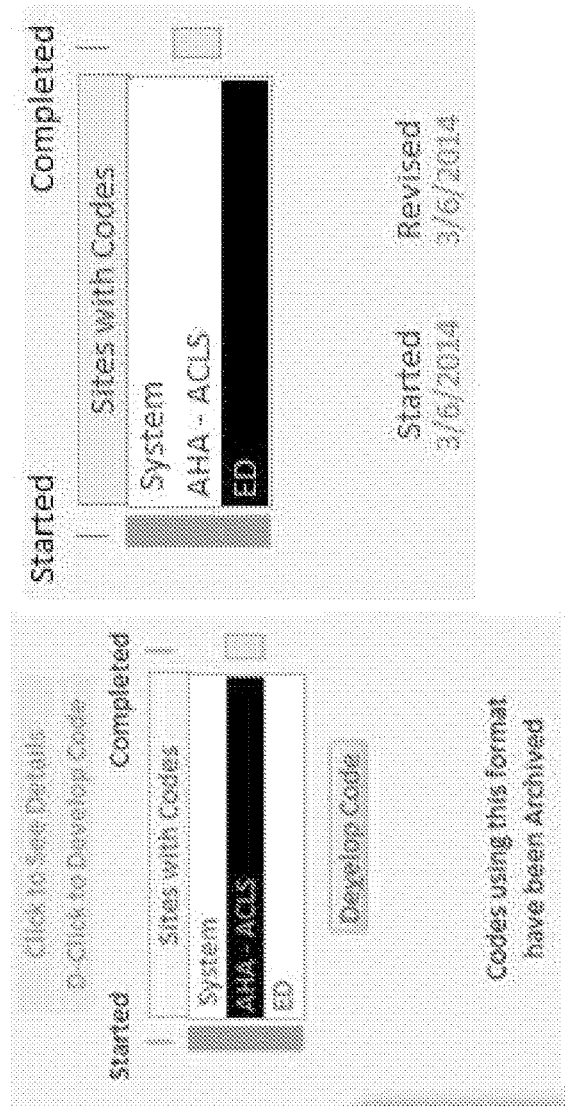
Figure 4F:
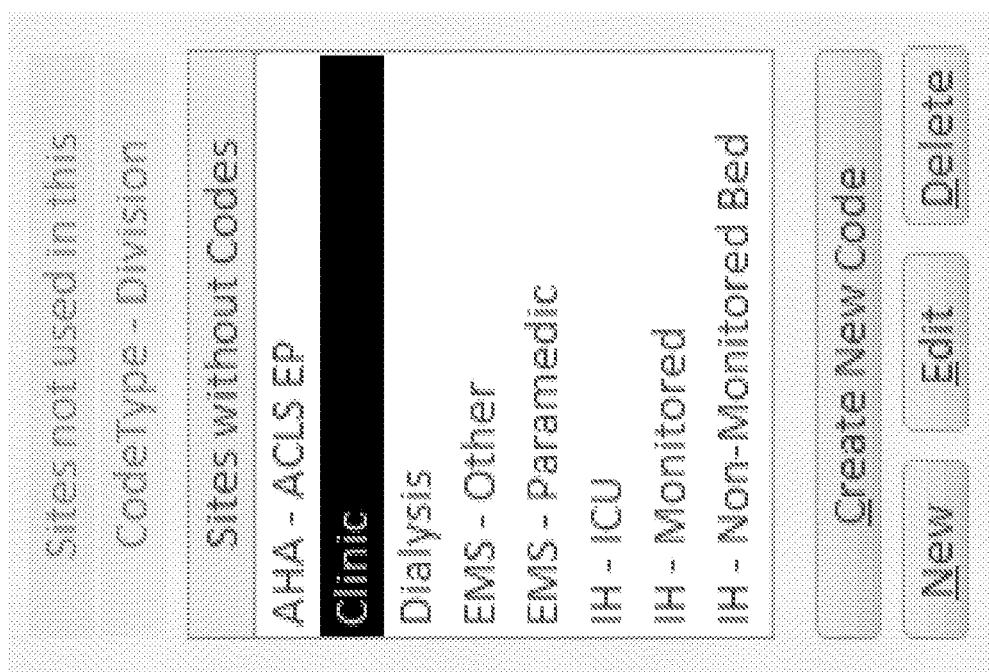

Selecting an existing Code then allows the Administrator to continue developing the Code or to copy it. If a Code has been run in the past, and therefore has archived data linked to it, its content cannot be modified—instead it can be copied and the original Code may be inactivated so that it no longer will show on the screen (as illustrated in FIG. 4E on the left). If the Code has not been completed, development can be continued. Finally, as shown in FIG. 4F, a Code for a new site can be developed, the site itself can be renamed, or the site can be deleted (but only if no Code has been attached to it).

Figure 5:
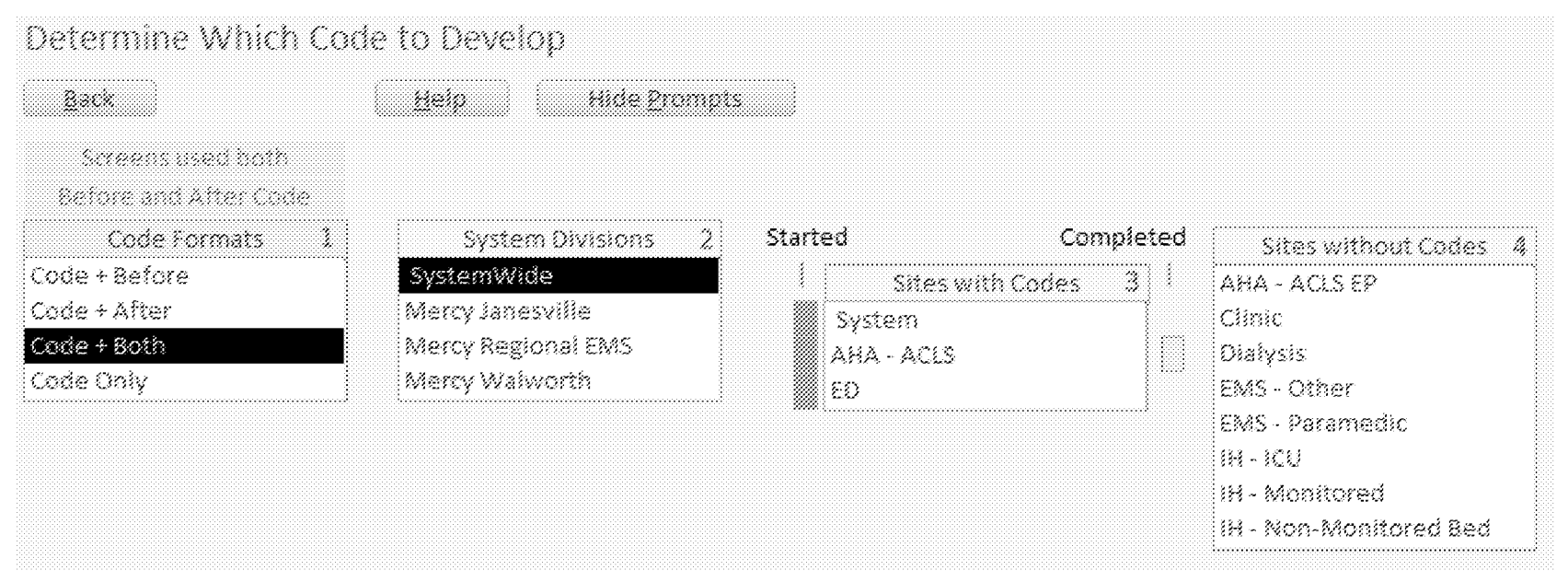

FIG. 5 illustrates another example of the Code Development screen(s) provided in accordance with the disclosed embodiments. By enabling the Administrator to develop a Code, the system and equipment enable users to customize the presentation of tasks and events for recordation by the Recorder. In doing so, the Administrator is able to ensure that the screen contents are user friendly for the Recorder. However, it should be understood that the need for customization must be weighed with the need for standardization so as to enable generated data to be useful outside the context of the disclosed system, equipment, Location and Recorder. For example, the generated data may be input into other data processing systems; as a result the data may need to be in a prescribed format for those systems' use. In other words, local definitions that are generated and understood by local users are valuable; however, if the Code data is to be archived and made available to other systems then standards would need to be available that enable meaningful comparisons, sorting and characterizations.

The Utstein criteria have been utilized for years by the resuscitation community in this regard. The Utstein criteria is a set of guidelines for uniform reporting of cardiac arrest.

The Utstein criteria, or Style, was first proposed for emergency medical services in 1991. The name derives from a 1990 conference of the European Society of Cardiology, the European Academy of Anesthesiology, the European Society for Intensive Care Medicine, and related national societies, held at the Utstein Abbey in Norway.

In accordance with at least one disclosed embodiment, a central dictionary may be maintained and be available to Administrators who then may add to or download events they want to include in their implementation. This maintains standards by assigning mother-identifiers to all events used by all users, which may then be included in archived data. Administrators can then rename events to fit their local dialect, as long as the nature of the event is unchanged. Similar logic may be utilized to transmit whole Codes that may be needed if a mother system develops and disseminates training Codes that are designed to meet standards of recognized expert agencies, e.g., the American Heart Association's Advanced Cardiac Life Support (AHA ACLS) that is periodically revised.

When the disclosed embodiments are used for training and evaluation, some training scenarios may contain additional events and tasks that need to be discussed or recognized by a trainee and performance evaluated. This process may occur before and/or after the actual resuscitation portion of a training code.

Figure 6:
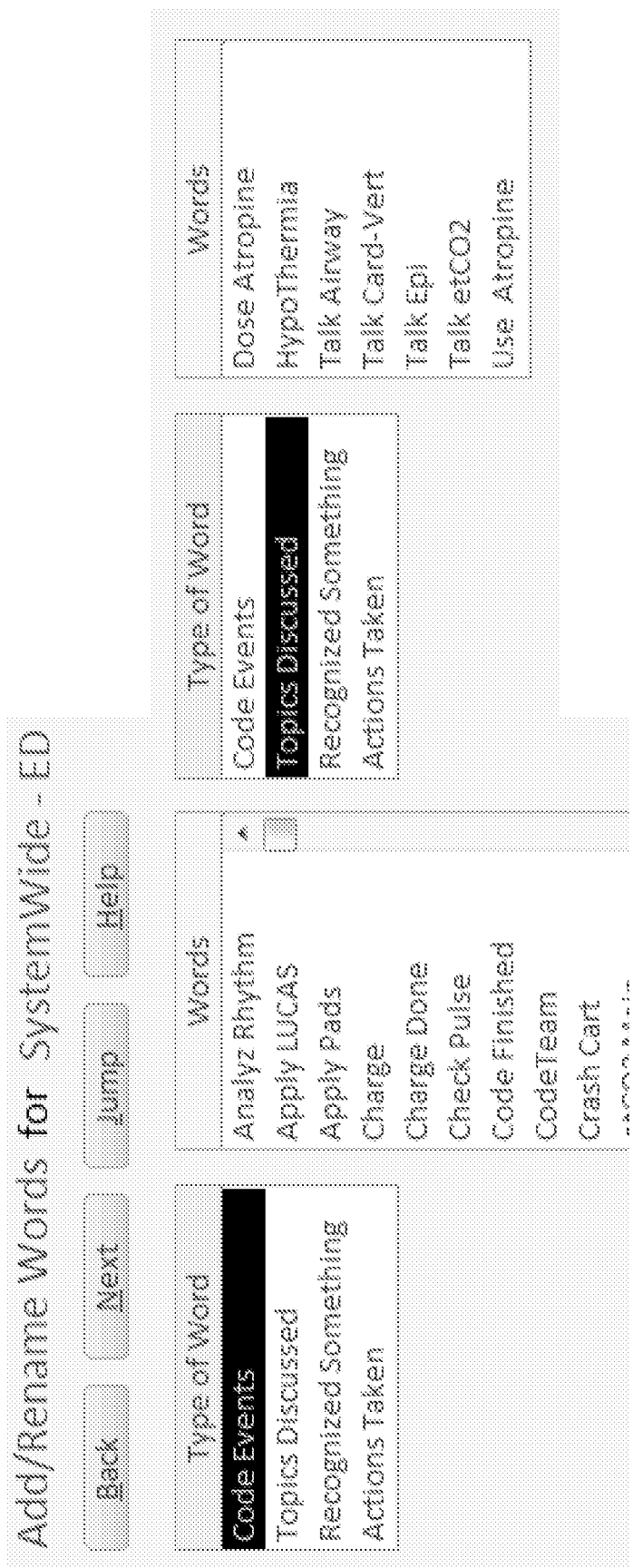

In order to simplify management of events (also referred to as words), the events may be divided into logical categories. For example, Code events may be those events that occur during the resuscitation effort. Others words that are utilized in the before and/or after the Code screens may include topics discussed, recognized things and actions taken. Thus, a screen may be organized around these categories, e.g., as illustrated in FIGS. 6 and 7, wherein a word category is selected and the terms associated with that category are displayed.

Figure 8:
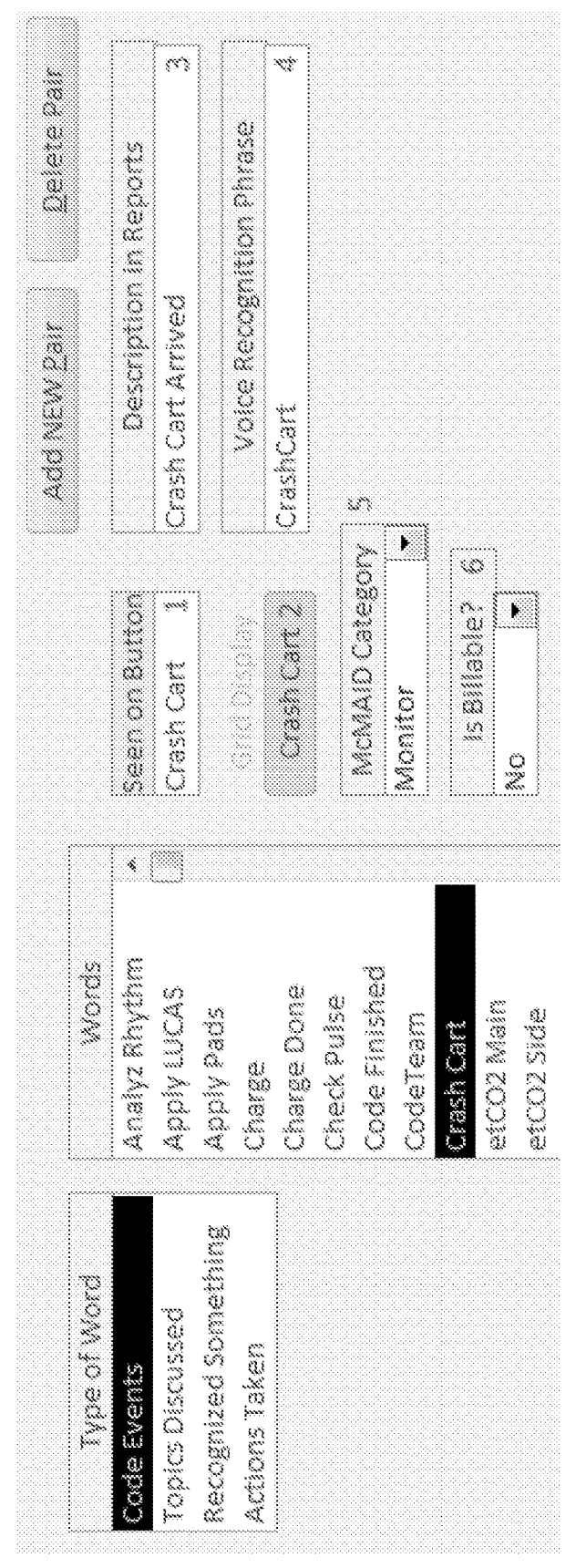
Figure 9:
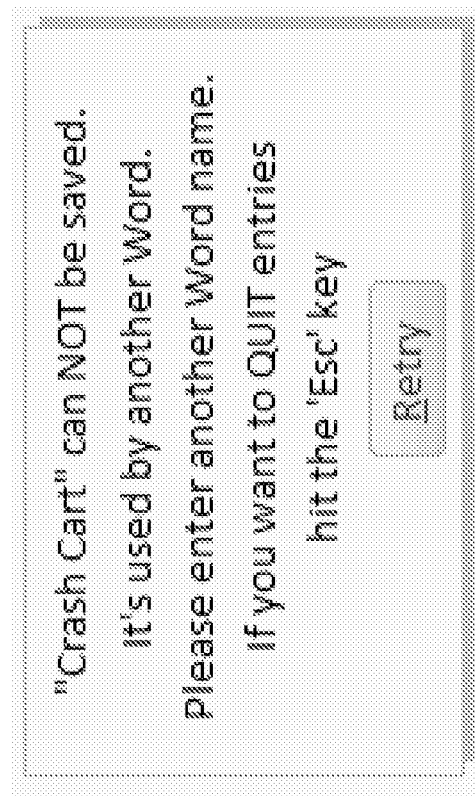
FIG. 9 illustrates details regarding when adding words, wherein duplicates may not be allowed and deletions may only be allowed if an event/word has not been utilized in an archived Code.

Moreover, as shown in FIG. 8, when a word is selected, its characteristics can be modified including, the name displayed on the grid, for example, how it fits into the task grid's icon, the description that appears in reports, a phrase used to describe the word to voice recognition logic utilized in the system, the McMAID category, (where a drop-down list displayed), and/or whether it is a billable events associated with it. Additionally, using this screen, the user may be presented with two options: add a new pair (icon name and description and associated properties) and/or delete an existing pair. When adding, duplicates may not be allowed and deletions may only be allowed if an event/word has not been utilized in an archived Code, e.g., see FIG. 9.

Figure 10:
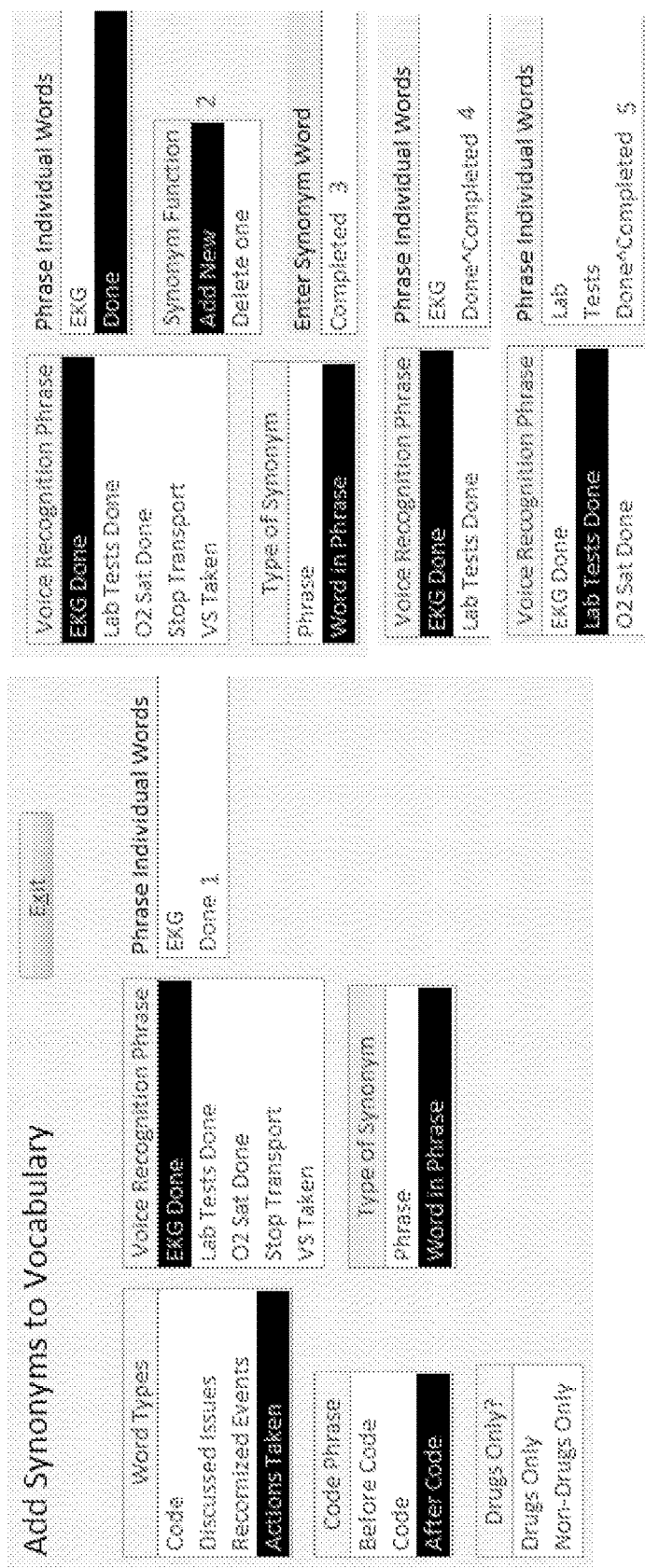
FIG. 10 provides an illustration of how synonyms may be utilized in accordance with the disclosed embodiments.

In accordance with at least one disclosed embodiment, a synonym database may be provided that enables linking of voice recognition technology to task recordation. Thus, a specific check on the uniqueness of voice recognition phrases may be performed. There may be, for example, two categories of synonyms: those for a single word and those for a phrase. Thus, words that exist in the vocabulary discussed above may be organized as above: by type and based on where, in the Codes' screen(s), the word appears (before, during, or after the Code). For example, as shown in FIG. 10, the word "completed" is used as a synonym for "done". The prompts concerning the term's use may not be shown; however, the prompts enable a user to change their mind and avoid duplicate entries. Once a word has been accepted, the word may appear in other phrases where the word "done" is used. The logic to implement this feature is similar when entering a relationship, e.g., type of synonym=phrase. Thus, the entered sequence of words may be linked to an event described in its voice recognition phrase.

This approach to synonyms enables increased utility when using Nuance's® voice recognition technology and interfacing with Microsoft® Access (and, in theory other Microsoft® based products). This is because Nuance® can only place its voice recognized words in a single window. Therefore, since multiple windows (screens) may be used in a code, a window may be dedicated to voice recognition. Words deposited in this dedicated window may then be processed to define a single specific event for recordation. In this way, it appears as it would be if it was selected in a current screen. It should be understood that this is merely one exemplary implementation and may be accompanied by a voice recording component that can be referenced to resolve incomplete recognitions.

Figure 11:
FIG. 11 provides an example of a Code Development screen of the GUI designed in accordance with the disclosed embodiments.

As mentioned above, pre-code events are particularly useful for canned training scenarios. However, in some disclosed embodiments, the ability of an Administrator to use pre-code events may impede accurate recording of real-life cardiac arrest events by improperly generalizing a setup existing before a Code begins. Accordingly, in accordance with at least one embodiment, selecting a recorded event by holding down an Alt/Ctrl/Shift key while clicking it may be used to indicate it happened before recording was begun. This approach may be utilized when recording the resuscitation of a real victim. Thus, turning to a more detailed discussion of how an Administrator may develop a Code, FIG. 11, discloses a Code Development screen of the GUI designed in accordance with the disclosed embodiments. As shown in FIG. 11, an Administrator or Developer is shown a list of required components and may proceed to a screen by double-clicking an item in the list. As can be seen in the example of FIG. 11, the Administrator has already completed add/edits words used, and protocols; however, the Administrator still needs to address benchmarks for analysis, flashing reminders in the Code, events occurring before the Code starts and drugs used. Whenever changes in one screen require revisiting another screen, the status indicator box is colored yellow and completion-status is revised to incomplete until the affected screen is revisited. Explanation is now provided of an exemplary, non-limiting configuration for the GUI and the associated software running on one or more servers.

Figure 12:
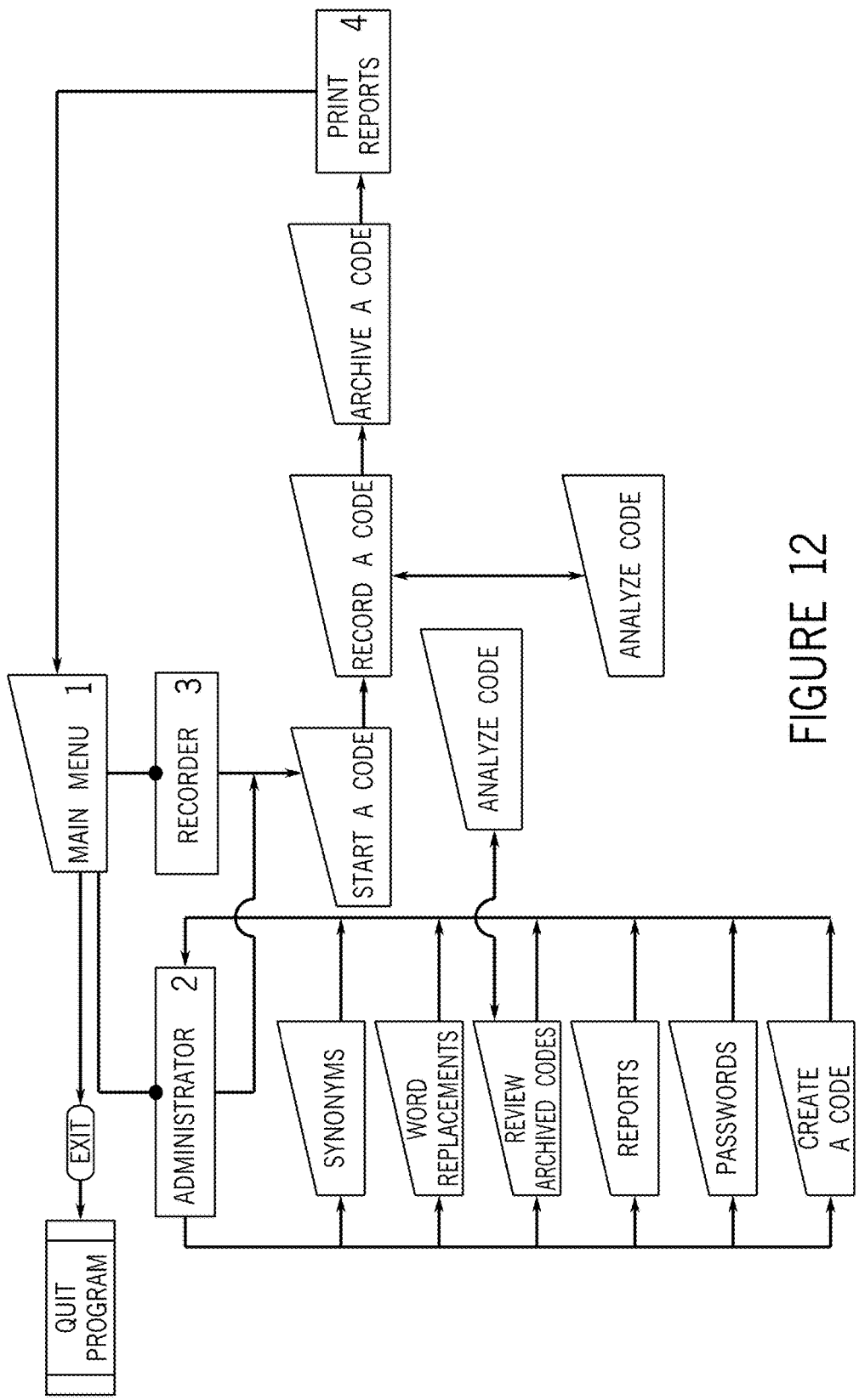
FIG. 12, illustrates the structural configuration and logical components and relationship of components of at least one Main Menu screen that may be utilized by two types of users, whose access to the functionality of the system and equipment differ based on their roles.

In accordance with disclosed embodiments, the system and equipment provide one or more screens in the GUI associated with and supporting the disclosed functionality. Examples of the structural configuration and logical components and relationship of the screens are illustrated in the figures. For example, as shown in FIG. 12, the structural configuration and logical components and relationship of at least one Main Menu screen that may be utilized by two types of users, whose access to the functionality of the system and equipment differ based on the their roles. The first type of user is the Administrator having full access to all system functionality. The second type of user is a Recorder that can only record a code.

Figure 13A:
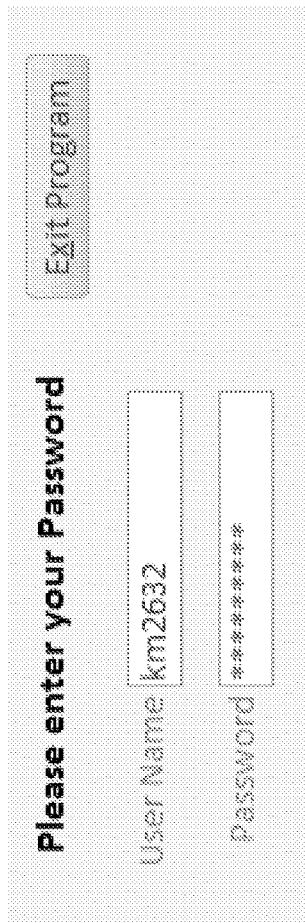
FIGS. 13A-13B are exemplary illustrations of Main Menu screen(s) or portions thereof provided in accordance with at least one embodiment.
Figure 13B:
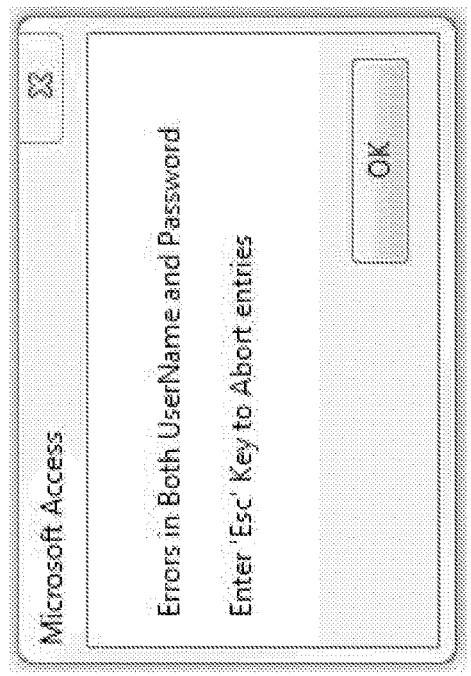

All users enter the program via the Main Menu screen (portions of which are illustrated in FIG. 13A). Only active users with a valid password may be allowed to use the system, equipment and methodologies provided. Both the user name and password may be checked. If either or both are invalid, a message is displayed. In the example illustrated in FIG. 13B, both failed.

Figure 14:
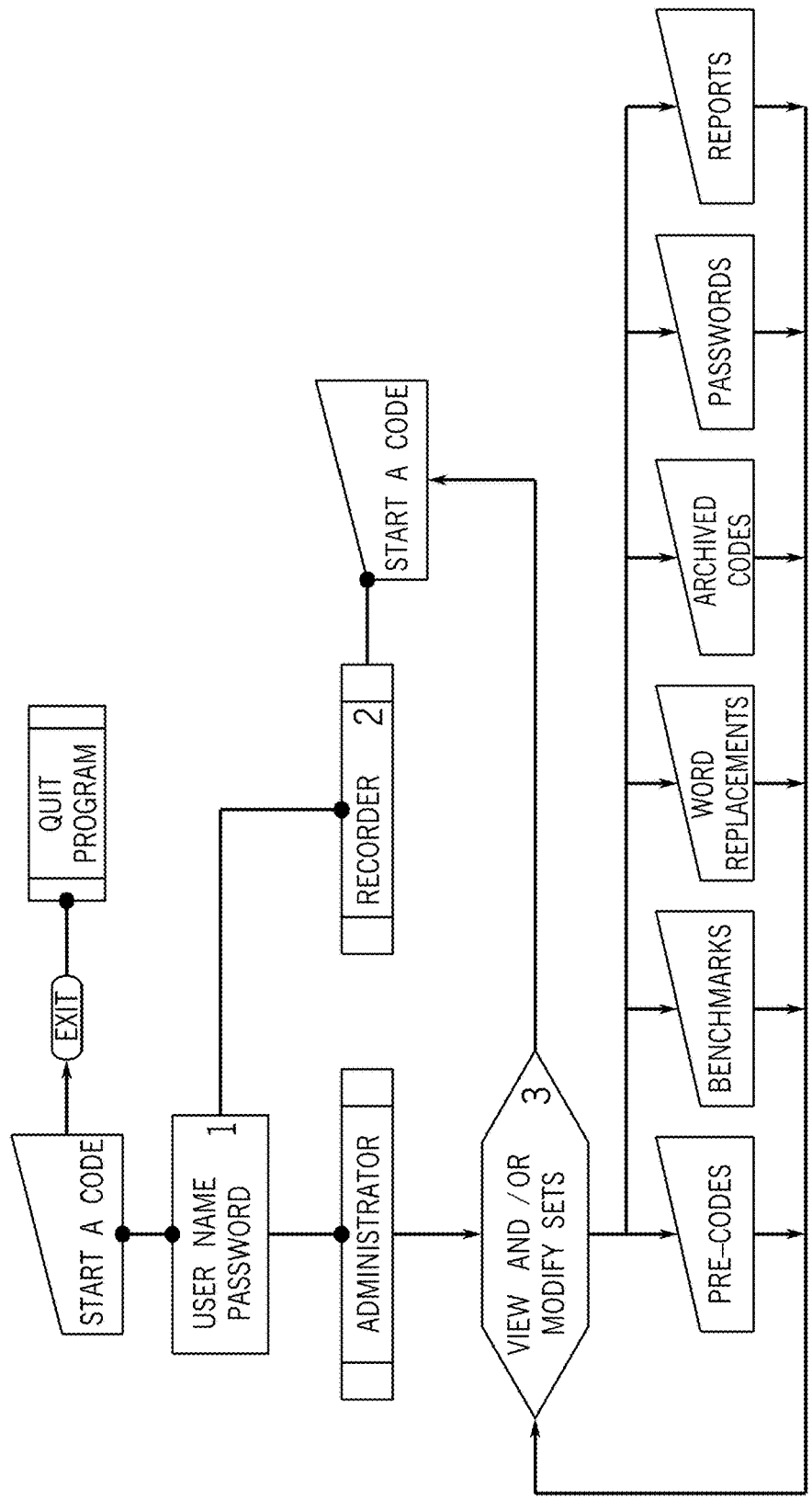
FIG. 14 illustrates the structural configuration and logical components and relationship of components of a Code Recordation screen.
Figure 15:
FIG. 15 is an exemplary illustration of a system code development (or portions thereof) for developing additional system functionality.

As mentioned above, Recorders are only allowed to enter data on a Code. When the user is determined to be a Recorder after signing in on the Main Menu, that person is taken directly to a Start Code screen (as shown in FIG. 14) that then initiates the set of Code Recordation screen(s) (shown in FIG. 17). Likewise, Administrators can also view the Start Code screen but can also access other functions (listed in FIG. 15). These consist of viewing archived codes, creating synonyms for voice recognition, management of passwords, viewing and printing various reports, changing the marker displayed on performance analysis screens denoting a possible entry error, and creating new or editing existing codes.

A third type of user, the Developer, has access to the same functions as discussed above for the Administrator and shown in FIG. 15. However, optionally, only the Developer can access the last two on the list illustrated in FIG. 15. These functions involve standardization of terminology and should be delegated to a minimal number of individuals who take responsibility for these actions.

Figure 16:
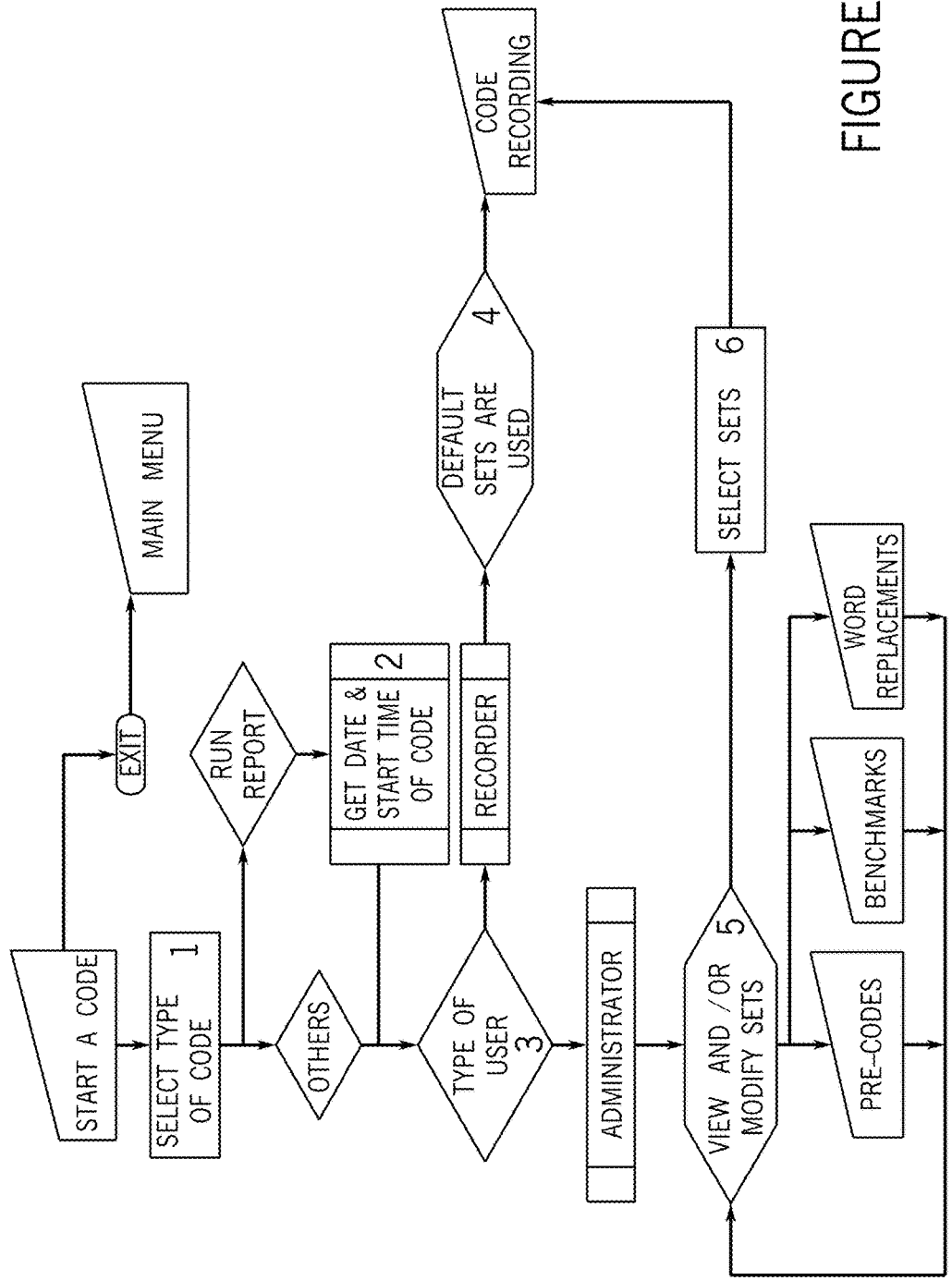
FIGS. 16 and 18 illustrate the structural configuration and logical components and relationship of components of a Code Recordation screen.
Figure 17:
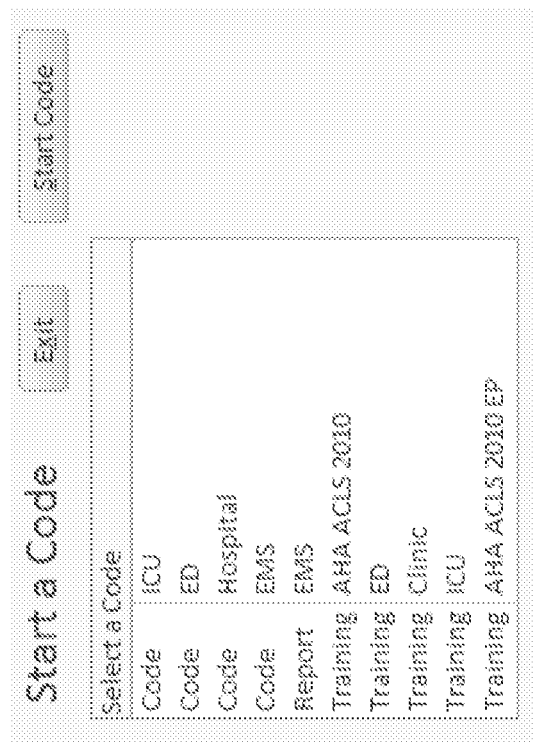

The system logic used in starting a code is shown in FIG. 16. The User is asked to select a code from the list as shown in FIG. 17. Only codes that have been completely developed are shown in this list.

Figure 18:
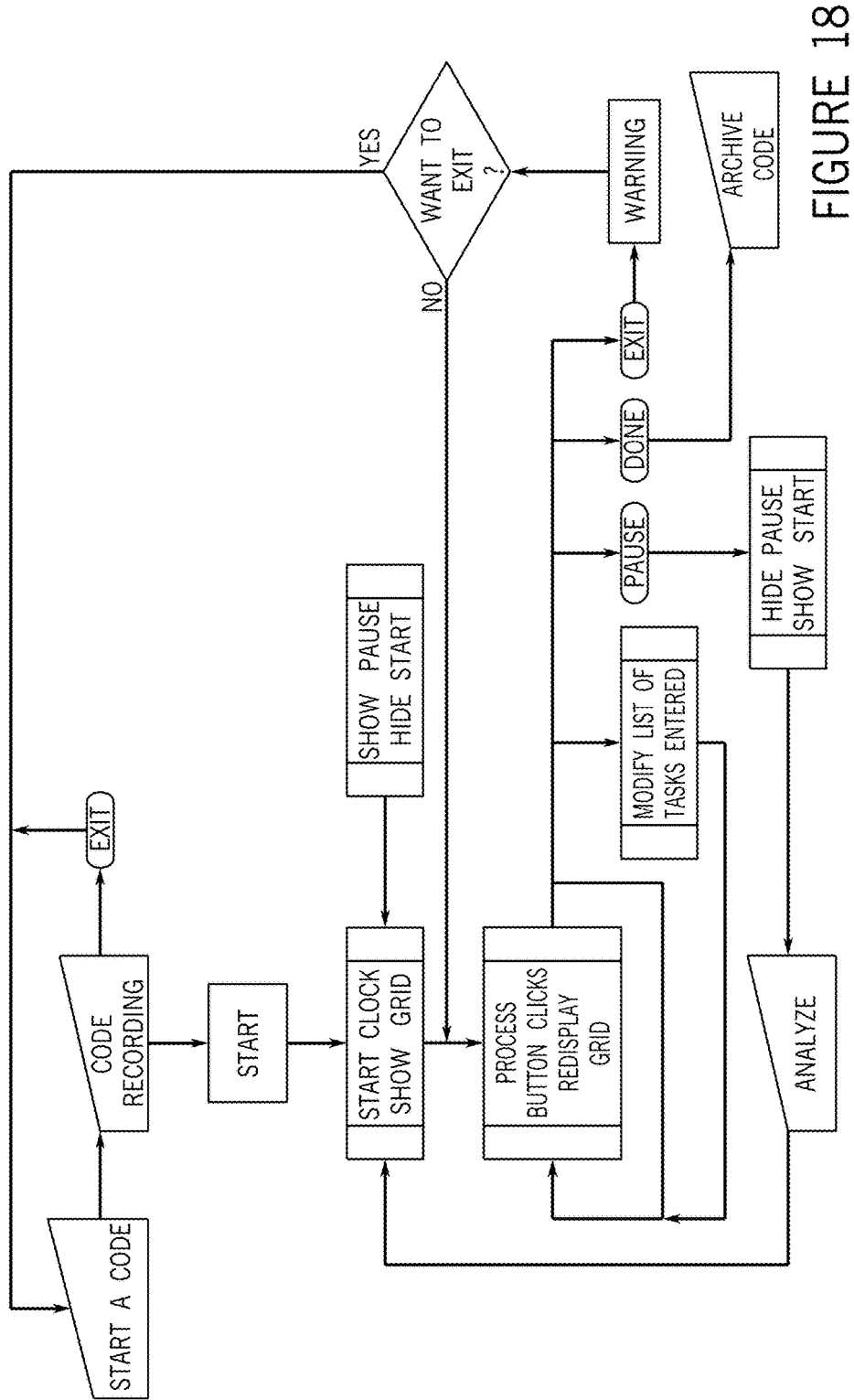

Turning to an explanation of how Codes are actually recorded using the disclosed embodiments, FIG. 18 illustrates configurations and relationships of various screens displayed on the GUI that are used to record tasks performed during a Code, and which may be augmented by voice recognition technology if available. Performance of tasks may be timed using a system specific clock (incremented in minute: second format), and except for real Codes, where recording is continuous, the system clock can be temporarily paused and restarted.

Tasks may be displayed for selection on a grid. The current state of the Code changes after each task is performed; and grid content is updated after each task is recorded to reflect this state. A task list may be used to display all events recorded and its contents may be editable. During pauses and after recording is completed, an objective analysis may be immediately available, and may be used to discuss responders' performance.

Since only codes that have gone through all the code-creation steps are available on the Start-code screen, as explained above, the pre-code set (or other data) may define both a protocol used during the Code and a series of tasks that occur before the start of the Code. The protocol (or other data) may be used to determine which drugs are available during the Code and which devices are available. The pre-code tasks (or other data) may be included in a task list to be displayed using the GUI of the disclosed embodiments. The add/rename words process revises task and task-display names for a subset of task names. Likewise, the pre-code tasks also modify the initial state of a grid display provided to the Recorder during Code documentation recording.

For example, all drugs (medications) that are available for use may be displayed on a screen with the GUI, either on the screen's grid or in an auxiliary list displayed in a pop-up form. Drug words may have an additional property, e.g., dose. Thus, when a drug is administered during a Code, the Recorder is asked to enter the dose; and, if none is entered at that time, its usual dose is presumed to be given with the understanding that this may be revised before the Code data is considered accurate and the Code is archived.

Upon entering the set of screens presented to a Recorder during Code documentation recording, the task grid may not be visible on the screen if the system clock has not been started, and the status of compressions (which may be visible on subsequent screen shots) may not be visible. This situation only occurs in training codes where starting a code may be delayed until the trainee is ready. In real codes, the clock is started when the screen is shown (and as mentioned above cannot be paused until the code is completed).

Figures 19, 20:
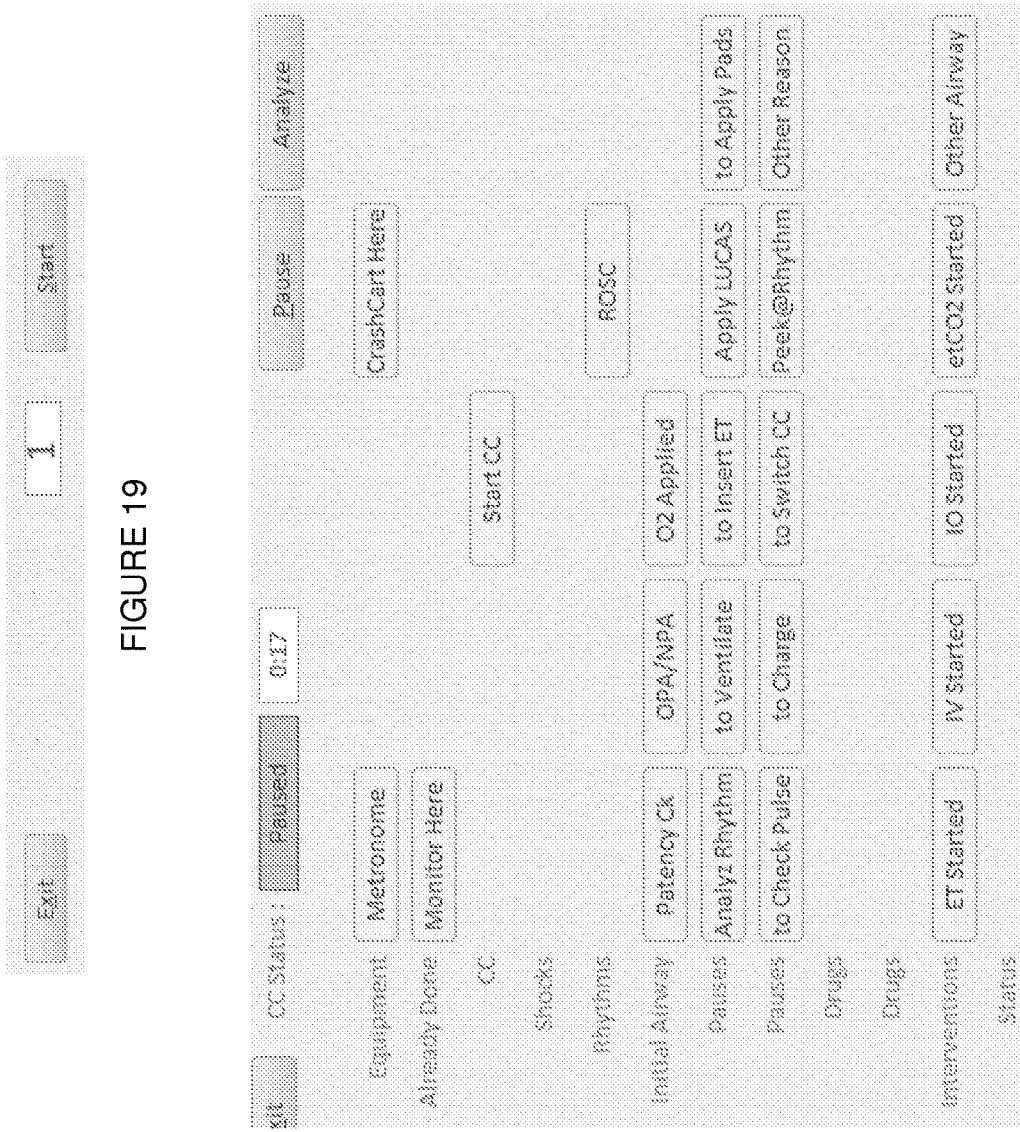

All code-types, except real codes, may utilize the Start icon as illustrated in FIG. 19. Selecting (e.g., a user selecting the Start icon), may trigger display of the task grid and starting of the system clock along with displaying the status of Chest Compressions (CC) on a screen of the GUI. As illustrated in FIG. 20, because the Start CC task has not yet been selected, the CC status may be paused. The organization of tasks on the task grid may be predetermined by a Developer using the Organize Tasks on the Grid screen illustrated in FIG. 2 explained above. The initial contents of the task grid may also be selected by the Administrator.

The visibility of the pause and analysis icons may also be code-type dependent. For example, the Mock and Testing Code scenarios are educational in nature and pausing to analyze and discuss what has transpired is appropriate functionality. Alternatively, recording in a real Code may be continuous. Therefore, in real codes, pausing and analyzing may not be allowed (e.g., these icons may not be visible on the screen displayed on the GUI); thus, optionally, only the exit and done icon options may be available, as shown in FIG. 21.

When the done icon is selected as shown in FIG. 22, the warning illustrated in FIG. 23 may be displayed (and the clock is paused—even during real codes—so as to not introduce inexplicable pauses). If the user answers no or cancel, they can then resume entering data as before by selecting the start icon. If the message above is answered yes, recording may cease and cannot be resumed. The Code Analysis screen may then be displayed, an example of which is illustrated in FIGS. 41-55 discussed below. Thus, after the analysis is reviewed and presumably discussed and any corrections to the events recorded are completed, selection of the back to code icon on the Code Analysis screen may trigger display of the screen(s) for enabling resumption of recording of a Code; however, if the Code Analysis screen is reached after the code is done, editing can be performed for the Code but no further tasks can be entered.

Figure 24:
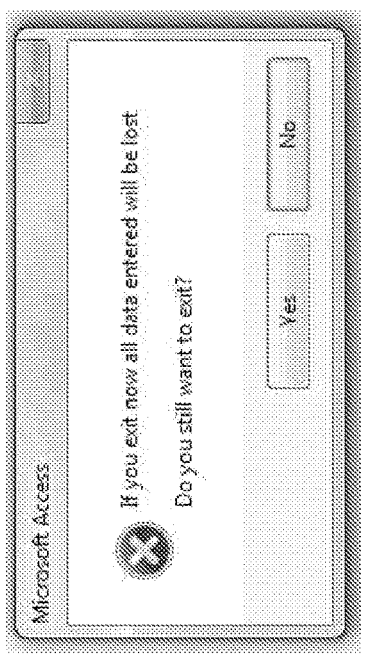

Selection of the exit icon on the Code recording screen can be problematic because all data entries may be deleted as a result. Accordingly, the message illustrated in FIG. 24 may be illustrated. If yes is selected, all data may be discarded and the user returns to the Start-a-Code screen.

Figure 25:

In accordance with the disclosed embodiments, run report codes may require specific functionality because data may be entered retrospectively. For example, data may be entered from a report of some kind after an event; however, sometimes tasks may be entered while a Recorder is observing or listening to a computer download that runs continuously (albeit with a different time reference than the equipment and system of the disclosed embodiments). These two recordation methods may be termed "manual" (e.g., data and timing is observed or listened to and input by the Recorder) and marking (e.g., the timing is recorded by the program running on the GUI but the user can enter the specific event associated with that "mark" at a later time). It is useful for the system to be configured to optionally accept designation of the input mode for such data as shown in FIG. 25. The entry mode can be changed at any time.

Figure 26:
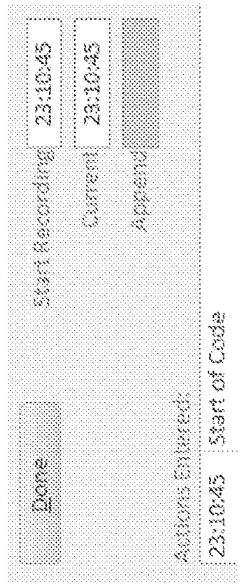
Figure 27:
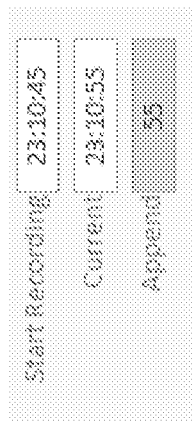
Figure 28:
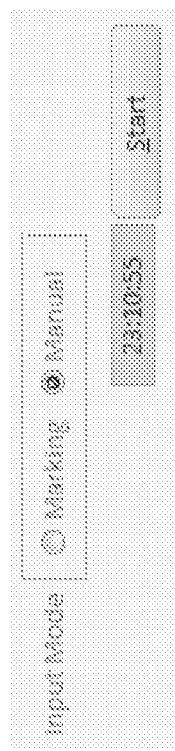

In manual mode when recording a Run Report, the system clock may not be used. Instead, the occurrence time for a task may be entered by the Recorder when that task is selected. For example, the example illustrated in FIG. 26 shows a screen section that is only visible for Run Report codes. The start recording time may be entered earlier when the Recorder elects to start a Code. Thus, the current time may be initially set to the start recording time. Entries in the append field (used to correct the recorded time) illustrated in FIG. 26 may be appended to the current time value; and since appending involves only the terminal portion of the current time, this process eliminates the need to re-enter all the digits required for a time. Non-numeric characters may be ignored in this process. The entry field's color may change. The revised current time may be displayed in the clock field on the screen and be used to time stamp the next grid task entry. In the example illustrated in FIG. 27, the value 55 is appended to the time 23:10:45 resulting in a time of 23:10:55. Thus, the new revised current time is then displayed in the clock section, as shown in FIG. 28, and used as the time of the next task entered.

Figure 29:
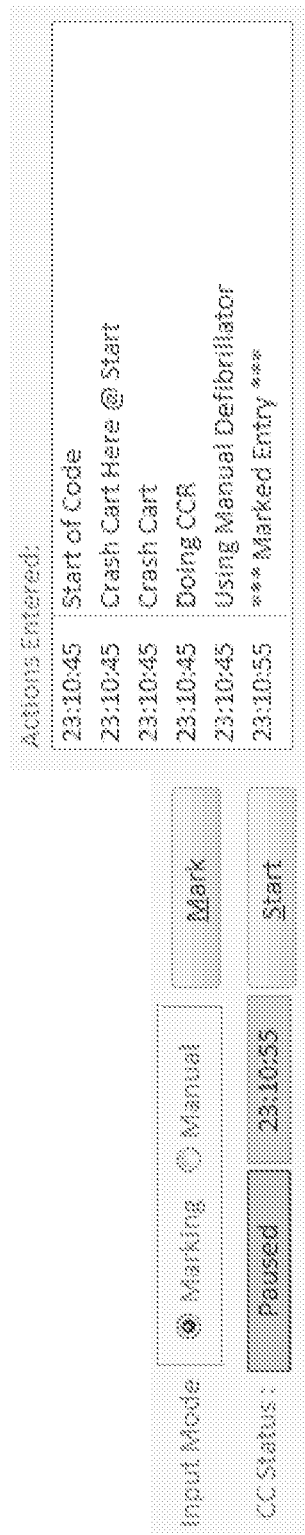

The marking mode allows the Recorder to play back a timed stamped download recording of events that transpired during a Code. If the clocks of the displayed screen and download are synchronized when the download is played, the grid can be used to record tasks in a continuous fashion. This may be accomplished by entering the starting clock time for the download into the system clock as shown in FIG. 28. Thus, when a download and a displayed screen are stated at the same time, events can then be recorded in two ways: selecting a specific task on the grid when it occurs; or selecting the mark icon (instead of a specific task). When the mark icon is selected, a special task is entered in the list of events, as shown in FIG. 29.

Figures 30, 31:
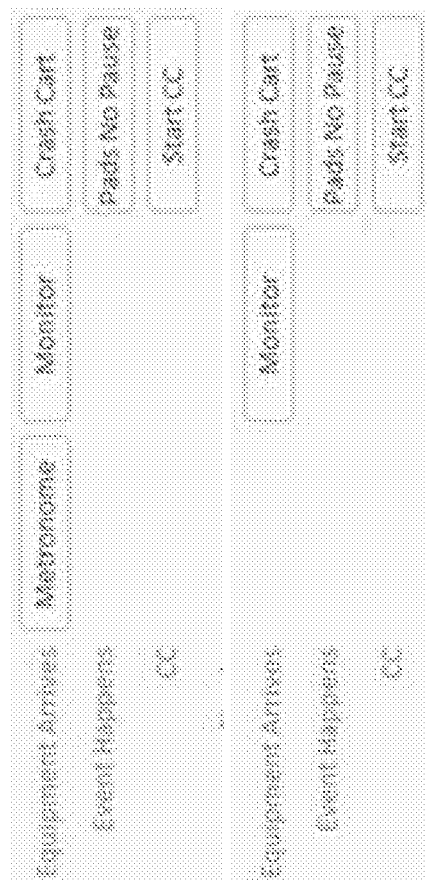

As mentioned above, accurate recordation and documentation of the timing of tasks during a Code enables objective analysis, feedback and documentation of the tasks performed during treatment of a cardiac arrest event. As discussed above, in some code-types, the system may be paused, e.g., during Mock and Testing code-types. During a pause, if the Recorder selects the marked entry and then selects a task such as start CC, the system and equipment may log that task using the marked entry time, as illustrated in FIG. 30. Likewise, selecting the start icon may trigger restarting of the clock and the start icon is hidden and the pause icon becomes visible.

However, in real Codes, where pausing and analyzing is not permitted, no analyze icon may be included in a displayed screen set associated with recording a Code. Rather, only the done icon may be illustrated, and when it is clicked and confirmed, the Analyze button appears.

Within the task grid displayed within the Code Recordation screen(s), when a task is selected, the system and equipment may respond by performing a serious of operations. For example, the displayed task grid may be altered to reflect the dynamic state of the Code by, for example, using the show/hide logic associated with each task. Using such logic reduces the number of choices the Recorder has to choose from, which in theory should reduce data entry errors. Additionally, tasks that are only performed once may not be erroneously re-entered. For example, as illustrated in FIG. 31, if the metronome icon was selected by the Recorder, the icon may disappear from the task grid.

Figure 32:
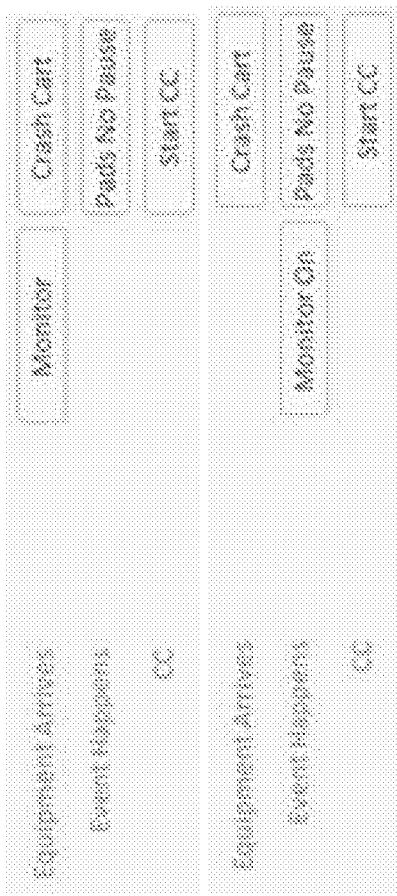

Likewise, the use of show-hide logic enables the system and equipment to be configured to operate in a once-done-it-is-replaced mode of operation. For example, monitor arrival is a one-time event; thus, once the Recorder selects the associated icon on the Task grid as shown in FIG. 32, the icon disappears. However, the newly arrived monitor would useless until it is turned on; thus the Task grid may also include a monitor on task icon, as shown in FIG. 32. It should be appreciated that the interval between when the monitor arrived and when it was turned on may be analyzed, as a result. This same logic may be applied to situations where the icon content toggles; e.g. if something that starts may fail and then needs to be re-started, the icon content toggles between xx-Start and xx-Failed. During the development of a code this process is termed "cycling" and a screen is available to create sets of cycled events.

Figure 33:
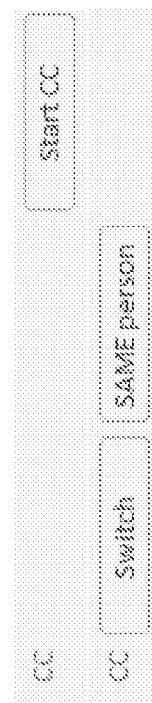

Similarly, the start CC task may occur only once. Thus, when it is selected by the Recorder, it may be replaced by two other CC options: switch and [resume by] same person, as shown in FIG. 33.

Figure 34:
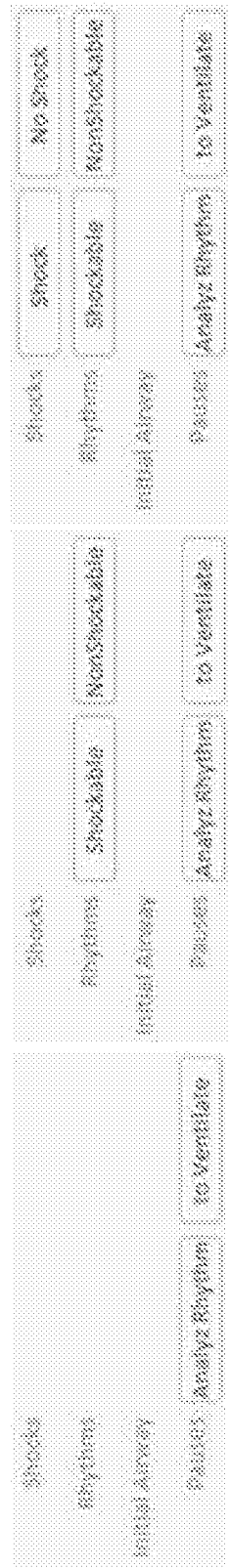

Further, some tasks may follow a logical sequence in their performance; that is they can only be performed after a prior event occurs. Accordingly, systems and equipment provided in accordance with the disclosed embodiments may utilize program logic that prevents such tasks from being logged before a prior necessary precursor event occurs. For example, the cardiac rhythm must be analyzed before the type of rhythm can be determined. Thus, the analyze rhythm icon must be selected prior to display of two alternative rhythm choice icons, shockable and non-shockable, which are displayed on the screen. Similarly, the type of rhythm must be determined before a decision on how to manage the rhythm can be made. Thus, the type of rhythm, shockable or non-shockable, must be selected before a shock or no shock selection is input by the Recorder. Further, selection of either a shock or no shock icon may trigger display of content as illustrated in FIG. 34. In accordance with at least one embodiment, the choices (e.g., shock or no shock) available may be colored to prompt the Recorder in making the appropriate selection.

In accordance with disclosed embodiments, a task may be time stamped when it is selected by a Recorder on the Code Recordation screen(s) associated with a code-type and output on the GUI. Optionally, all tasks that have been entered into the screen sets may be displayed in a task list located to the right of the task grid of a screen. Thus, as illustrated in FIG. 35, the tasks with times of 0.00 were performed before the Code was started—when the pre-code logic associated with this Code was activated. Note, in accordance with various embodiments, the task names in the list may be more descriptive than on the task grid icons. Moreover, the tasks in the list can be edited; for example, selecting a list entry may allow the user to delete the task in FIG. 36.

Figure 37:
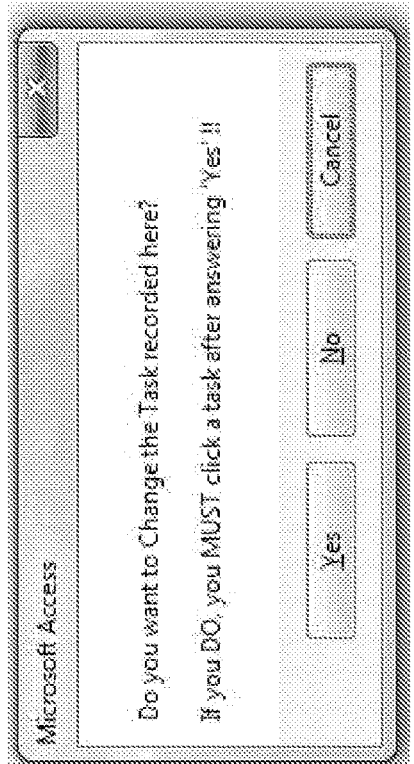

Right-clicking an entry on the list may enable correction of an erroneous task entry. Note, this may not be permitted during a Real Code until recording has ceased (e.g. by selecting the done icon); however, for other code-types this correction may be permitted during a pause in recording. In at least one implementation, the task itself, but not the time stamp may be changed, as illustrated in FIG. 37.

As explained above, in accordance with the disclosed embodiments, real Codes cannot be paused, whereas, for other code-types, the entry of tasks can be paused. Pausing is usually done to discuss some aspect of responder's performance; and such a discussion is aided by the ability to analyze events that have occurred up until the pause. Pausing also permits corrections of previously entered tasks, as mentioned above. The system clock stops during the pause; and it is resumed when the start icon is subsequently selected. Task entry may then be resumed.

Figure 38:
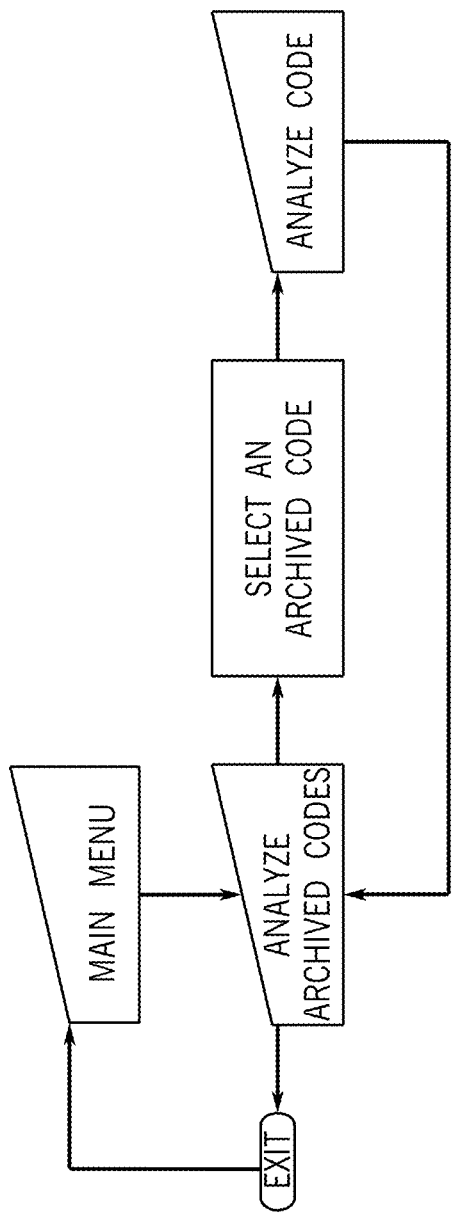
Figure 39:
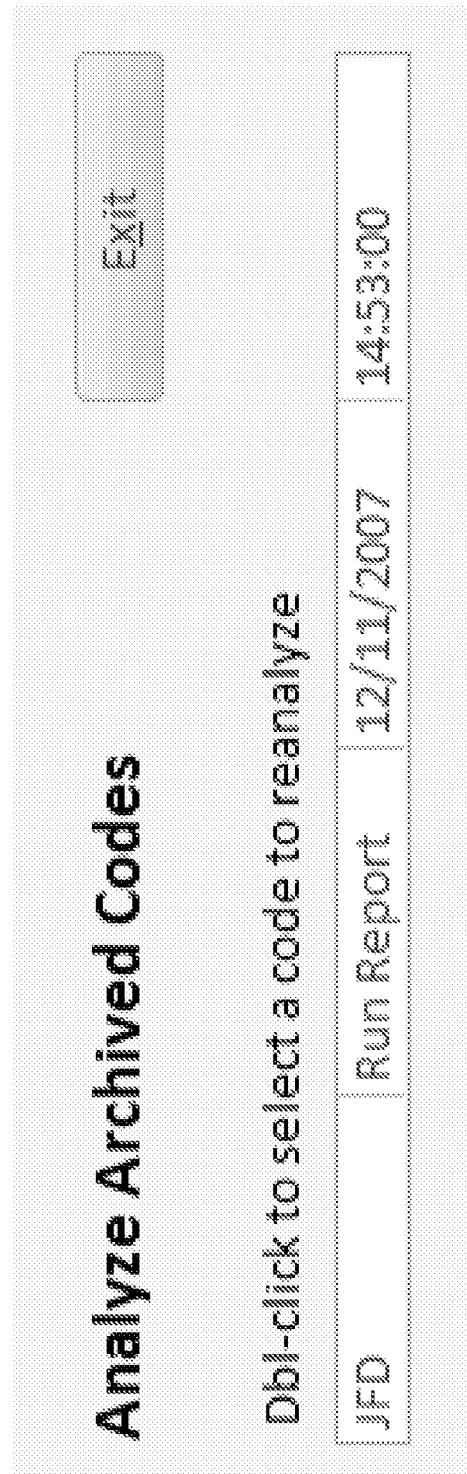
Figure 40:
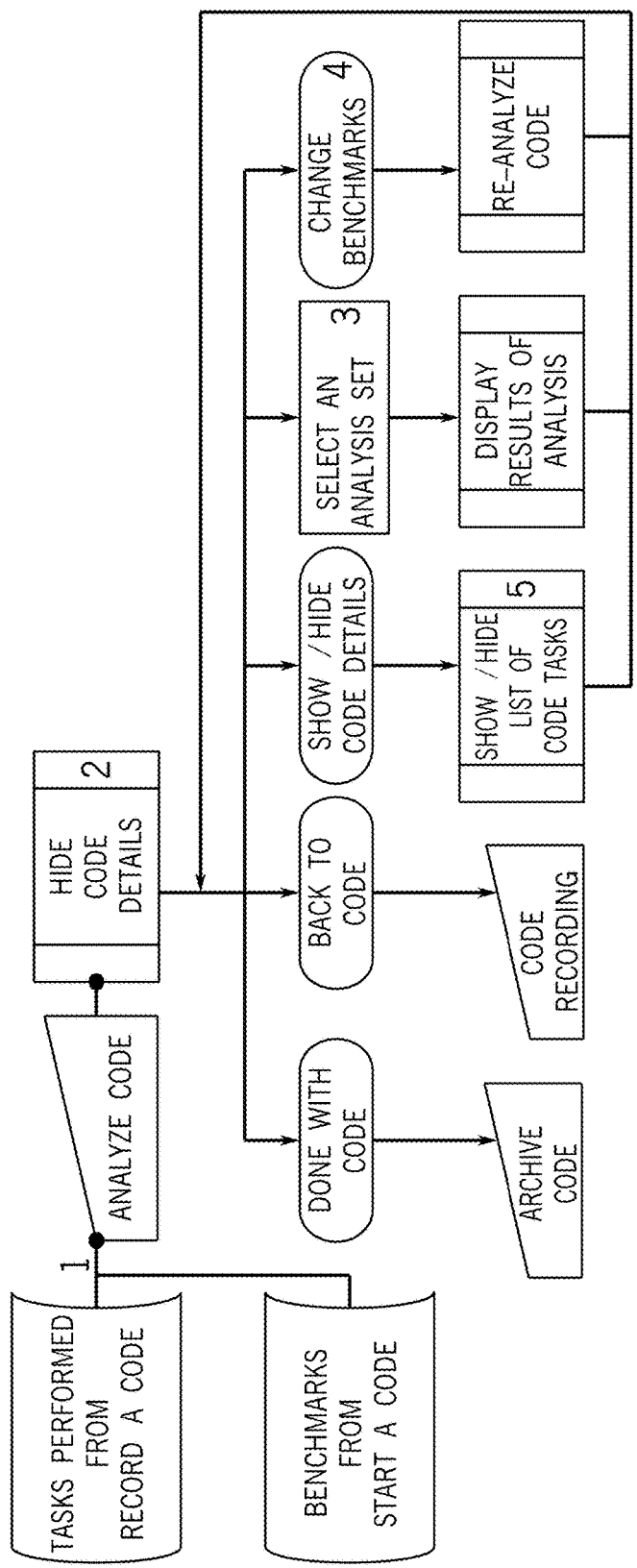
FIG. 40 illustrates the structural configuration and logical components and relationship of components of a Code Analysis screen for archived Codes.

Turning to the ability to analyze archived Codes provided in accordance with the disclosed embodiments, FIG. 38 illustrates the architectural configuration of screens presented to a user to enable analysis of archived Codes. In operation, after a list of all archived Codes has been displayed to a user (e.g., sorted with the latest on top), only two options may be available: exiting to the Main Menu screen(s) or selecting one of the archived Codes to analyze, as shown in FIG. 39. A user may select one of the displayed Codes and, when an old Code is selected, it is analyzed using an original or selected benchmark set, as explained below. Subsequently, a Code analysis screen or set of screens is output to the user via the GUI. Actions available on that or those screens pertain to analysis of actions and data documented as illustrated in FIG. 40.

The benchmark set assigned to and employed when a Code is started may be used to initially perform analysis of the Code. The Code data analyzed may come from one of two sources: an archived Code, as explained in conjunction with FIG. 39, or a Code just previously entered, for example, when the system and equipment are being used for training or when a real code is concluded.

When displaying analysis of a Code, the screen or set of screens for Code Analysis may include a list of tasks performed, e.g., for the purpose of modifying its content or discussing tasks and/or events that led to a specific analytic result. However, because the Code analysis itself is the primary purpose of the screen, this list may be only an option or not displayed initially on the screen(s).

Figure 41:
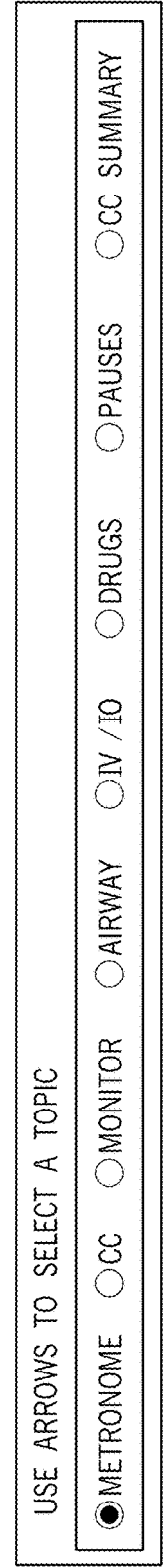

McMAID logic may be used to organize presentation of the analysis on the screen(s). Arrow keys may be used to select a category of data for the Code, for example, data pertaining to the Metronome, Chest compressions, Monitor, Airway, IV/IO, Drugs, Pauses and/or a CC summary, as illustrated in FIG. 41.

Once a category is selected, the results for the category may be displayed on the screen(s). Results may also be grouped into failed and passed categories (examples are illustrated in FIG. 42-43 pertaining to the use of a Metronome to guide chest compressions, FIG. 43 pertaining to Chest Compressions (CC), FIG. 44 pertaining to the use of the monitor, FIG. 45 pertaining to Airway related tasks, FIG. 46 pertaining to the insertion of an IntraVenous (IV) or IntraOsseous (IO), FIG. 47 pertaining to the administration of drugs, FIG. 48 pertaining to the insertion of pauses (if permitted based on code-type), and FIG. 49 which provides a summary of Time spent Doing Compressions and the Impact of Pauses upon Compressions).

As mentioned above, the benchmark set used to analyze the Code data can be changed by selecting a change benchmarks icon provided on the analyze Code screen or set of screens as shown in FIG. 50. As a result of such a selection, control may then be shifted to one or more screens in the GUI associated with benchmarking that display the contents of available existing benchmark sets for selection, as discussed herein. Administrators can also develop a new set and use this for a re-analysis. The benchmark set utilized in the analysis, whether it be an originally selected benchmark or a new one selected using a change benchmarks icon provided on the screen(s), may be displayed on the Code Analysis screen(s) as illustrated in FIG. 51. Likewise, a list of tasks can be displayed by selecting a show code details icon provided on the screen(s), an example of which being shown in FIG. 52. In accordance with at least one embodiment, changing the benchmark second for an individual benchmark is possible.

Figure 53:
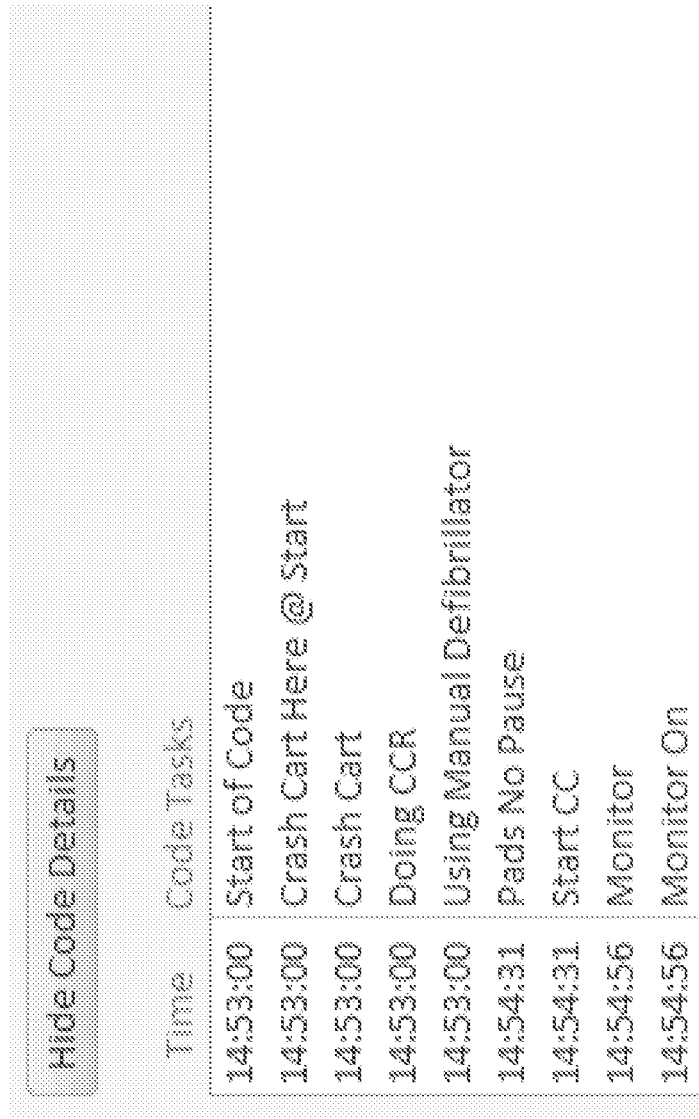

For example, as shown in FIG. 53, various details taken from an Archived Code (where Start Time is known) may be presented with the time being displayed using 24 hour clock format.

Alternatively, as illustrated in FIG. 54, if a Code was just recorded, the time may be displayed using a Minute-Second format (representing the interval since recording began) so that input errors detected in the listed details may be more readily identified if the user returns to the Code Recordation screen to edit such entries. Because the start time of the Code just entered may be, at the time of data display, not known, that time may be entered in an Archive Code screen when the done icon for the Code is selected. It should be understood that entries in the displayed list cannot be edited if the code is an archived code. However, the list entries could be edited if the code is being recorded is possible by selecting the back to code icon, as shown in FIG. 55.

Exits from the code analysis screen(s) depend upon the type of code being analyzed. Thus, when analyzing an archived code, both the back to code and done with code icons may be available to exit the Code Analysis screen(s). Likewise, when analyzing a just recorded Code, the back to code icon may be available to exit the Code analysis screen(s). Further, when analyzing a just recorded Code, the done with code icon may be available to exit the Code Analysis screen(s).

Figure 56:
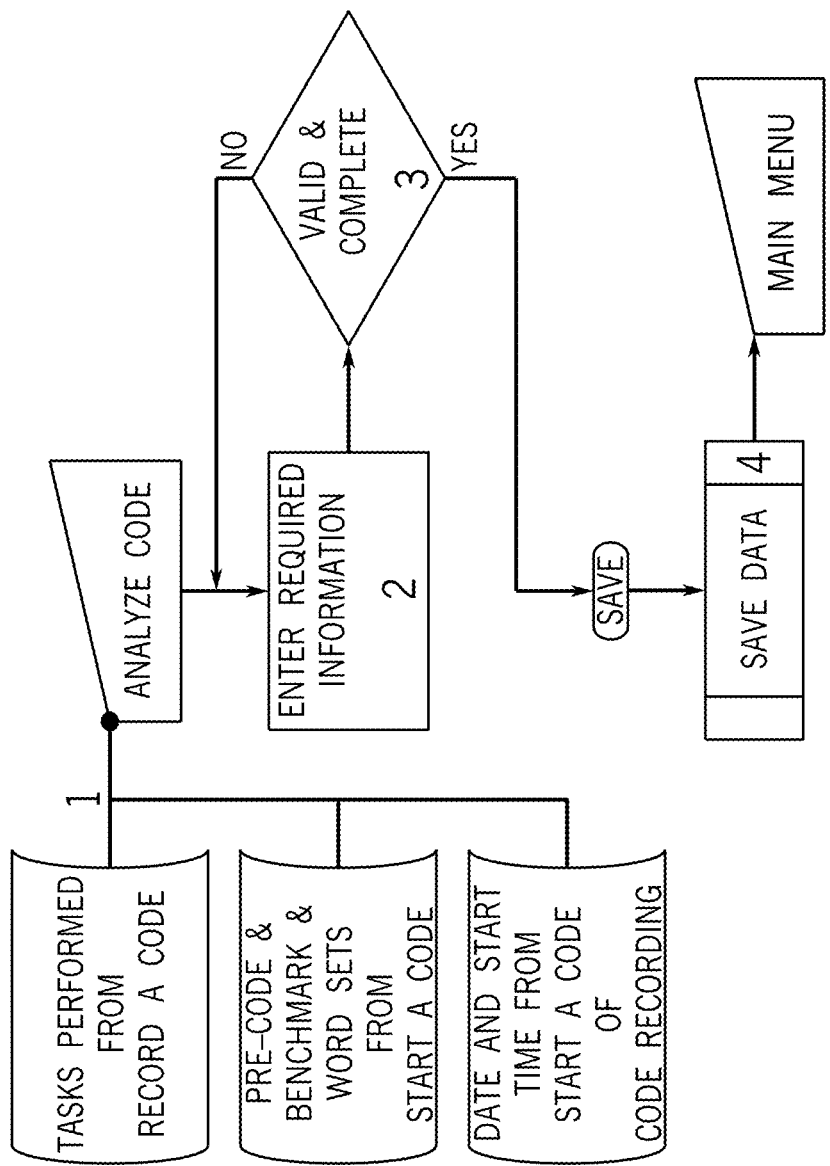
FIG. 56 illustrates the structural configuration and logical components and relationship of components used to archive a Code.

In accordance with disclosed embodiments, the system and equipment provide one or more screens associated with a Recorder archiving a Code using the GUI. An example of the structural configuration and relationship of the Code Archival screens is illustrated in FIG. 56.

Once the Code Archival screen(s) are displayed on the GUI, recording of Code events has been completed, performance has been analyzed, feedback has been provided, and responders are ready to move on to the next task at hand. Thus, at such a point in time, the system and equipment of the disclosed embodiments has served a primary purpose of providing timely feedback and education regarding a Code. However, the system and equipment have additional utility in that the Code may be documented for subsequent use and for generation of data that may be input into other systems at a medical facility, e.g., records, billing and inventory systems. Thus, although archiving a Code may be considered a housekeeping activity, archiving is essential for individual or collective retrospective reviews of performance and cross department efficiency improvement. Thus, the data collected on this set of screens should be viewed from that perspective. Report generation is a retrospective activity with ongoing value.

During the archival process, information regarding which benchmarks, pre-codes and protocols that may have been utilized is maintained and saved along with the time stamped events recorded during the Code. Additional information that may be relevant to performance improvement efforts is also obtained. (see FIG. 57) For example, the arrest type, arrest date and recorder fields on the Code archival screen may be populated using prior entries. The arrest date and arrest time may refer to when the victim's cardiac arrest began, e.g., when collapse occurred. This information may be known for Mock and Testing Codes; it may also have been previously recorded by the Recorder when the recorder was using the Code recordation screen(s), e.g., the Start a Code screen. Therefore, the arrest time may be only entered for real Codes. The arrest time may be entered in either 24 hour clock format: 21:14:22 or on a 12 hour AM/PM format 9:14:22 PM. In accordance with at least one embodiment, data consistent with the Utstein criteria can be entered and attached to the archived code (by the Administrator who is prompted to do so) retrospectively.

Figure 58:
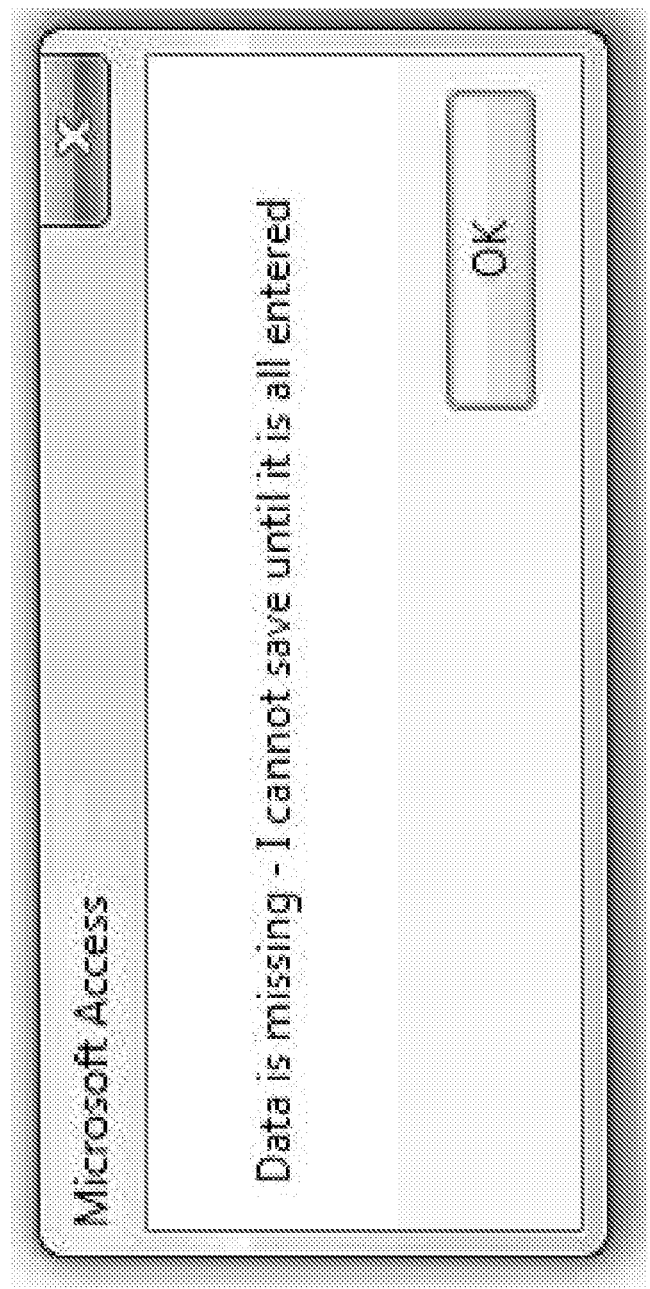

When reports are generated, the arrest time may be used to convert recorded clock times to actual 24 hour times. A comments section (as illustrated in FIG. 57) may be expanded in size if necessary. Uses would include why protocol deviations occurred, why certain benchmarks used in analysis were unrealistic, justifying for other whys. The validity of entries may be checked before saving and, if data is missing, an error message may be displayed (an example of which is illustrated in FIG. 58). During the archiving process, events recorded are translated into a standardized vocabulary that is understood by all systems, enabling retrospective analysis by researchers of a large number of codes.

Data may be initially saved on the computing device used to record the Code. Subsequently, it can be sent to other appropriate systems, data analysis systems and/or storage devices. After the Code has been archived, the user may be returned to the Main Menu screen(s). No other exit icon may be provided ensuring that all data is saved once it has been acquired.

Figure 59:
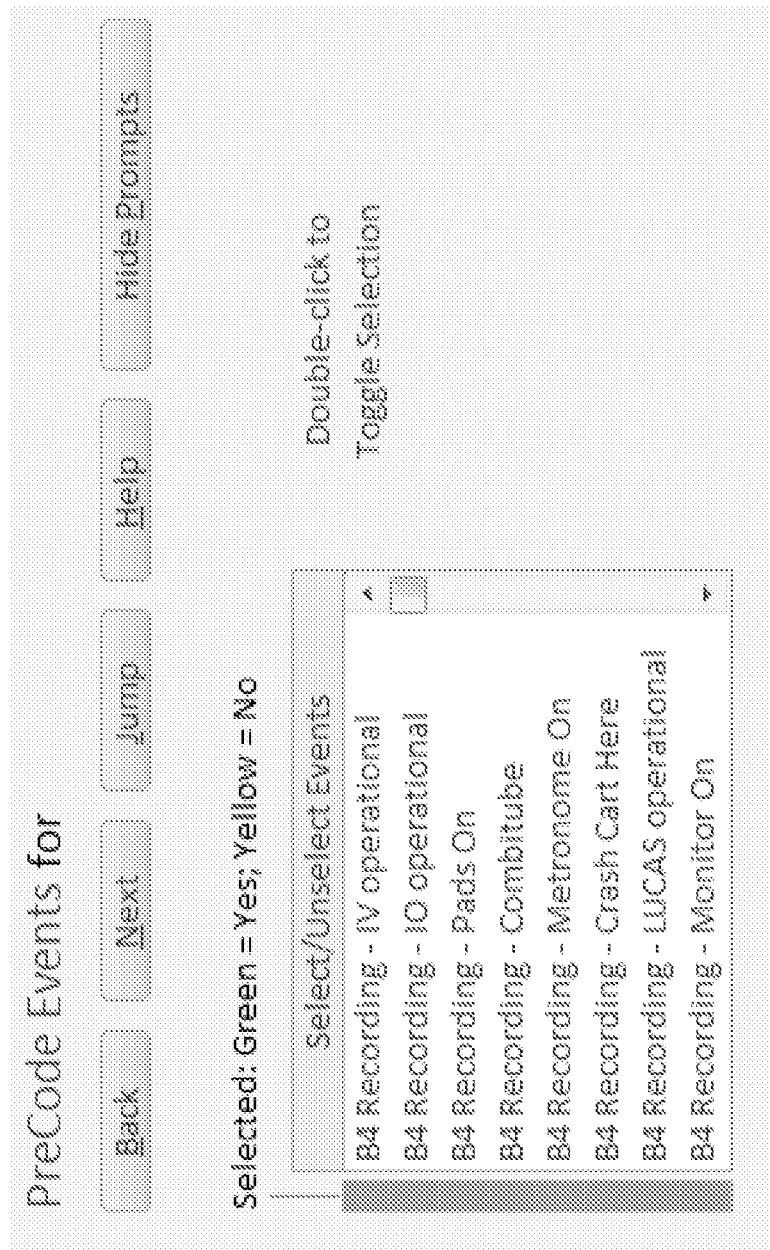
FIG. 59 is an exemplary illustration of a screen (or portions thereof) that provide functionality associated with Pre-Code Set Specification.

Pre-codes define events that occur before the start of the Code and therefore are not observed by the Recorder. They are entered automatically at the start of the Code, are logged as occurring at time zero, and impact the GUI context-sensitive content. Their use is usually limited to training codes. The development process, as shown in FIG. 59, is quite simple: double-click a pre-code entry to toggle its status between selected and not selected.

In accordance with disclosed embodiments, the system and equipment provide one or more screens associated with definition of benchmarking data using the GUI.

Adding a new benchmark is not possible; rather, users may only edit existing benchmarks. Benchmark sets are in some ways similar to pre-code sets explained above in that they may be developed by Administrators, have default sets that may be automatically selected when a user starts a Code, and may influence the analysis of a Code.

However, benchmark sets differ from pre-code sets in that they are not code-type dependent, do not affect the logic used to displays tasks on the grid, do not cause tasks to be added during the Code, do not impact logic guiding the analysis of a Code (they only affect the judgment logic, e.g., pass or fail logic) and do not influence the recording of a Code. Each benchmark has 3 components: a triggering task, a target task (the one that should be subsequently performed and a time interval (in seconds) between them that represents the maximal accepted interval. Default intervals exist for each benchmark. During the creation of benchmarks for a given code, the benchmarks are grouped on the screen using the McMaid category they belong to (FIG. 60).

In accordance with at least one disclosed embodiment, the benchmark set selected in the Code Recordation screen(s) may be changed when performing an analysis. What happens after such a change is user type dependent. For example, when the user is a Recorder, the Recorder may use an alternative set during analysis discussions; however, Recorders may not be allowed to modify which benchmark set is used in a final analysis because an Administrator made that decision when the default benchmark was set in the Code Recordation screen(s). Recorders can only view the contents of a benchmark set; they cannot modify set contents or develop a new set. Administrators can do what is not permitted for a Recorder.

Figures 60, 61:
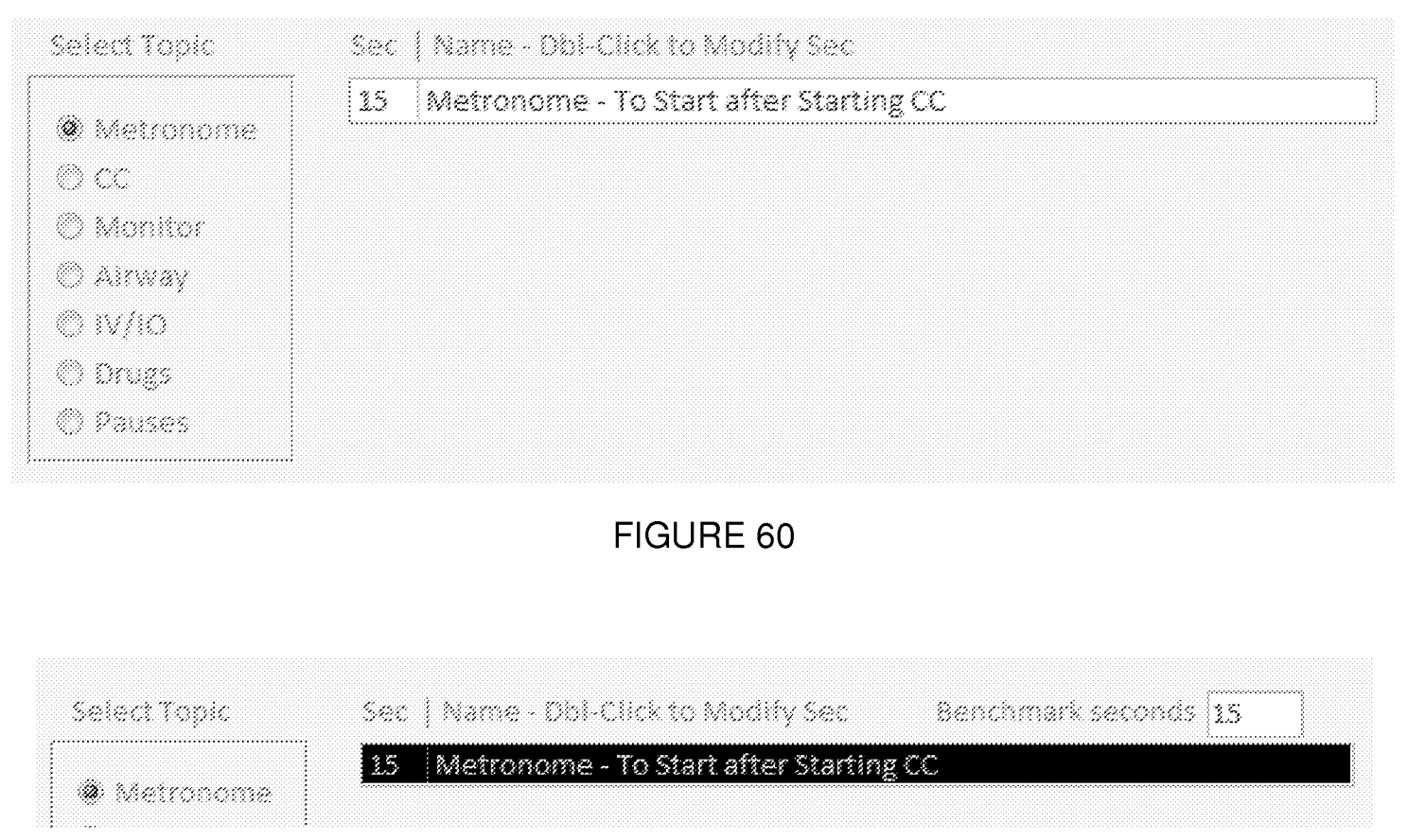

In accordance with at least one embodiment, benchmarks for all sets may be grouped using the McMAID categories shown on the left in FIG. 60. Thus, in this example, when a category is selected (e.g., using arrow keys may be easier than selecting an icon), the associated benchmarks may be displayed. In the example illustrated in FIG. 61, only one benchmark exists for metronome and the name and the default benchmark Sec (second) are displayed.

Within the benchmark screen(s), if an item is selected, the original default or user modified value in seconds for the benchmark seconds may be displayed as illustrated in FIGS. 62A-B. If the benchmark seconds value is edited it becomes the new second value (sec) for that benchmark item. Examples of the benchmarks for other McMAID categories of a benchmark default set are shown in FIG. 63A-F.

Figure 64:
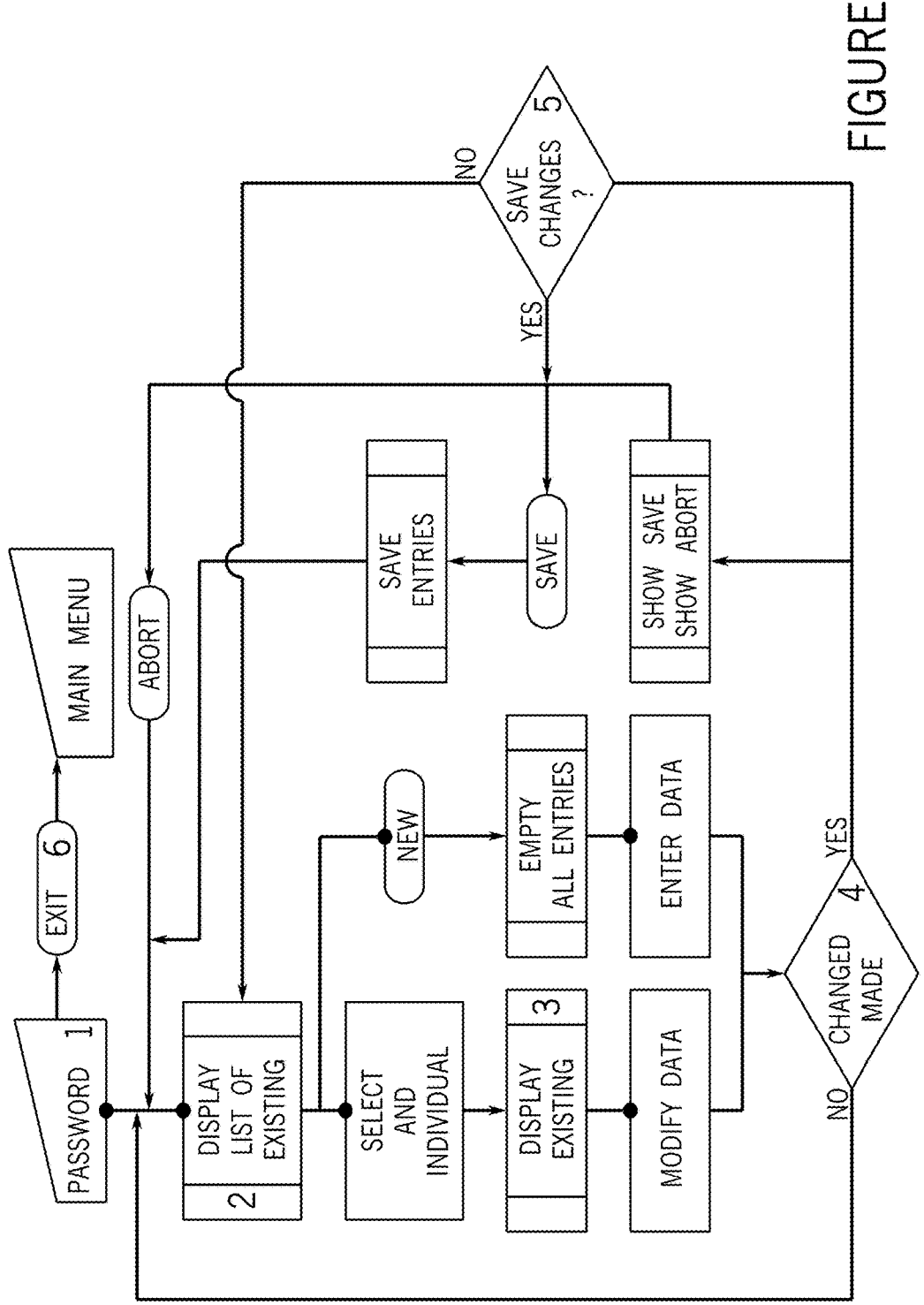
FIGS. 64-65 illustrates the structural configuration and logical components and relationship of components used for system functionality development.

In accordance with disclosed embodiments, the system and equipment provide one or more screens associated with Program Development using the GUI. An example of the structural configuration and relationship of the program development for password input is illustrated in FIG. 64. The Program Development screen(s) may be used only during development of system functionality and may not be accessible to Recorders. Thus, a Developer, with a prescribed password, may access these screens from the Main Menu screen(s). Optionally, the Program Development screen(s) may be accessed by an Administrator, e.g., if a justification for the Administrator's request to make changes in the task grid is deemed valid.

Figure 65:
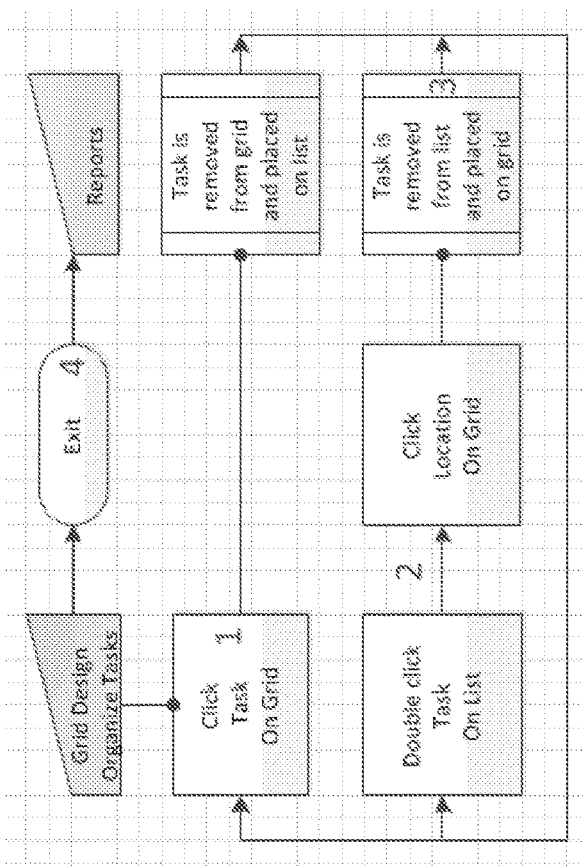
Figure 66:
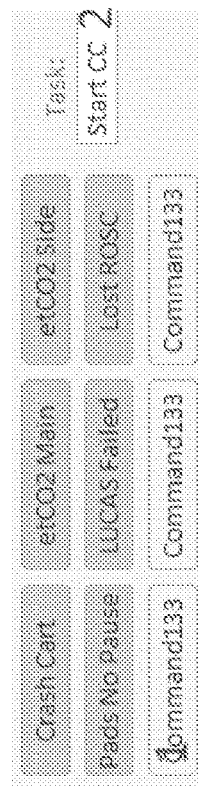

One of the Program Development screens enables the ability to organize tasks on the task grid, as illustrated in FIG. 65. Thus, the task selection tool, i.e., the grid, is shown on this screen and consists of rows of task icons (as illustrated in FIG. 2). Each row contains a category name and contains tasks in that category. All available tasks are either on the grid or in an adjacent list of unassigned tasks (FIG. 66) Task icons (in FIG. 2) 210 with tasks assigned to them differ from icons 215 that have no task assigned to them. Tasks cannot be assigned to icons in the Status row because this row is used to display the current status of one of the interventions selected in the row above.

Figures 67, 68, 69:
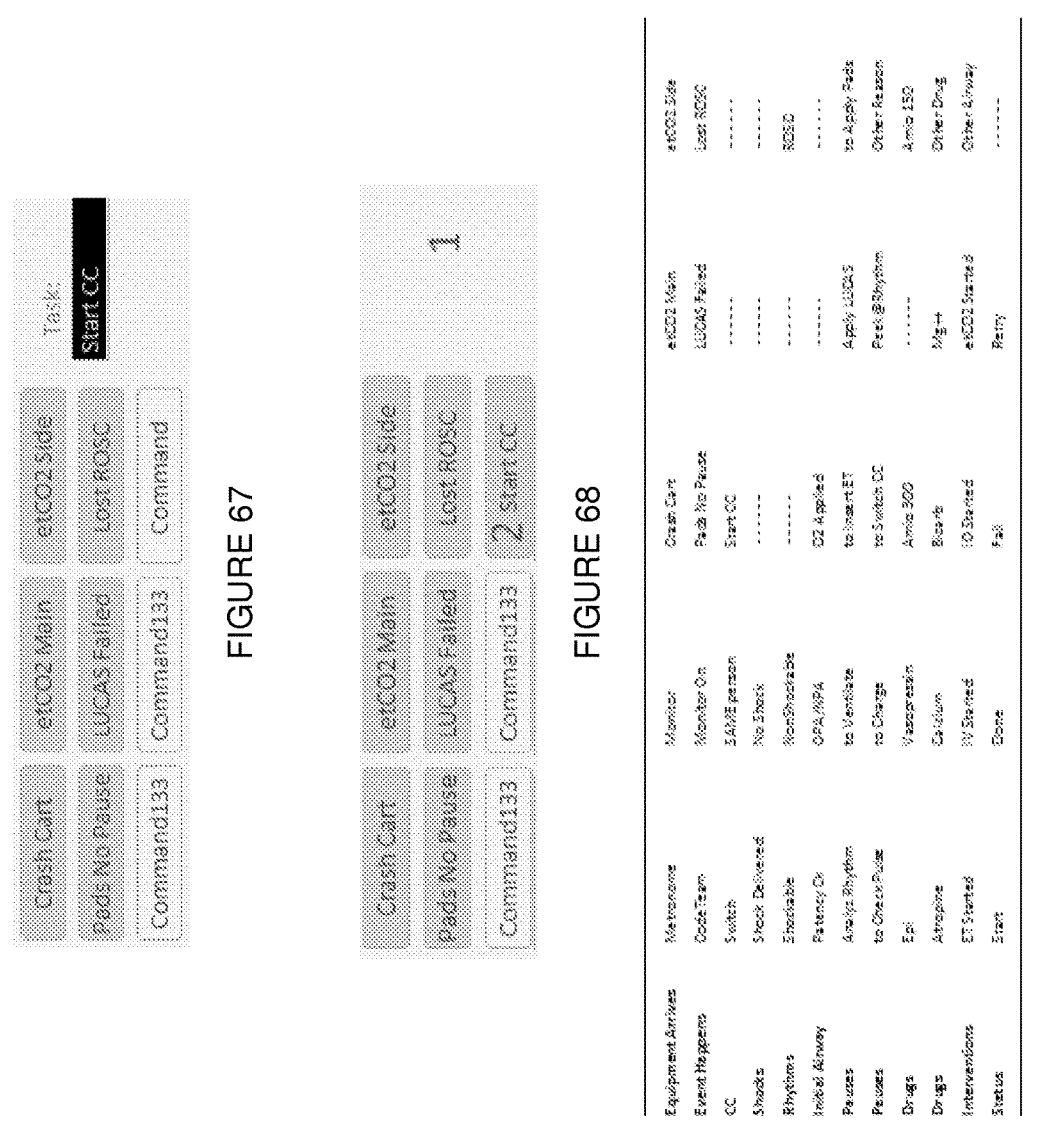

Selecting on a task in the unassigned list and clicking on a grid icon removes it from the list and places it onto the grid. In FIG. 67 Start CC is selected in the list and when a grid icon is clicked (FIG. 68) it is placed on the grid and removed from the unassigned list. Although not shown in the figures, if a grid icon is occupied by a task and that icon is selected for a task in the unassigned list, the initial task on the grid is removed and is placed in the unassigned list. The reverse is also possible, i.e. clicking an icon with an assigned task removes the task from the grid and places it in the unassigned list.

In accordance with at least one disclosed embodiment, drugs may be placed either on the grid (in row(s) dedicated to drugs) or on a separate list that will be used to populate a popup screen (that is accessible by an "other drugs" icon on the grid). This option minimizes grid data displayed by including only commonly used drugs on the grid and yet allows the selection of less commonly used drugs when needed.

In accordance with at least one disclosed embodiment, functionality may be provided to enable reversal of a change, e.g., by a user inputting an Alt-Z key stroke, and multiple reversals may be possible.

In accordance with at least one disclosed embodiment, there may be no save icon on the Program Development screen(s) because each change may be saved in the system and equipment files when it is made.

Optionally, although not shown in FIG. 2, the Program Development screen(s) may also include a print icon that triggers output of a printable report showing task locations on the grid displayed, as shown in FIG. 69.

Figure 70:
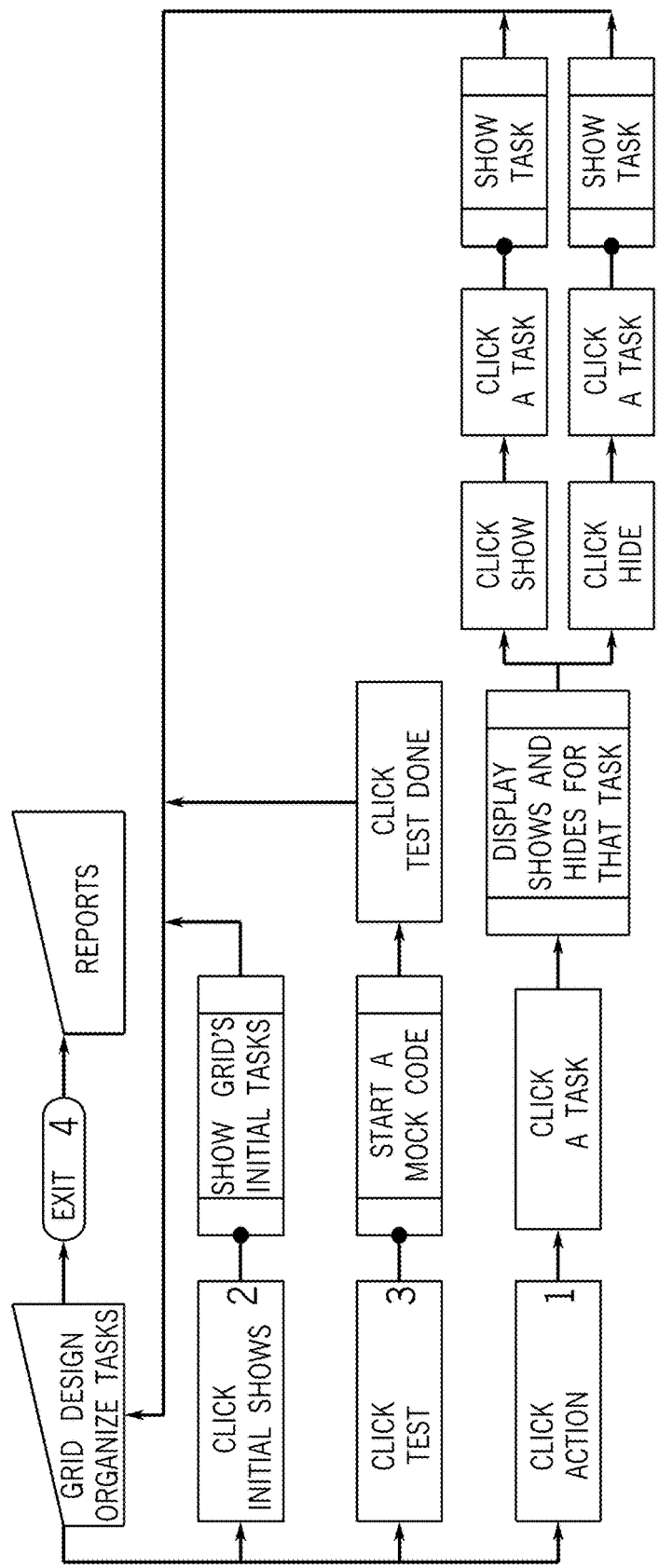
FIG. 70 illustrates the structural configuration and logical components and relationship of components used for organizing tasks on a task grid.
Figure 72:
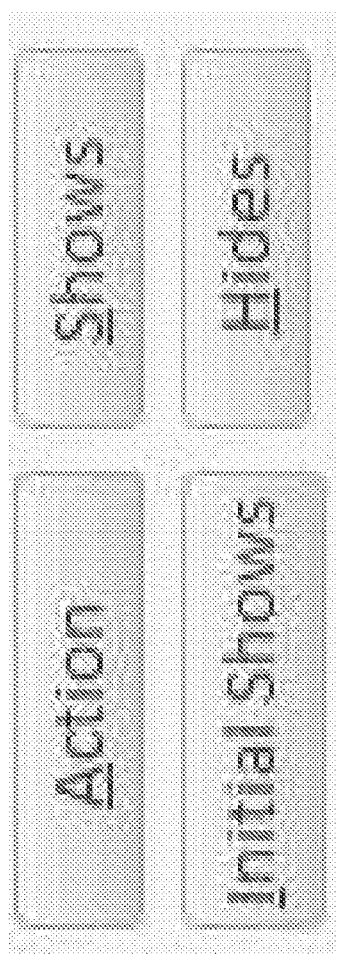
Figure 73:
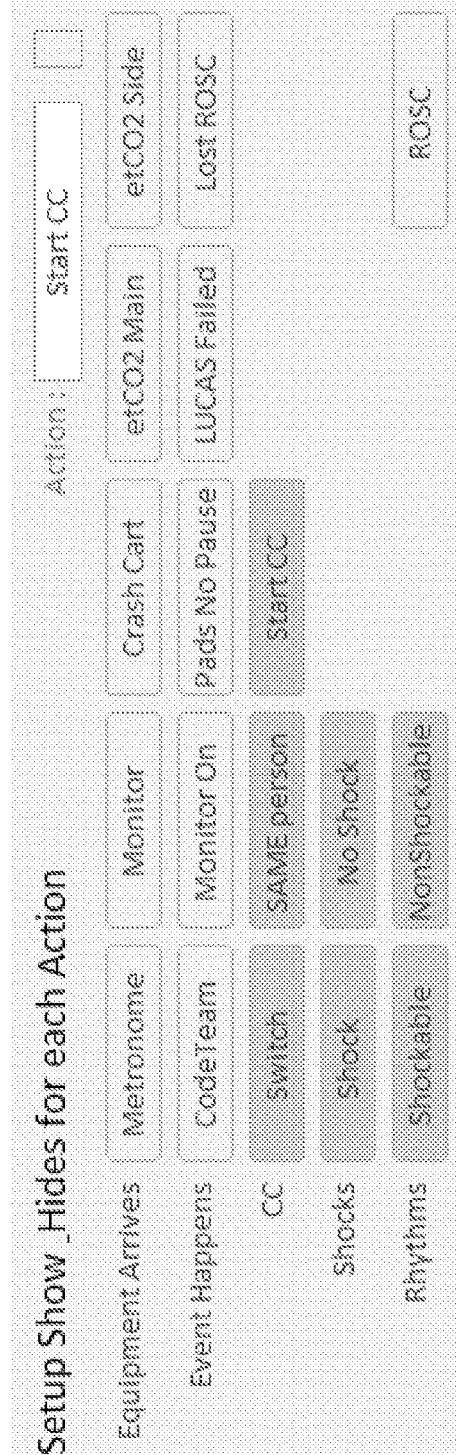

As mentioned above, the relative ease of use provided by the systems and equipment designed in accordance with the disclosed embodiments at least partially results from the use of show-hide logic that enables the ability to show or hide tasks on the grid using logic associated with the preceding task entered. Thus, in accordance with disclosed embodiments, the system and equipment provide one or more screens in the GUI associated with setting up the relationships between tasks and data to determine what is shown in association with each individual task. An example of the structural configuration and logical relationship of the show-hide selection logic is illustrated in FIG. 70. The Show-Hide Selection Logic screen(s) may be used by an Administrator or Developer to determine which tasks are initially shown on a task grid or designate which child tasks to show and which child tasks to hide when a specific mother grid task is selected. Thus, as explained with relationship to FIG. 71, a show/hide selection process may be initiated by selecting an action icon (as shown in FIG. 72). After an action is selected, a user may be prompted to select any task on the grid to designate that task as the mother task. As a result, the mother task's name may be displayed in the action box and child tasks for that mother may be highlighted, e.g., by a specified colors. As shown in FIG. 73, tasks to be shown when the mother task is selected are colored green and those hidden colored pink. Unaffected tasks retain the blue color. Subsequently the designation of the child tasks can be modified by selecting either shows or hides buttons shown in FIG. 72. Likewise, the modifications may be reversible.

By utilizing the Show-Hide Selection Logic screen(s) the user can determine which subset of tasks will be shown when the grid is initially displayed. Selecting the initial shows icon may change the color to a different color. This initialization process is distinct from the showing of tasks discussed in Organize Grid Tasks screen(s) discussed above (see FIG. 2) in that the latter controls the visibility of tasks selected after a task grid has been initialized.

A secondary use of benchmarking is to detect input errors; using the timing of performance of tasks that are sequentially related. Many errors can be prevented by using the show-hide logic presented above to minimize the number of tasks available for selection. However, keeping a task hidden until another is performed can also confuse the user, e.g., not being able to record a task when it is performed because the antecedent task was erroneously not entered. This is a prioritization issue that is discussed below where applicable. Examples of benchmarking results are shown in the description of the Code Analysis screen(s) explained above (see FIGS. 45-53).

In the Code Analysis screen, benchmark subsets may be defined and presented using the McMAID concept. These categories are explained further below; and they may be used to group the benchmarking processes into the following: Metronome, Chest Compressions (CC), Monitor (defibrillator), Airway, IV-IO, Drugs, and Pauses. Within each McMAID subgroup, pass/fail grades may be assigned to each benchmark item and pauses in compressions may be analyzed. Finally, an analysis of the time spent doing compressions, doing acceptable pauses, and doing unnecessary pauses may be performed.

Within the Metronome benchmarking category (FIG. 42), metronome usage may be tested for all code-types, e.g., was it used, if it was used, was it started on time.

Within the Monitor (Defibrillator) benchmarking category (FIG. 44), crash cart arrival may be tested for real and mock codes. For example, a crash cart should arrive within a benchmarked interval after the start of recording a Code; however, this may not be analyzed if the pre-code set has the crash cart present at the start of recording. Within the monitor usage benchmarking category, for most Real and Mock Codes the monitor is physically located on the crash cart. However, in some situations (e.g., AED may be available), a defibrillator/monitor may be used independently of crash cart arrival. Therefore, monitor usage may be treated independently of crash cart arrival; in fact it may be considered essential for any Code (e.g., without a monitor rhythm analysis and delivery of shocks is not possible). The program logic may prevent turning on the monitor until it is available. Although the analyze rhythm icon could have been hidden until it was selected (e.g., using show-hide logic), this may not be done because benchmarking the rhythms is more crucial than monitor usage.

Turning the monitor on as early as possible is encouraged because monitors record information vital to subsequent analysis of events: voice recording of events, continuous EKG recording, chest compression quality and etCO2 recordings. At least one disclosed embodiment may not incorporate this data into an immediate analysis process; however, at least one disclosed embodiment may incorporate this data.

Within the Monitor (Defibrillator) Pads benchmarking category (FIG. 44), it may be assumed that defibrillation paddles, common in older less effective monophasic defibrillators, are not used; instead defibrillation pads may be employed for this purpose. Therefore, paddles may not be included as a pre-code option; however, this could be done (as a customized version) if needed. Since the shockable/non-shockable nature of the Code is unknown until a rhythm analysis is performed, delaying pad application until after an analysis (using monitor leads) may be considered suboptimal care. Pad application therefore should be performed before a first rhythm analysis is anticipated. If doing CCR (which advocates an initial period of continuous chest compressions before the first rhythm analysis), it may not be, for example, done approximately two minutes after starting CC.

If doing CPR, there may be, within the monitor (Defibrillator) benchmarking category, no standard available. However, pads should be applied as soon as possible after a monitor is turned on because delaying sacrifices early EKG recording, However, such a delay may be necessary if staff is limited and other activities are more urgent.

Likewise, although rhythm analysis is possible using monitor leads, doing so may be suboptimal care because the purpose of analyzing is to deliver a shock if needed. Shocks cannot be delivered using monitor leads, and this mistake would be detected if there is a prolonged delay between rhythm analysis and the shock/no shock decision; or if they were placed after rhythm analysis.

Various criteria may be considered for benchmarking using the disclosed embodiments to analyze defibrillation (e.g., the application of shocks). For example, the disclosed embodiments may be utilized to determine whether all analyses have been followed by both a rhythm and shock/no-shock decision, determine whether all shocks were preceded by a rhythm analysis, whether all rhythms determinations were preceded by a rhythm analysis, determine whether there are any mismatches between rhythm and shock decision detected, and whether pauses for rhythm analyses have been managed appropriately. In one embodiment these inconsistencies may be detected in the analysis process, and the user is alerted by the use of a specific symbol (such as "***") preceding the fail comment. Clicking on the failed item then initiates an autocorrect process. An example of this would be not shocking a rhythm determined to be shockable; and if a shock was actually given (and recording of no-shock was a recording error) it can be corrected by the program to "Shock". Such logic has been applied to may potential analysis failures that are flagged as a failure when indeed they represent recording errors.

An expected sequence of actions may be: rhythm analysis (analysis), rhythm determination (rhythm), shock/no-shock decision. Thus, shock benchmarks may include the presence of all three actions being tested: rhythm analysis pauses without rhythms or Shocks/no-Shocks (e.g., fail: analysis @ 10:15:12 has no rhythm before Shock @ 10:15:18, fail: analysis @ 10:15:12 has no Shock after rhythm @10:15:15, fail: analysis @ 10:15:12 has no subsequent rhythm or Shock/no-Shock), rhythms without a preceding analysis (fail: no analysis before rhythm @10:15:12), and Shocks without a preceding analysis (fail: no analysis before Shock @10:15:12). Subsequently, the timing of the three actions may be evaluated: Duration of rhythm analysis—managed in Pause(s), the time interval between a shockable rhythm and the Shock (pass: Decision to Shock @10:15:25 was on Time (2 sec) after a shockable rhythm (BM is 5 sec), fail: Decision to Shock @10:15:25 was LATE (8 sec) after a shockable rhythm (BM is 5 sec)), the time interval between a non-shockable rhythm and no shock delivered (pass: Decision to not Shock @10:15:25 was on Time (2 sec) after a non-shockable rhythm (BM is 5 sec), fail: Decision to not Shock @10:15:25 was LATE (8 sec) after a non-shockable rhythm (BM is 5 sec)), and an Inappropriate rhythm-Shock/no-Shock decision (fail: shockable rhythm @10:15:12 was NOT shocked, fail: non-shockable rhythm @10:15:12 WAS shocked). Because some of the fails may represent recording errors, an opportunity may be provided to correct them and then reanalyze the Code before a final analysis is performed.

Likewise, if a Chest Compressions device, such as a LUCAS, is used, corresponding benchmarks are invoked. For example, the disclosed embodiments may be utilized to determine and analyze the application (pass: LUCAS—Was Applied before Start of Recording, pass: LUCAS—Was Re-applied & Operational at 01:30, fail: LUCAS was available but never applied, fail: LUCAS application started but never completed, pass: Unable to judge LUCAS application because Start time was not recorded, pass: LUCAS was applied in 10 sec (BM is 10 sec), fail: LUCAS was applied in 20 sec (BM is 10 sec)), and failure (pass: LUCAS—failed at 00:30, pass: Presumed LUCAS failure because CC were started after LUCAS application).

A set of chest compressions (CC) (FIG. 43) may be defined as an interval bordered by adjoining actions that begin and end compressions. Pauses and other actions/events may exist in this interval. The final set may end by the earliest of ROSC or the End of Recording. Thus, resumption of cardiac compressions after ROSC (lost ROSC) may be managed. Within a set of CC the following are calculated: the total time (sec) of a set, the total time (sec) of CC, and the total time (sec) of pauses. Likewise, the duration of the set of compressions may be benchmarked (fail: CC Set @15:08:59 was too BRIEF, lasting 29 sec (BM is 100 sec), fail: CC Set @15:08:59 was too LONG, lasting 200 sec (BM is 150 sec), pass: 90.1% of CC were in Sets with acceptable durations (BM is 100-150 sec)).

Compressions may be considered fresh if they were done during a specified benchmark interval (e.g., 75 seconds). Those performed after the benchmark 75 seconds (without switching compressors) may be deemed not Fresh. This distinction is made because the quality of continuously performed compressions deteriorates after about 60-75 seconds.

Likewise, switching compressors during CC may be benchmarked (fail: CC Set starting @14:54:31 went 237 sec without a switch of compressors (BM is 75 sec), pass: 60.1% of CC were performed with fresh compressors).

The disclosed embodiments may be utilized to determine and analyze tasks regarding a patient's airway (FIG. 45). When initial airway tasks have been performed before the start of a Code (see pre-code sets), they may not be benchmarked (pass: Initial Airway Maneuvers not needed). Otherwise, they may be tested against the start of recording time. In the benchmarks below, the word title could mean one of the following: airway patency check, OPA/NA insertion or O2 application (fail: title was not performed, pass: title @10:15:56 was On Time (200 sec after start of recording) (BM is 120 sec), fail: title @10:15:56 was LATE (200 sec after start of recording) (BM is 120 sec)). If an invasive airway fails, initial airway tasks are not retested. An invasive airway (ET or other type) is almost always needed—but occasionally it is not (such as when the patient is gasping regularly at an adequate rate or if ROSC with adequate ventilation occurred before airway would have been inserted). Because this is rare, it is not tested in the program and can be managed by an entry in the comment section during the archiving process. If a Code protocol uses CCR, the initial rhythm may be used in the benchmarking process. If that rhythm is shockable, invasive airway insertion is delayed for 3 CC "cycles" or approximately 6 minutes. Therefore, no benchmarking may be possible if no rhythm was recorded, the Code ended before a first rhythm was recorded, or ROSC occurred before a first rhythm was recorded. All of this logic may not apply if responders were performing CPR. In accordance with at least one disclosed embodiment, an assumption may be made that a responder who starts with CPR (a pre-code decision) does not switch to CCR during the Code.

As part of the airway tasks benchmarked (FIG. 45), invasive airway failure is tested (if it did NOT occur: pass: failure of invasive airway—did NOT occur, if it DID occur: pass: failure of invasive airway—RETRY was attempted, fail: failure of invasive airway—NO RETRY was attempted). Invasive airway insertion may not be tested (pass: invasive airway—N/A (done before start of recording), pass: invasive airway—N/A (not doing CCR), pass: invasive airway—N/A (no Initial rhythm detected), pass: invasive airway not needed—ROSC or End of Code occurred)). Alternatively, invasive airway insertion may be tested. In some of results, the actual name of the invasive airway (ET, Combitube, etc.) may be used; thus, the term title may be replaced by that name (fail: no invasive airway was Started and One was needed). It is determined, whether an invasive airway, when using CCR, has been inserted before a rhythm is analyzed (fail: title was Started BEFORE rhythm analysis done), if the initial rhythm was not shockable (pass: title Insertion @10:15:25 was On Time (15 sec) after an initially non-shockable rhythm (BM is 30 sec), fail: title Insertion @10:15:25 was late (45 sec) after an initially non-shockable rhythm (BM is 30 sec)), if an initial rhythm was shockable (fail: title Insertion @ 10:15:25 was too EARLY (200 sec) after an initially shockable rhythm (BM is 360-390 sec), fail: title Insertion @ 10:15:25 was too LATE (400 sec) after an initially shockable rhythm (BM is 360-390 sec), pass: title Insertion @ 10:15:25 was too EARLY (370 sec) after an initially shockable rhythm (BM is 360-390 sec)).

The disclosed embodiments may be utilized to determine and analyze the use of end tidal CO2 test; however, these may be tested only if such a test is in a relevant protocol (which is a pre-code issue). For example, the test may not be in the protocol (pass: etCO2—NOT in protocol), may not be tested if etCO2 was applied before the start of Code Recordation (pass: etCO2 in place Before recording started), or may not be tested if no invasive airway was inserted (pass: etCO2 not needed—no invasive airway inserted). A recording error warning may be generated if etCO2 use is recorded but no airway insertion is recorded (fail: * etCO2 used but NO invasive airway insertion recorded *) (where the *** indicate an auto-correction is available—in this example it would fix the failure by recording an invasive airway insertion with an appropriate time stamp). Likewise, an error may occur if etCO2 is in the relevant protocol but detection device(s) are not available (fail: etCO2—IN protocol but neither Main- or Side-Stream available).

If detection devices were available and an invasive airway was used (title refers to name of invasive airway device), the disclosed embodiment may detect various recording errors (premature etCO2 use only applies if only Mainstream is used; fail: * etCO2 used but NO invasive airway insertion recorded *; or fail: * Mainstream etCO2 start @10:25:12 was BEFORE airway insertion @10:25:30 *). However, the disclosed embodiments may also detect and analyze if etCO2 was not used (fail: Mainstream etCO2 was available but NEVER used after title insertion @10:15:25, fail: Sidestream etCO2 was available but NEVER used). Similarly, detection and analysis of whether sidestream etCO2 was used (fail: Sidestream etCO2 start @10:25:12 was LATE (100 sec) after start of recording (BM is 30 sec), pass: Sidestream etCO2 start @10:25:12 was on Time (20 sec) after start of recording (BM is 30 sec)), and/or mainstream was used (timing can only be tested if Sidestream not available: pass: Mainstream etCO2 @ 10:25:15 started On Time (15 sec) after Airway @10:25:00 (BM is 20 sec), and fail: Mainstream etCO2 @ 10:25:45 started LATE (45 sec) after Airway @10:25:00 (BM is 20 sec)).

The disclosed embodiments may be utilized to determine the appropriateness of pausing CC for various recorded reasons. One example of such a pause is that for checking a pulse, which should never be performed if etCO2 is available (even it not used). The duration of pauses for pulse checks may be managed using functionality provided by at least one of the screens provided in the GUI. If etCO2 is operational (defined as the interval(s) between etCO2 applications and adjoining failures). Disclosed embodiments may be utilized to determine and analyze if no pulse check done (pass: etCO2—Used and NO pulse checks done) and pulse check(s) done and etCO2 operational (fail: etCO2—Pulse Check @ 00:20 is NOT ACCEPTABLE—etCO2 was available).

The disclosed embodiments may be utilized to determine and analyze performance of IV/IO tasks (FIG. 46), for example, whether they were started in time, the time spent inserting IV/IO (from "Start" to "Done") and whether an IV was attempted or re-attempted prior to attempting to start an IO.

Similarly, the disclosed embodiments may be utilized to determine and analyze the application of drugs (FIG. 47) including the timing of a first dose in relation to a preceding activity, whether and when repeat doses were given, and whether AHA standards were used when timing the use of Amiodarone given after shockable rhythms were detected. For example, if a drug is indicated only after a specific action and it is administered before that action, a fail is generated (e.g. Amiodarone use is dependent upon the presence of a shockable rhythm).

It should be understood that protocols, if used, define a number of issues that are used in benchmarking drug usage. The application of specific drugs is only tested as part of benchmarking if they are in a protocol being used. For example, certain drugs may not be within a protocol, e.g., Vasopressin, Amiodarone, or Epinephrine.

In accordance with at least one embodiment, only IV drugs may be recorded; thus, grid show-hide logic for such an embodiment may only display drugs when an IV or IO is operational.

In particular, when determining and analyzing administration of Epinephrine (Epi), various parameters may be analyzed for benchmarking, including whether Epi was in protocol and indicated but not given, an interval between the first Epi dose and when an IV or IO was operational, determining the number of actual and expected Epi doses and their timing. Similarly, the timing of one or more doses of Amiodarone is determined and analyzed in relationship to AHA standards (if they are used) on administration in relationship to detection of a persistent or recurrent shockable rhythm. Similar analysis may be performed for Vasopressin.

Additionally, disclosed embodiments may be used to determine and analyze whether specific drugs were administered that almost always should not be given during a Code, e.g., Atropine, Bicarb or Calcium.

In accordance with disclosed embodiments, the timing and length of various pauses (FIG. 48) may be benchmarked including those associated with, for example, Endotracheal tube (ET) insertion, rhythm analysis, application of defibrillation pads, ventilation of the patient, charging the defibrillator, pulse checks, resuming CC after a shock/no-shock decision, peeking at rhythm, switching chest compressors, application of an automatic compression device, etc. For each of the pauses analyzed, various details are recorded for analysis including the number of times they occurred during the Code, the total of acceptable seconds—the portion of pauses seconds within the benchmark interval, and the total of unnecessary seconds—the portion that exceeded the benchmark interval.

Various pre-code issues may be utilized in the analysis of some pauses, as shown in Table 4.

TABLE 4

| Pause Type | Type of CPR | | Type of Defibrillator | | Use of etCO2 |
| --- | --- | --- | --- | --- | --- |
| | CPR | CCR | AED | Manual | etCO2 |
| to insert ET | X | X | — | — | — |
| To apply Pads | X | X | — | — | — |
| For Ventilation(s) | X | X | — | — | — |
| To Charge(s) defibrillator | X | X | X | — | — |
| Other(s) | — | — | — | — | — |
| For Pulse Check(s) | X | X | — | — | X |
| For Rhythm Analyses (? Need shock or not) | — | — | X | X | — |

The disclosed embodiments may be utilized to determine and analyze performance (e.g., whether it occurred and its timing) of ET insertion, rhythm analysis, application of pads, ventilation, defibrillator charging, pulse checks, the use of automatic chest compressions devices, etc. In accordance with at least one disclosed embodiment, each benchmark may be categorized (and displayed on the GUI or output in one or more reports) according to a corresponding category, e.g., the McMAID category illustrated in Tables 5-9.

TABLE 5

| Sec | Metronome |
|---|---|
| 15 | Metronome - To Start after Starting CC |
| 15 | Metronome - To Start after Starting CC |

TABLE 6

| Sec | Compression |
|---|---|
| 8 | Start CC - after Prior Rhythm detected |
| 20 | Start CC - after Start of Recording |
| 75 | CC - Time between Switching Compressors |
| 100 | CC - Duration - Min |
| 150 | CC - Duration - Max |
| 20 | Start CC - after Prior Rhythm Analysis - AED |
| 3 | Start CC - after Prior Shock/NoShock |
| 8 | Start CC - after Prior Rhythm Analysis - Manual |
| 8 | Start CC - after Prior Rhythm detected |
| 8 | Start CC - after Prior Rhythm Analysis - Manual |
| 20 | Start CC - after Prior Rhythm Analysis - AED |
| 20 | Start CC - after Start of Recording |
| 3 | Start CC - after Prior Shock/NoShock |
| 150 | CC - Duration - Max |
| 75 | CC - Time between Switching Compressors |
| 100 | CC - Duration - Min |

TABLE 7

| Sec | Monitor |
|---|---|
| 10 | To Charge - using Manual defibrillator |
| 0 | To Charge - using CCR & Manual defibrillator |
| 10 | To Charge - using Manual defibrillator |
| 10 | To Analyze Rhythm - AED |
| 10 | Pads - To apply - doing CPR |
| 10 | Pads - To apply - doing CPR |
| 15 | To Charge - using AED |
| 5 | Pads - To apply - doing CCR |
| 5 | To Analyze Rhythm - Manual defibrillator |
| 5 | To Shock - after Rhythm Analysis |
| 10 | To Analyze Rhythm - AED |
| 30 | Monitor - To Turn on after it's available |
| 5 | To Shock - after Rhythm Analysis |
| 5 | Pads - To apply - doing CCR |
| 5 | To Analyze Rhythm - Manual defibrillator |
| 3 | To Shock - after shockable Rhythm |
| 15 | To Charge - using AED |
| 3 | To Shock - after shockable Rhythm |
| 30 | Monitor - To Turn on after it's available |
| 0 | To Charge - using CCR & Manual defibrillator |

TABLE 8

| Sec | Airway |
|---|---|
| 0 | To Ventilate if doing CCR |
| 30 | Max Time after Initially nonSockable to Start ET |
| 60 | Start Sidestream etCO2 - after Start of Recording |
| 120 | Initial Airway - after Start of Recording |
| 360 | Invasive airway - Earliest time after Initial Rhythm - shockable |
| 360 | Invasive airway - Earliest time after Initial Rhythm - shockable |
| 120 | Initial Airway - after Start CC |
| 390 | Invasive airway - Latest time after Initial Rhythm - shockable |
| 390 | Invasive airway - Latest time after Initial Rhythm - shockable |
| 0 | To Ventilate if doing CCR |
| 30 | Max Time after Initially nonSockable to Start ET |
| 30 | Invasive airway - Max time after Initial Rhythm - non-shockable |
| 15 | Start Mainstream etCO2 - after Invasive airway ready |
| 120 | Initial Airway - after Start of Recording |
| 30 | Invasive airway - Max time after Initial Rhythm - non-shockable |
| 5 | To Ventilate if doing CPR |

TABLE 8-continued

| Sec | |
|---|---|
| 5 | To Ventilate if doing CPR |
| 120 | Initial Airway - after Start CC |
| 15 | Start Mainstream etCO2 - after Invasive airway ready |
| 60 | Start Sidestream etCO2 - after Start of Recording |
| | IV IO |
| 3 | Max # of Epi doses allowed |
| 3 | Max # of Epi doses allowed |
| 20 | Max time to Insert IO |
| 20 | Max time to Insert IV |
| 20 | Max time to Insert IO |
| 20 | Max time to Insert IV |

TABLE 9

| Sec | Drugs |
|---|---|
| 15 | Max time 1st dose Epi after IV or IO ready |
| 30 | Max time between 1st Epi and 1st Vasopressin |
| 540 | Min time between 2nd and 1st Vasopressin doses |
| 180 | Min time between Epi doses |
| 300 | Max time between Epi doses |
| 660 | Max time between 2nd and 1st Vasopressin doses |
| 660 | Max time between 2nd and 1st Vasopressin doses |
| 15 | Max time 1st dose Epi after IV or IO ready |
| 30 | Max time between 1st Epi and 1st Vasopressin |
| 540 | Min time between 2nd and 1st Vasopressin doses |

The following example (Table 10) provides additional information detailing all events recorded during a code and their timing. The display of timing can be the interval from the start of the code or it can be adjusted to display real time if the time the code started is available. If the Code has been saved (archived), a report header for the Code may contain various information such as who was the Recorder, physician, nursing staff and other personnel involved in the Code, the actual time the Code began (Real and Run Report Codes), where the Code occurred, date of the Code, and type of Code. Only some of this data may be available for preliminary analyses.

TABLE 10

| Clock | Real Time | Action |
|---|---|---|
| 00:00 | 00:00:00 | Crash Cart present before Start of Recording |
| 00:00 | 00:00:00 | Crash Cart Arrived |
| 00:00 | 00:00:00 | Doing CCR (not CPR) |
| 00:00 | 00:00:00 | Using Manual Defibrillator |
| 00:00 | 00:00:00 | Start of Recording |
| 01:31 | 00:01:31 | Pads on @ start of recording |
| 01:31 | 00:01:31 | Start CC |
| 01:56 | 00:01:56 | Monitor Here |
| 01:56 | 00:01:56 | Monitor Turned On |
| 03:09 | 00:03:09 | Analyze Rhythm |
| 03:15 | 00:03:15 | shockable Rhythm |
| 03:17 | 00:03:17 | Resume after Shock |
| 03:22 | 00:03:22 | SAME person |
| 05:24 | 00:05:24 | shockable Rhythm |
| 05:24 | 00:05:24 | Analyze Rhythm |
| 05:26 | 00:05:26 | Resume after Shock |
| 05:28 | 00:05:28 | Switch CC |
| 07:28 | 00:07:28 | Analyze Rhythm |
| 07:28 | 00:07:28 | shockable Rhythm |
| 07:31 | 00:07:31 | Resume after Shock |
| 07:34 | 00:07:34 | Switch CC |
| 08:00 | 00:08:00 | IV Retry |
| 09:08 | 00:09:08 | Epinephrine |
| 09:33 | 00:09:33 | Analyze Rhythm |
| 09:33 | 00:09:33 | shockable Rhythm |
| 09:35 | 00:09:35 | Resume after Shock |

TABLE 10-continued

| Clock | Real Time | Action |
|---|---|---|
| 10:03 | 00:10:03 | Switch CC |
| 10:13 | 00:10:13 | Peek at Rhythm |
| 10:24 | 00:10:24 | Switch CC |
| 10:54 | 00:10:54 | Pulse Check |
| 10:56 | 00:10:56 | SAME person |
| 11:34 | 00:11:34 | Analyze Rhythm |
| 11:35 | 00:11:35 | shockable Rhythm |
| 11:36 | 00:11:36 | Resume after Shock |
| 11:44 | 00:11:44 | Switch CC |
| 12:13 | 00:12:13 | for Other Reason |
| 12:16 | 00:12:16 | SAME person |
| 13:32 | 00:13:32 | Analyze Rhythm |
| 13:32 | 00:13:32 | shockable Rhythm |
| 13:34 | 00:13:34 | Resume after Shock |
| 13:37 | 00:13:37 | Switch CC |
| 13:43 | 00:13:43 | Peek at Rhythm |
| 13:49 | 00:13:49 | Switch CC |
| 14:00 | 00:14:00 | Start IO |
| 14:00 | 00:14:00 | IO Operational |
| 14:00 | 00:14:00 | Amiodarone 300 mg bolus |
| 14:30 | 00:14:30 | for Other Reason |
| 14:31 | 00:14:31 | SAME person |
| 15:19 | 00:15:19 | for Other Reason |
| 15:21 | 00:15:21 | Switch CC |
| 15:34 | 00:15:34 | Analyze Rhythm |
| 15:35 | 00:15:35 | shockable Rhythm |
| 15:38 | 00:15:38 | Resume after Shock |
| 15:59 | 00:15:59 | Switch CC |
| 16:00 | 00:16:00 | ROSC |
| 16:26 | 00:16:26 | for Other Reason |
| 16:28 | 00:16:28 | SAME person |
| 17:34 | 00:17:34 | ROSC |
| 17:35 | 00:17:35 | Analyze Rhythm |
| 17:39 | 00:17:39 | non-shockable |
| 18:00 | 00:18:00 | IV failed |
| 18:00 | 00:18:00 | IV Retry |
| 18:00 | 00:18:00 | IV operational |
| 19:00 | 00:19:00 | Amiodarone 150 mg bolus |
| 19:00 | 00:19:00 | Other Drug |
| 19:10 | 00:19:10 | End of Code |

Thus, in one example, the results of benchmarking analysis may be arranged by pass/fail and within these two categories by, for example, McMAID order, as shown in Tables 11-12.

TABLE 11

Passed

Compressions
60.1% of CC were performed with "Fresh" Compressors
90.1% of CC were in Sets with acceptable durations (BM of 100-150")
Monitor
Pad application - Occurred BEFORE 1st Rhythm Analysis
Crash Cart - Present before start of recording
Decision to @15:10:39 was On Time (−1059") after a non-shockable Rhythm (BM is 3")
Decision to Shock @14:56:15 was On Time (2") after a shockable Rhythm (BM is 3")
Decision to Shock @14:58:24 was On Time (2") after a shockable Rhythm (BM is 3")
Decision to Shock @15:00:28 was On Time (3") after a shockable Rhythm (BM is 3")
Decision to Shock @15:02:33 was On Time (2") after a shockable Rhythm (BM is 3")
Decision to Shock @15:04:35 was On Time (1") after a shockable Rhythm (BM is 3")
Decision to Shock @15:06:32 was On Time (2") after a shockable Rhythm (BM is 3")
Monitor - On 0" after available (BM is 30")
Decision to Shock @15:08:35 was On Time (3") after a shockable Rhythm (BM is 3")
Airway
Failure of Invasive Airway - Did NOT occur
etCO2 not needed - no invasive airway inserted

TABLE 11-continued

Passed

Drugs
Amiodarone - 2nd Dose was 150 mg
Amiodarone - 1st Dose was 300 mg
Pauses
no pauses for ET Insertion occurred
no pauses for Ventilations occurred
no pauses for Apply LUCAS occurred
no pauses for Charging occurred
no pauses for Applying Pads occurred

TABLE 12

Failed

Metronome
Metronome - was NOT Used
Compressions
CC Set @15:08:59 was too BRIEF, lasting 29" (BM is 100")
CC Set starting @14:54:31 went 237" without a Switch of Compressors (BM is 75")
LUCAS was available but never applied
CC Set starting @15:06:49 went 92" without a Switch of Compressors (BM is 75")
CC Set starting @15:04:44 went 113" without a Switch of Compressors (BM is 75")
CC Set starting @15:03:24 went 80" without a Switch of Compressors (BM is 75")
CC Set starting @15:00:34 went 149" without a Switch of Compressors (BM is 75")
CC Set @15:09:28 was too BRIEF, lasting 66" (BM is 100")
CC Set starting @14:58:28 went 126" without a Switch of Compressors (BM is 75")
Monitor
no Analysis before rhythm @14:58:24
no Analysis before rhythm @15:06:32
no Shock after Rhythm @15:10:39
Airway
O2 Application was not performed
no Invasive Airway was Started and One was needed
Airway Patency Check was not performed
OPA/NPA insertion was not performed
IV-IO
IV Retry @15:01:00 was BEFORE IO attempt @15:07:00
IV/IO - Neither IV or IO attempted
Drugs
There were 112" between ROSC and last Epi @15:02:08 where a repeat dose was indicated
1 dose of Epi was given after IO Completed - too MANY (BM is 0-0 doses)
Amiodarone - 1st dose @15:07:00 was 615" LATE (after 1st shockable rhythm) (BM is 30")
Amiodarone - 2nd dose @15:12:00 was 786" LATE (after 2nd shockable rhythm) (BM is 30")
Pauses
for Other Reason Pauses - All (8") were NOT necessary
Peek at Rhythm Pauses - All (17") were NOT necessary
71% of 7 Resume CC after Shock/noShock pauses (50 of 70") were NOT necessary
11% of 8 Analyze Rhythm pauses (3 of 27") were NOT necessary
Pulse Check Pause - All (2") were NOT necessary
Details of All Pauses that occurred during the Code In accordance with at least one disclosed embodiment (FIG. 49), the total number of pauses for a given type of pause may be calculated as well as the total seconds that pauses took away from chest compressions. Similarly, some pauses may be acceptable, but only up to a benchmarked limit, and pauses that exceed that limit may be considered unacceptable. Likewise, the duration of the Code, i.e., from beginning of recording to the earliest of Return Of Spontaneous Circulation (ROSC) (sustained) or the end of recording may be documented. This allows computation of the percent of time spent doing chest compressions in two scenarios: actual and ideal (if unnecessary pauses were eliminated). This is very relevant because unnecessary time not doing compressions is known to decrease survival.

Thus, it should be understood that the Code recordation, documentation and analysis provided in accordance with the disclosed embodiments is varied and far reaching. A point that must be emphasized is that an objective analysis of a code is available for review by the members of the resuscitation team or trainee as soon as the code is completed. All data generated during cardiac arrest events may also be archived so as to be stored in a meaningful and accessible way for subsequent review at a later date. The information relevant to the type of Code (e.g. physician and registered nurse in charge, Utstein information, etc.) may be collected and stored and that information may be used to sort the archived data. In this way, the data is generated in real time during a cardiac arrest event and is accessible and comparable with data from other events that share common characteristics. Moreover, the disclosed embodiments enable the ability to judge, monitor, track and document the efficacy of certain drugs, treatment protocols, individuals, teams of personnel, equipment, and timing of tasks performed during a Code in a more objective manner using documented benchmarking.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention For example, as explained above, the description of the system, equipment and methodology provided herein is merely exemplary and is not limiting. Thus, it should be understood that the disclosed embodiments may be functional to perform recordation, analysis, feedback, training, and post event processing without reference to, or use of, protocol or pre-code data because there are other ways of implementing the functionality beyond the implementation provided by the code included in the Appendix.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed is:
1. A system for management of cardiac arrest events, the system comprising:
   at least one processor;
   at least one memory storing program instructions and archived data for execution by the at least one processor that controls display of a graphical user interface, the archived data including a set of rules for managing events that may occur during a cardiac arrest event, data generated by recording user's interaction with the icons during the cardiac arrest event, including documenting and analyzing of events pertaining to diagnosing, treatment and monitoring of a patient, the memory being accessible and comparable with data from other events that share common characteristics, the memory being accessible by post-event data processing systems;
   at least one display presenting the graphical user interface comprising a plurality of screens with icons for interaction by a user including at least a developer, an administrator, and a recorder, each of the icons representing tasks and actions that occur during cardiac arrest events categorized into at least four code-types including:
      a real code-type enabling real time recordation, documentation, analysis and feedback to personnel treating a real person having a cardiac arrest, the real code-type enabling adjustment of retrospective timing to an actual time of a start of the events that preceded initial recording,
      a mock code-type pertaining to scenarios mimicking events of the real type and including an onset time recordation of all details regarding cardiac arrest actions and events, protocols and equipment availability,
      a testing code-type pertaining to training with all equipment being available, and
      a run report code-type providing entry of data in retrospect from various sources;
   wherein the plurality of screens comprises:
      at least one screen displaying an array of icons and a task grid for the developer or administrator to initially assign a name of one of the tasks and/or actions to each of the icons and to determine an initial subset of icons shown on the grid, the icons being displayed in a context-sensitive manner such that icons for completed-tasks are hidden and/or drug-associated icons are shown after the user selects an icon associated with drug administration,
      at least one show-hide selection screen enabling an administrator or developer to set up relationships between tasks and to designate which child-task icons to show and to hide when a mother-task icon is selected,
      at least one screen displaying an option for setting up code-types that will be used by the system and enabling the administrator to create new codes-types and modify existing code-types,
      at least one screen for each of the code-types and displaying actions and events that may occur during such code-type event,
      at least one screen displaying an option to modify names of the icons displayed on the task grid for the administrator to select a name that fits into a space of the icon and is from a list of recognized words,
      at least one screen displaying a list of all developed code-types, the user initiating a sequence of screens by selecting a code-type from the list, the administrator being allowed to create a new sequence of screens and to modify existing sequences, at least one recording screen for recording events of the selected code-type, the at least one recording screen displaying an option for the user to select icons associated with tasks and/or actions displayed on the task grid, to start a clock of the system for entering data and displaying status selected task or action, at least one analysis screen displaying an option for selecting recorded task(s) and/or actions(s) and permitting the user to select a recorded event displaying details of the code with times using 24-hour clock format, and at least correction screen displaying an option to correct recording errors and re-analyze the cardiac arrest event.

2. The system of claim 1 wherein the post-event data processing systems include at least training software, accreditation systems, accounting systems and inventory systems providing data for post cardiac event processing such as inventory control, billing purposes, liability management and further medical research.

3. The system of claim 1 wherein at least one of the screens enables linking of voice recognition technology to task recordation options.

4. The system of claim 3 further comprising a speaker and a microphone, the processor running a software code which controls receiving audio input from, and providing audio output to individuals involved in treatment of a cardiac arrest event.

5. The system of claim 1 wherein the icon selection results from touching one of the plurality of icons on a touch screen.

* * * * *